(12) United States Patent
Aljada

(10) Patent No.: US 10,151,001 B2
(45) Date of Patent: Dec. 11, 2018

(54) QUANTIFICATION OF LAMIN C AND LAMIN A FOR TUMOR CLASSIFICATION

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Ahmad Samir Aljada, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 119 days.

(21) Appl. No.: 14/983,084

(22) Filed: Dec. 29, 2015

(65) Prior Publication Data

US 2016/0208337 A1    Jul. 21, 2016

Related U.S. Application Data

(60) Provisional application No. 62/097,507, filed on Dec. 29, 2014.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/112* (2013.01); *C12Q 2600/136* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 2004/0018546 | A1 | 1/2004 | Hung |
| 2010/0297618 | A1 | 11/2010 | Hutchison et al. |
| 2011/0033873 | A1 | 2/2011 | Park et al. |
| 2014/0248637 | A1 | 9/2014 | Cho et al. |

FOREIGN PATENT DOCUMENTS

| WO | WO 2007/148095 A2 | 12/2007 |
| WO | WO 2013/086637 A1 | 6/2013 |

OTHER PUBLICATIONS

Miranda (Obesity 2008 vol. 16 pp. 1742-1748).*
Whitehead (Genome Biology 2005 vol. 6 Issue 2 Article R13).*
Xu (PloS ONE Oct. 2010 vol. 5 Issue 10 e13696 pp. 1-8).*
Thisted (What is a P value? The University of Chicago 1998 http://www.stat.uchicago.edu/~thisted).*
Dermer (Biotechnology 1994 vol. 12 p. 320).*
Coleman (Drug Discovery Today. 2003. 8: 233-235).*
Umar Wazir, et al., "The Clinicopathological Significance of Lamin A/C, Lamin B1 and Lamin B receptor mRNA Expression in Human Breast Cancer", Cell Mol. Biol. Lett., vol. 18, No. 4, Dec. 2013, 17 pages (with Abstract).
Naomi D. Willis, et al., "Lamin A/C is a Risk Biomarker in Colorectal Cancer", PLOS ONE, www.plosone.org, vol. 3, Issue 8, e2988, Aug. 2008, 9 pages.

* cited by examiner

*Primary Examiner* — Amanda Haney
(74) *Attorney, Agent, or Firm* — Oblon, McClelland, Maier & Neustadt, L.L.P.

(57) ABSTRACT

A method for detecting cancer by determining ratios of alternatively spliced Lamin A/C gene mRNAs in tissue samples, especially an increased ratio of Lamin C to Lamin A mRNAs. Therapeutic for subjects having a tumor or cancer characterized by an elevated ratio of Lamin C to Lamin A mRNA or protein.

2 Claims, 17 Drawing Sheets

Figure 2A:
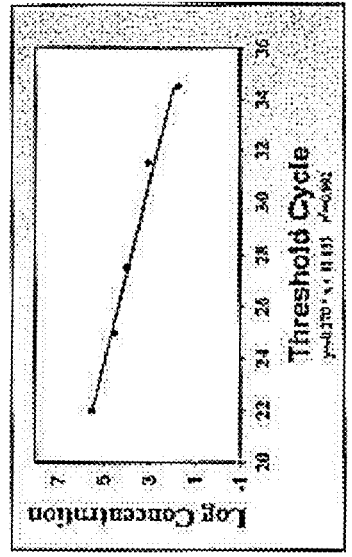
Figure 2B:
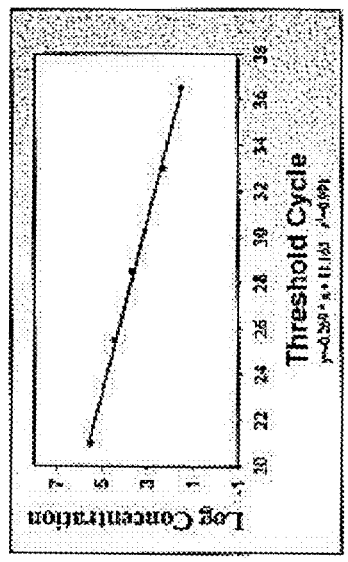
Figure 2C:
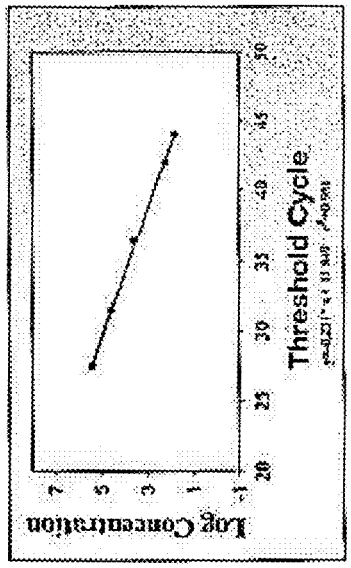
Figure 2D:
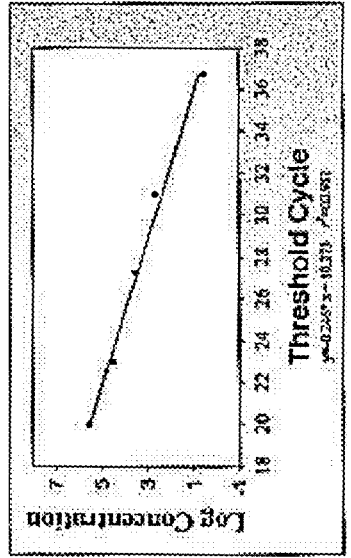

Specification includes a Sequence Listing.

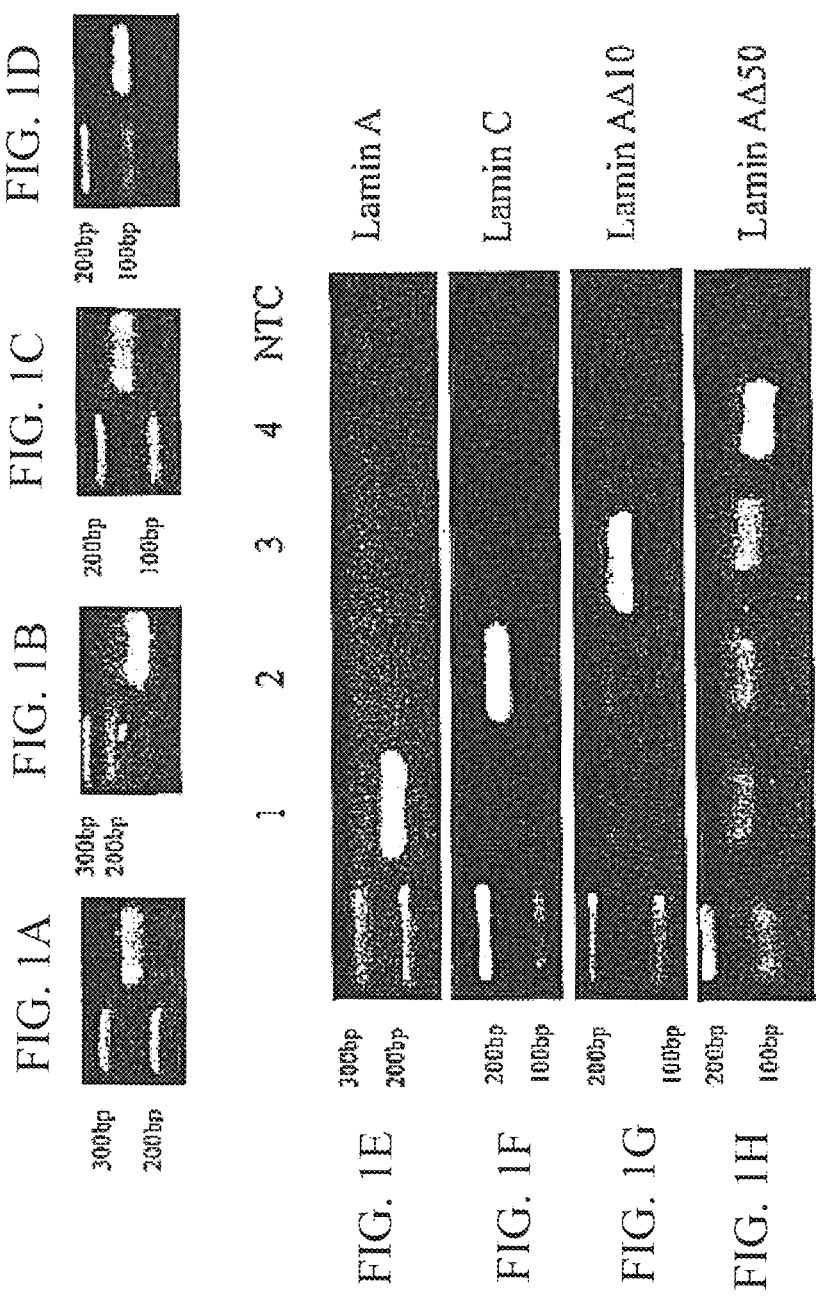

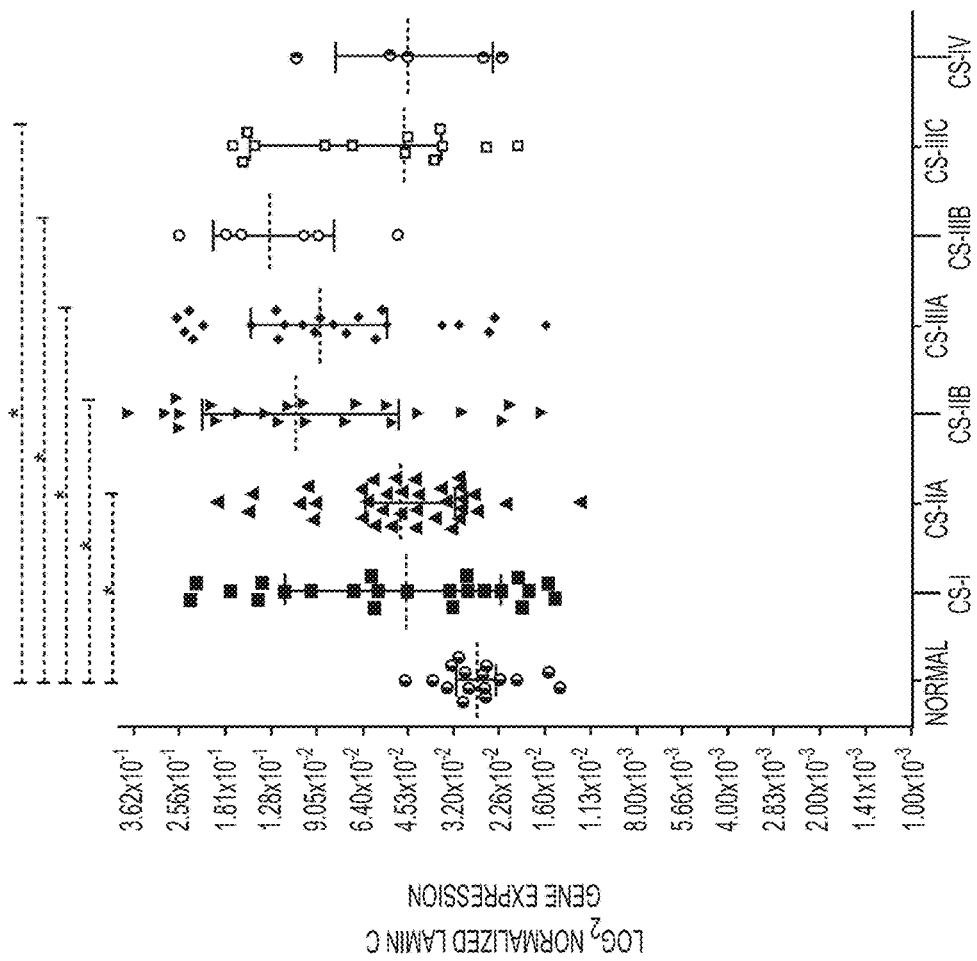

SEQUENCE LISTING

```
<160> NUMBER OF SEQ ID NOS: 32

<210> SEQ ID NO 1
<211> LENGTH: 3239
<212> TYPE: DNA
<213> ORGANISM: Homo sapiens
<220> FEATURE:
<221> NAME/KEY: CDS
<222> LOCATION: (250)..(2244)
<223> OTHER INFORMATION: Lamin isoform A is encoded by lamin transcript
      variant 1.  NCBI Reference Sequence: NM_170707.3.

<400> SEQUENCE: 1
aggaggacct attagagcct tgccccggc gtcggtgact cagtgttcgc gggagcgccg      60
cacctacacc agccaaccca gatcccgagg tccgacagcg cccggcccag atccccacgc     120
ctgccaggag caagccgaga gccagccggc cggcgcactc cgactccgag cagtctctgt     180
ccttcgaccc gagccccgcg cccttccgg gacccctgcc ccgcgggcag cgctgccaac      240 ctgccggcc atg gag acc ccg tcc cag cgg cgc gcc acc cgc agc ggg gcg    291
            Met Glu Thr Pro Ser Gln Arg Arg Ala Thr Arg Ser Gly Ala
            1               5                   10 cag gcc agc tcc act ccg ctg tcg ccc acc cgc atc acc cgg ctg cag        339
Gln Ala Ser Ser Thr Pro Leu Ser Pro Thr Arg Ile Thr Arg Leu Gln
 15                  20                  25                  30 gag aag gag gac ctg cag gag ctc aat gat cgc ttg gcg gtc tac atc        387
```

```
                Glu Lys Glu Asp Leu Gln Glu Leu Asn Asp Arg Leu Ala Val Tyr Ile
                             35                  40                  45 gac cgt gtg cgc tcg ctg gaa acg gag aac gca ggg ctg cgc ctt cgc       435
Asp Arg Val Arg Ser Leu Glu Thr Glu Asn Ala Gly Leu Arg Leu Arg
             50                  55                  60 atc acc gag tct gaa gag gtg gtc agc cgc gag gtg tcc ggc atc aag       483
Ile Thr Glu Ser Glu Glu Val Val Ser Arg Glu Val Ser Gly Ile Lys
             65                  70                  75 gcc gcc tac gag gcc gag ctc ggg gat gcc cgc aag acc ctt gac tca       531
Ala Ala Tyr Glu Ala Glu Leu Gly Asp Ala Arg Lys Thr Leu Asp Ser
         80                  85                  90 gta gcc aag gag cgc gcc cgc ctg cag ctg gag ctg agc aaa gtg cgt       579
Val Ala Lys Glu Arg Ala Arg Leu Gln Leu Glu Leu Ser Lys Val Arg
95                 100                 105                 110 gag gag ttt aag gag ctg aaa gcg cgc aat acc aag aag gag ggt gac       627
Glu Glu Phe Lys Glu Leu Lys Ala Arg Asn Thr Lys Lys Glu Gly Asp
                115                 120                 125 ctg ata gct gct cag gct cgg ctg aag gac ctg gag gct ctg ctg aac       675
Leu Ile Ala Ala Gln Ala Arg Leu Lys Asp Leu Glu Ala Leu Leu Asn
            130                 135                 140 tcc aag gag gcc gca ctg agc act gct ctc agt gag aag cgc acg ctg       723
Ser Lys Glu Ala Ala Leu Ser Thr Ala Leu Ser Glu Lys Arg Thr Leu
        145                 150                 155 gag ggc gag ctg cat gat ctg cgg ggc cag gtg gcc aag ctt gag gca       771
Glu Gly Glu Leu His Asp Leu Arg Gly Gln Val Ala Lys Leu Glu Ala
    160                 165                 170 gcc cta ggt gag gcc aag aag caa ctt cag gat gag atg ctg cgg cgg       819
Ala Leu Gly Glu Ala Lys Lys Gln Leu Gln Asp Glu Met Leu Arg Arg
175                 180                 185                 190 gtg gat gct gag aac agg ctg cag acc atg aag gag gaa ctg gac ttc       867
Val Asp Ala Glu Asn Arg Leu Gln Thr Met Lys Glu Glu Leu Asp Phe
                195                 200                 205 cag aag aac atc tac agt gag gag ctg cgt gag acc aag cgc cgt cat       915
Gln Lys Asn Ile Tyr Ser Glu Glu Leu Arg Glu Thr Lys Arg Arg His
            210                 215                 220 gag acc cga ctg gtg gag att gac aat ggg aag cag cgt gag ttt gag       963
Glu Thr Arg Leu Val Glu Ile Asp Asn Gly Lys Gln Arg Glu Phe Glu
        225                 230                 235 agc cgg ctg gcg gat gcg ctg cag gaa ctg cgg gcc cag cat gag gac      1011
Ser Arg Leu Ala Asp Ala Leu Gln Glu Leu Arg Ala Gln His Glu Asp
    240                 245                 250 cag gtg gag cag tat aag aag gag ctg gag aag act tat tct gcc aag      1059
Gln Val Glu Gln Tyr Lys Lys Glu Leu Glu Lys Thr Tyr Ser Ala Lys
255                 260                 265                 270 ctg gac aat gcc agg cag tct gct gag agg aac agc aac ctg gtg ggg      1107
Leu Asp Asn Ala Arg Gln Ser Ala Glu Arg Asn Ser Asn Leu Val Gly
                275                 280                 285 gct gcc cac gag gag ctg cag cag tcg cgc atc cgc atc gac agc ctc      1155
Ala Ala His Glu Glu Leu Gln Gln Ser Arg Ile Arg Ile Asp Ser Leu
            290                 295                 300 tct gcc cag ctc agc cag ctc cag aag cag ctg gca gcc aag gag gcg      1203
Ser Ala Gln Leu Ser Gln Leu Gln Lys Gln Leu Ala Ala Lys Glu Ala
        305                 310                 315 aag ctt cga gac ctg gag gac tca ctg gcc cgt gag cgg gac acc agc      1251
Lys Leu Arg Asp Leu Glu Asp Ser Leu Ala Arg Glu Arg Asp Thr Ser
    320                 325                 330 cgg cgg ctg ctg gcg gaa aag gag cgg gag atg gcc gag atg cgg gca      1299
Arg Arg Leu Leu Ala Glu Lys Glu Arg Glu Met Ala Glu Met Arg Ala
335                 340                 345                 350
```

-continued

| | | |
|---|---|---|
| agg atg cag cag cag ctg gac gag tac cag gag ctt ctg gac atc aag<br>Arg Met Gln Gln Gln Leu Asp Glu Tyr Gln Glu Leu Leu Asp Ile Lys<br>355 360 365 | 1347 |
| ctg gcc ctg gac atg gag atc cac gcc tac cgc aag ctc ttg gag ggc<br>Leu Ala Leu Asp Met Glu Ile His Ala Tyr Arg Lys Leu Leu Glu Gly<br>370 375 380 | 1395 |
| gag gag gag agg cta cgc ctg tcc ccc agc cct acc tcg cag cgc agc<br>Glu Glu Glu Arg Leu Arg Leu Ser Pro Ser Pro Thr Ser Gln Arg Ser<br>385 390 395 | 1443 |
| cgt ggc cgt gct tcc tct cac tca tcc cag aca cag ggt ggg ggc agc<br>Arg Gly Arg Ala Ser Ser His Ser Ser Gln Thr Gln Gly Gly Gly Ser<br>400 405 410 | 1491 |
| gtc acc aaa aag cgc aaa ctg gag tcc act gag agc cgc agc agc ttc<br>Val Thr Lys Lys Arg Lys Leu Glu Ser Thr Glu Ser Arg Ser Ser Phe<br>415 420 425 430 | 1539 |
| tca cag cac gca cgc act agc ggg cgc gtg gcc gtg gag gag gtg gat<br>Ser Gln His Ala Arg Thr Ser Gly Arg Val Ala Val Glu Glu Val Asp<br>435 440 445 | 1587 |
| gag gag ggc aag ttt gtc cgg ctg cgc aac aag tcc aat gag gac cag<br>Glu Glu Gly Lys Phe Val Arg Leu Arg Asn Lys Ser Asn Glu Asp Gln<br>450 455 460 | 1635 |
| tcc atg ggc aat tgg cag atc aag cgc cag aat gga gat gat ccc ttg<br>Ser Met Gly Asn Trp Gln Ile Lys Arg Gln Asn Gly Asp Asp Pro Leu<br>465 470 475 | 1683 |
| ctg act tac cgg ttc cca cca aag ttc acc ctg aag gct ggg cag gtg<br>Leu Thr Tyr Arg Phe Pro Pro Lys Phe Thr Leu Lys Ala Gly Gln Val<br>480 485 490 | 1731 |
| gtg acg atc tgg gct gca gga gct ggg gcc acc cac agc ccc cct acc<br>Val Thr Ile Trp Ala Ala Gly Ala Gly Ala Thr His Ser Pro Pro Thr<br>495 500 505 510 | 1779 |
| gac ctg gtg tgg aag gca cag aac acc tgg ggc tgc ggg aac agc ctg<br>Asp Leu Val Trp Lys Ala Gln Asn Thr Trp Gly Cys Gly Asn Ser Leu<br>515 520 525 | 1827 |
| cgt acg gct ctc atc aac tcc act ggg gaa gaa gtg gcc atg cgc aag<br>Arg Thr Ala Leu Ile Asn Ser Thr Gly Glu Glu Val Ala Met Arg Lys<br>530 535 540 | 1875 |
| ctg gtg cgc tca gtg act gtg gtt gag gac gac gag gat gag gat gga<br>Leu Val Arg Ser Val Thr Val Val Glu Asp Asp Glu Asp Glu Asp Gly<br>545 550 555 | 1923 |
| gat gac ctg ctc cat cac cac cac ggc tcc cac tgc agc agc tcg ggg<br>Asp Asp Leu Leu His His His His Gly Ser His Cys Ser Ser Ser Gly<br>560 565 570 | 1971 |
| gac ccc gct gag tac aac ctg cgc tcg cgc acc gtg ctg tgc ggg acc<br>Asp Pro Ala Glu Tyr Asn Leu Arg Ser Arg Thr Val Leu Cys Gly Thr<br>575 580 585 590 | 2019 |
| tgc ggg cag cct gcc gac aag gca tct gcc agc ggc tca gga gcc cag<br>Cys Gly Gln Pro Ala Asp Lys Ala Ser Ala Ser Gly Ser Gly Ala Gln<br>595 600 605 | 2067 |
| gtg ggc gga ccc atc tcc tct ggc tct tct gcc tcc agt gtc acg gtc<br>Val Gly Gly Pro Ile Ser Ser Gly Ser Ser Ala Ser Ser Val Thr Val<br>610 615 620 | 2115 |
| act cgc agc tac cgc agt gtg ggg ggc agt ggg ggt ggc agc ttc ggg<br>Thr Arg Ser Tyr Arg Ser Val Gly Gly Ser Gly Gly Gly Ser Phe Gly<br>625 630 635 | 2163 |
| gac aat ctg gtc acc cgc tcc tac ctc ctg ggc aac tcc agc ccc cga<br>Asp Asn Leu Val Thr Arg Ser Tyr Leu Leu Gly Asn Ser Ser Pro Arg<br>640 645 650 | 2211 |
| acc cag agc ccc cag aac tgc agc atc atg taa tctgggacct gccaggcagg<br>Thr Gln Ser Pro Gln Asn Cys Ser Ile Met<br>655 660 | 2264 |

```
ggtgggggtg gaggcttcct gcgtcctcct cacctcatgc ccaccccctg ccctgcacgt    2324
catgggaggg ggcttgaagc caaagaaaaa taaccctttg gttttttct tctgtatttt     2384 tttttctaag agaagttatt ttctacagtg gttttatact gaaggaaaaa cacaagcaaa    2444
aaaaaaaaaa agcatctatc tcatctatct caatcctaat ttctcctccc ttccttttcc    2504
ctgcttccag gaaactccac atctgcctta aaaccaaaga gggcttcctc tagaagccaa    2564
gggaaagggg tgcttttata gaggctagct tctgcttttc tgccctggct gctgccccca    2624
ccccggggac cctgtgacat ggtgcctgag aggcaggcat agaggcttct ccgccagcct    2684
cctctggacg gcaggctcac tgccaggcca gcctccgaga gggagagaga gagagagagg    2744
acagcttgag ccgggcccct gggcttggcc tgctgtgatt ccactacacc tggctgaggt    2804
tcctctgcct gccccgcccc cagtccccac ccctgccccc agcccgggg tgagtccatt     2864 ctcccaggta ccagctgcgc ttgcttttct gtatttatt tagacaagag atgggaatga     2924
ggtgggaggt ggaagaaggg agaagaaagg tgagtttgag ctgccttccc tagctttaga    2984
ccctgggtgg gctctgtgca gtcactggag gttgaagcca agtggggtgc tgggaggagg    3044
gagagggagg tcactggaaa ggggagagcc tgctggcacc caccgtggag gaggaaggca    3104 agaggggggtg gaggggtgtg gcagtggttt tggcaaacgc taaagagccc ttgcctcccc   3164
atttcccatc tgcaccccctt ctctcctccc caaatcaata cactagttgt ttctacccct   3224
ggcaaaaaaa aaaaa                                                     3239

<210> SEQ ID NO 2
<211> LENGTH: 664
<212> TYPE: PRT
<213> ORGANISM: Homo sapiens

<400> SEQUENCE: 2

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190
```

```
Ala Glu Asn Arg Leu Gln Thr Met Lys Glu Leu Asp Phe Gln Lys
            195                 200                 205
Asn Ile Tyr Ser Glu Glu Leu Arg Glu Thr Lys Arg Arg His Glu Thr
210                 215                 220
Arg Leu Val Glu Ile Asp Asn Gly Lys Gln Arg Glu Phe Glu Ser Arg
225                 230                 235                 240
Leu Ala Asp Ala Leu Gln Glu Leu Arg Ala Gln His Glu Asp Gln Val
            245                 250                 255
Glu Gln Tyr Lys Lys Glu Leu Glu Lys Thr Tyr Ser Ala Lys Leu Asp
            260                 265                 270
Asn Ala Arg Gln Ser Ala Glu Arg Asn Ser Asn Leu Val Gly Ala Ala
            275                 280                 285
His Glu Glu Leu Gln Gln Ser Arg Ile Arg Ile Asp Ser Leu Ser Ala
            290                 295                 300
Gln Leu Ser Gln Leu Gln Lys Gln Leu Ala Ala Lys Glu Ala Lys Leu
305                 310                 315                 320
Arg Asp Leu Glu Asp Ser Leu Ala Arg Glu Arg Asp Thr Ser Arg Arg
            325                 330                 335
Leu Leu Ala Glu Lys Glu Arg Glu Met Ala Glu Met Arg Ala Arg Met
            340                 345                 350
Gln Gln Gln Leu Asp Glu Tyr Gln Glu Leu Leu Asp Ile Lys Leu Ala
            355                 360                 365
Leu Asp Met Glu Ile His Ala Tyr Arg Lys Leu Leu Glu Gly Glu Glu
            370                 375                 380
Glu Arg Leu Arg Leu Ser Pro Ser Pro Thr Ser Gln Arg Ser Arg Gly
385                 390                 395                 400
Arg Ala Ser Ser His Ser Ser Gln Thr Gln Gly Gly Gly Ser Val Thr
            405                 410                 415
Lys Lys Arg Lys Leu Glu Ser Thr Glu Ser Arg Ser Ser Phe Ser Gln
            420                 425                 430
His Ala Arg Thr Ser Gly Arg Val Ala Val Glu Glu Val Asp Glu Glu
            435                 440                 445
Gly Lys Phe Val Arg Leu Arg Asn Lys Ser Asn Glu Asp Gln Ser Met
450                 455                 460
Gly Asn Trp Gln Ile Lys Arg Gln Asn Gly Asp Asp Pro Leu Leu Thr
465                 470                 475                 480
Tyr Arg Phe Pro Pro Lys Phe Thr Leu Lys Ala Gly Gln Val Val Thr
            485                 490                 495
Ile Trp Ala Ala Gly Ala Gly Ala Thr His Ser Pro Thr Asp Leu
            500                 505                 510
Val Trp Lys Ala Gln Asn Thr Trp Gly Cys Gly Asn Ser Leu Arg Thr
            515                 520                 525
Ala Leu Ile Asn Ser Thr Gly Glu Glu Val Ala Met Arg Lys Leu Val
            530                 535                 540
Arg Ser Val Thr Val Val Glu Asp Asp Glu Asp Glu Asp Gly Asp Asp
545                 550                 555                 560
Leu Leu His His His His Gly Ser His Cys Ser Ser Ser Gly Asp Pro
            565                 570                 575
Ala Glu Tyr Asn Leu Arg Ser Arg Thr Val Leu Cys Gly Thr Cys Gly
            580                 585                 590
Gln Pro Ala Asp Lys Ala Ser Ala Ser Gly Ser Gly Ala Gln Val Gly
            595                 600                 605
Gly Pro Ile Ser Ser Gly Ser Ser Ala Ser Ser Val Thr Val Thr Arg
```

```
              610                 615                 620
Ser Tyr Arg Ser Val Gly Gly Ser Gly Gly Gly Ser Phe Gly Asp Asn
625                 630                 635                 640

Leu Val Thr Arg Ser Tyr Leu Leu Gly Asn Ser Ser Pro Arg Thr Gln
                    645                 650                 655

Ser Pro Gln Asn Cys Ser Ile Met
            660

<210> SEQ ID NO 3
<211> LENGTH: 2077
<212> TYPE: DNA
<213> ORGANISM: Homo sapiens
<220> FEATURE:
<221> NAME/KEY: CDS
<222> LOCATION: (250)..(1968)
<223> OTHER INFORMATION: Lamin isoform C is encoded by transcript
      variant 2.  NCBI Reference Sequence: NM_005572.3

<400> SEQUENCE: 3
aggaggacct attagagcct tgccccggc gtcggtgact cagtgttcgc gggagcgccg        60
cacctacacc agccaaccca gatcccgagg tccgacagcg cccggcccag atccccacgc      120
ctgccaggag caagccgaga gccagccggc cggcgcactc cgactccgag cagtctctgt      180
ccttcgaccc gagccccgcg ccctttccgg gacccctgcc ccgcgggcag cgctgccaac      240 ctgccggcc atg gag acc ccg tcc cag cgg cgc gcc acc cgc agc ggg gcg      291
           Met Glu Thr Pro Ser Gln Arg Arg Ala Thr Arg Ser Gly Ala
           1               5                   10 cag gcc agc tcc act ccg ctg tcg ccc acc cgc atc acc cgg ctg cag        339
Gln Ala Ser Ser Thr Pro Leu Ser Pro Thr Arg Ile Thr Arg Leu Gln
15                  20                  25                  30 gag aag gag gac ctg cag gag ctc aat gat cgc ttg gcg gtc tac atc        387
Glu Lys Glu Asp Leu Gln Glu Leu Asn Asp Arg Leu Ala Val Tyr Ile
                35                  40                  45 gac cgt gtg cgc tcg ctg gaa acg gag aac gca ggg ctg cgc ctt cgc        435
Asp Arg Val Arg Ser Leu Glu Thr Glu Asn Ala Gly Leu Arg Leu Arg
            50                  55                  60 atc acc gag tct gaa gag gtg gtc agc cgc gag gtg tcc ggc atc aag        483
Ile Thr Glu Ser Glu Glu Val Val Ser Arg Glu Val Ser Gly Ile Lys
65                  70                  75 gcc gcc tac gag gcc gag ctc ggg gat gcc cgc aag acc ctt gac tca        531
Ala Ala Tyr Glu Ala Glu Leu Gly Asp Ala Arg Lys Thr Leu Asp Ser
            80                  85                  90 gta gcc aag gag cgc gcc cgc ctg cag ctg gag ctg agc aaa gtg cgt        579
Val Ala Lys Glu Arg Ala Arg Leu Gln Leu Glu Leu Ser Lys Val Arg
95                  100                 105                 110 gag gag ttt aag gag ctg aaa gcg cgc aat acc aag aag gag ggt gac        627
Glu Glu Phe Lys Glu Leu Lys Ala Arg Asn Thr Lys Lys Glu Gly Asp
                115                 120                 125 ctg ata gct gct cag gct cgg ctg aag gac ctg gag gct ctg ctg aac        675
Leu Ile Ala Ala Gln Ala Arg Leu Lys Asp Leu Glu Ala Leu Leu Asn
            130                 135                 140 tcc aag gag gcc gca ctg agc act gct ctc agt gag aag cgc acg ctg        723
Ser Lys Glu Ala Ala Leu Ser Thr Ala Leu Ser Glu Lys Arg Thr Leu
        145                 150                 155 gag ggc gag ctg cat gat ctg cgg ggc cag gtg gcc aag ctt gag gca        771
Glu Gly Glu Leu His Asp Leu Arg Gly Gln Val Ala Lys Leu Glu Ala
        160                 165                 170 gcc cta ggt gag gcc aag aag caa ctt cag gat gag atg ctg cgg cgg        819
Ala Leu Gly Glu Ala Lys Lys Gln Leu Gln Asp Glu Met Leu Arg Arg
175                 180                 185                 190
```

```
gtg gat gct gag aac agg ctg cag acc atg aag gag gaa ctg gac ttc      867
Val Asp Ala Glu Asn Arg Leu Gln Thr Met Lys Glu Glu Leu Asp Phe
            195                 200                 205 cag aag aac atc tac agt gag gag ctg cgt gag acc aag cgc cgt cat      915
Gln Lys Asn Ile Tyr Ser Glu Glu Leu Arg Glu Thr Lys Arg Arg His
            210                 215                 220 gag acc cga ctg gtg gag att gac aat ggg aag cag cgt gag ttt gag      963
Glu Thr Arg Leu Val Glu Ile Asp Asn Gly Lys Gln Arg Glu Phe Glu
            225                 230                 235 agc cgg ctg gcg gat gcg ctg cag gaa ctg cgg gcc cag cat gag gac     1011
Ser Arg Leu Ala Asp Ala Leu Gln Glu Leu Arg Ala Gln His Glu Asp
            240                 245                 250 cag gtg gag cag tat aag aag gag ctg gag aag act tat tct gcc aag     1059
Gln Val Glu Gln Tyr Lys Lys Glu Leu Glu Lys Thr Tyr Ser Ala Lys
255                 260                 265                 270 ctg gac aat gcc agg cag tct gct gag agg aac agc aac ctg gtg ggg     1107
Leu Asp Asn Ala Arg Gln Ser Ala Glu Arg Asn Ser Asn Leu Val Gly
                275                 280                 285 gct gcc cac gag gag ctg cag cag tcg cgc atc cgc atc gac agc ctc     1155
Ala Ala His Glu Glu Leu Gln Gln Ser Arg Ile Arg Ile Asp Ser Leu
            290                 295                 300 tct gcc cag ctc agc cag ctc cag aag cag ctg gca gcc aag gag gcg     1203
Ser Ala Gln Leu Ser Gln Leu Gln Lys Gln Leu Ala Ala Lys Glu Ala
            305                 310                 315 aag ctt cga gac ctg gag gac tca ctg gcc cgt gag cgg gac acc agc     1251
Lys Leu Arg Asp Leu Glu Asp Ser Leu Ala Arg Glu Arg Asp Thr Ser
            320                 325                 330 cgg cgg ctg ctg gcg gaa aag gag cgg gag atg gcc gag atg cgg gca     1299
Arg Arg Leu Leu Ala Glu Lys Glu Arg Glu Met Ala Glu Met Arg Ala
335                 340                 345                 350 agg atg cag cag cag ctg gac gag tac cag gag ctt ctg gac atc aag     1347
Arg Met Gln Gln Gln Leu Asp Glu Tyr Gln Glu Leu Leu Asp Ile Lys
                355                 360                 365 ctg gcc ctg gac atg gag atc cac gcc tac cgc aag ctc ttg gag ggc     1395
Leu Ala Leu Asp Met Glu Ile His Ala Tyr Arg Lys Leu Leu Glu Gly
            370                 375                 380 gag gag gag agg cta cgc ctg tcc ccc agc cct acc tcg cag cgc agc     1443
Glu Glu Glu Arg Leu Arg Leu Ser Pro Ser Pro Thr Ser Gln Arg Ser
            385                 390                 395 cgt ggc cgt gct tcc tct cac tca tcc cag aca cag ggt ggg ggc agc     1491
Arg Gly Arg Ala Ser Ser His Ser Ser Gln Thr Gln Gly Gly Gly Ser
            400                 405                 410 gtc acc aaa aag cgc aaa ctg gag tcc act gag agc cgc agc agc ttc     1539
Val Thr Lys Lys Arg Lys Leu Glu Ser Thr Glu Ser Arg Ser Ser Phe
415                 420                 425                 430 tca cag cac gca cgc act agc ggg cgt gtg gcc gtg gag gag gtg gat     1587
Ser Gln His Ala Arg Thr Ser Gly Arg Val Ala Val Glu Glu Val Asp
                435                 440                 445 gag gag ggc aag ttt gtc cgg ctg cgc aac aag tcc aat gag gac cag     1635
Glu Glu Gly Lys Phe Val Arg Leu Arg Asn Lys Ser Asn Glu Asp Gln
            450                 455                 460 tcc atg ggc aat tgg cag atc aag cgc cag aat gga gat gat ccc ttg     1683
Ser Met Gly Asn Trp Gln Ile Lys Arg Gln Asn Gly Asp Asp Pro Leu
            465                 470                 475 ctg act tac cgg ttc cca cca aag ttc acc ctg aag gct ggg cag gtg     1731
Leu Thr Tyr Arg Phe Pro Pro Lys Phe Thr Leu Lys Ala Gly Gln Val
            480                 485                 490 gtg acg atc tgg gct gca gga gct ggg gcc acc cac agc ccc cct acc     1779
Val Thr Ile Trp Ala Ala Gly Ala Gly Ala Thr His Ser Pro Pro Thr
```

```
                495                 500                 505                 510
gac ctg gtg tgg aag gca cag aac acc tgg ggc tgc ggg aac agc ctg        1827
Asp Leu Val Trp Lys Ala Gln Asn Thr Trp Gly Cys Gly Asn Ser Leu
                    515                 520                 525 cgt acg gct ctc atc aac tcc act ggg gaa gaa gtg gcc atg cgc aag        1875
Arg Thr Ala Leu Ile Asn Ser Thr Gly Glu Glu Val Ala Met Arg Lys
                530                 535                 540 ctg gtg cgc tca gtg act gtg gtt gag gac gac gag gat gag gat gga        1923
Leu Val Arg Ser Val Thr Val Val Glu Asp Asp Glu Asp Glu Asp Gly
            545                 550                 555 gat gac ctg ctc cat cac cac cac gtg agt ggt agc cgc cgc tga            1968
Asp Asp Leu Leu His His His His Val Ser Gly Ser Arg Arg
        560                 565                 570 ggccgagcct gcactggggc cacccagcca ggcctggggg cagcctctcc ccagcctccc      2028
cgtgccaaaa atcttttcat taagaatgtg tttggaactt taaaaaaaa                  2077

<210> SEQ ID NO 4
<211> LENGTH: 572
<212> TYPE: PRT
<213> ORGANISM: Homo sapiens

<400> SEQUENCE: 4

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
                20                  25                  30

Glu Asp Leu Gln Glu Leu Asn Asp Arg Leu Ala Val Tyr Ile Asp Arg
            35                  40                  45

Val Arg Ser Leu Glu Thr Glu Asn Ala Gly Leu Arg Leu Arg Ile Thr
        50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
```

```
            260                 265                 270
Asn Ala Arg Gln Ser Ala Glu Arg Asn Ser Asn Leu Val Gly Ala Ala
            275                 280                 285

His Glu Glu Leu Gln Gln Ser Arg Ile Arg Ile Asp Ser Leu Ser Ala
            290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
            355                 360                 365

Leu Asp Met Glu Ile His Ala Tyr Arg Lys Leu Leu Glu Gly Glu Glu
            370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
                420                 425                 430

His Ala Arg Thr Ser Gly Arg Val Ala Val Glu Glu Val Asp Glu Glu
            435                 440                 445

Gly Lys Phe Val Arg Leu Arg Asn Lys Ser Asn Glu Asp Gln Ser Met
            450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
                500                 505                 510

Val Trp Lys Ala Gln Asn Thr Trp Gly Cys Gly Asn Ser Leu Arg Thr
            515                 520                 525

Ala Leu Ile Asn Ser Thr Gly Glu Glu Val Ala Met Arg Lys Leu Val
            530                 535                 540

Arg Ser Val Thr Val Val Glu Asp Asp Glu Asp Glu Asp Gly Asp Asp
545                 550                 555                 560

Leu Leu His His His His Val Ser Gly Ser Arg Arg
                565                 570

<210> SEQ ID NO 5
<211> LENGTH: 3149
<212> TYPE: DNA
<213> ORGANISM: Homo sapiens
<220> FEATURE:
<221> NAME/KEY: CDS
<222> LOCATION: (250)..(2154)
<223> OTHER INFORMATION: Lamin isoform A-delta10 is encoded by
      transcript variant 3. NCBI Reference Sequence: NM_170708.3.

<400> SEQUENCE: 5
aggaggacct attagagcct tgccccggc gtcggtgact cagtgttcgc gggagcgccg      60
cacctacacc agccaaccca gatcccgagg tccgacagcg cccggcccag atccccacgc    120
ctgccaggag caagccgaga gccagccggc cggcgcactc cgactccgag cagtctctgt    180
ccttcgaccc gagccccgcg cccttccgg gaccctgcc ccgcgggcag cgctgccaac      240
```

```
ctgccggcc atg gag acc ccg tcc cag cgg cgc gcc acc cgc agc ggg gcg        291
          Met Glu Thr Pro Ser Gln Arg Arg Ala Thr Arg Ser Gly Ala
          1               5                   10 cag gcc agc tcc act ccg ctg tcg ccc acc cgc atc acc cgg ctg cag          339
Gln Ala Ser Ser Thr Pro Leu Ser Pro Thr Arg Ile Thr Arg Leu Gln
15              20                  25                  30 gag aag gag gac ctg cag gag ctc aat gat cgc ttg gcg gtc tac atc          387
Glu Lys Glu Asp Leu Gln Glu Leu Asn Asp Arg Leu Ala Val Tyr Ile
                35                  40                  45 gac cgt gtg cgc tcg ctg gaa acg gag aac gca ggg ctg cgc ctt cgc          435
Asp Arg Val Arg Ser Leu Glu Thr Glu Asn Ala Gly Leu Arg Leu Arg
            50                  55                  60 atc acc gag tct gaa gag gtg gtc agc cgc gag gtg tcc ggc atc aag          483
Ile Thr Glu Ser Glu Glu Val Val Ser Arg Glu Val Ser Gly Ile Lys
65                  70                  75 gcc gcc tac gag gcc gag ctc ggg gat gcc cgc aag acc ctt gac tca          531
Ala Ala Tyr Glu Ala Glu Leu Gly Asp Ala Arg Lys Thr Leu Asp Ser
        80                  85                  90 gta gcc aag gag cgc gcc cgc ctg cag ctg gag ctg agc aaa gtg cgt          579
Val Ala Lys Glu Arg Ala Arg Leu Gln Leu Glu Leu Ser Lys Val Arg
95              100                 105                 110 gag gag ttt aag gag ctg aaa gcg cgc aat acc aag aag gag ggt gac          627
Glu Glu Phe Lys Glu Leu Lys Ala Arg Asn Thr Lys Lys Glu Gly Asp
                115                 120                 125 ctg ata gct gct cag gct cgg ctg aag gac ctg gag gct ctg ctg aac          675
Leu Ile Ala Ala Gln Ala Arg Leu Lys Asp Leu Glu Ala Leu Leu Asn
            130                 135                 140 tcc aag gag gcc gca ctg agc act gct ctc agt gag aag cgc acg ctg          723
Ser Lys Glu Ala Ala Leu Ser Thr Ala Leu Ser Glu Lys Arg Thr Leu
145                 150                 155 gag ggc gag ctg cat gat ctg cgg ggc cag gtg gcc aag ctt gag gca          771
Glu Gly Glu Leu His Asp Leu Arg Gly Gln Val Ala Lys Leu Glu Ala
        160                 165                 170 gcc cta ggt gag gcc aag aag caa ctt cag gat gag atg ctg cgg cgg          819
Ala Leu Gly Glu Ala Lys Lys Gln Leu Gln Asp Glu Met Leu Arg Arg
175                 180                 185                 190 gtg gat gct gag aac agg ctg cag acc atg aag gag gaa ctg gac ttc          867
Val Asp Ala Glu Asn Arg Leu Gln Thr Met Lys Glu Glu Leu Asp Phe
                195                 200                 205 cag aag aac atc tac agt gag gag ctg cgt gag acc aag cgc cgt cat          915
Gln Lys Asn Ile Tyr Ser Glu Glu Leu Arg Glu Thr Lys Arg Arg His
            210                 215                 220 gag acc cga ctg gtg gag att gac aat ggg aag cag cgt gag ttt gag          963
Glu Thr Arg Leu Val Glu Ile Asp Asn Gly Lys Gln Arg Glu Phe Glu
225                 230                 235 agc cgg ctg gcg gat gcg ctg cag gaa ctg cgg gcc cag cat gag gac         1011
Ser Arg Leu Ala Asp Ala Leu Gln Glu Leu Arg Ala Gln His Glu Asp
        240                 245                 250 cag gtg gag cag tat aag aag gag ctg gag aag act tat tct gcc aag         1059
Gln Val Glu Gln Tyr Lys Lys Glu Leu Glu Lys Thr Tyr Ser Ala Lys
255                 260                 265                 270 ctg gac aat gcc agg cag tct gct gag agg aac agc aac ctg gtg ggg         1107
Leu Asp Asn Ala Arg Gln Ser Ala Glu Arg Asn Ser Asn Leu Val Gly
                275                 280                 285 gct gcc cac gag gag ctg cag cag tcg cgc atc cgc atc gac agc ctc         1155
Ala Ala His Glu Glu Leu Gln Gln Ser Arg Ile Arg Ile Asp Ser Leu
            290                 295                 300 tct gcc cag ctc agc cag ctc cag aag cag ctg gca gcc aag gag gcg         1203
Ser Ala Gln Leu Ser Gln Leu Gln Lys Gln Leu Ala Ala Lys Glu Ala
```

-continued

```
              305                 310                 315
aag ctt cga gac ctg gag gac tca ctg gcc cgt gag cgg gac acc agc      1251
Lys Leu Arg Asp Leu Glu Asp Ser Leu Ala Arg Glu Arg Asp Thr Ser
    320                 325                 330 cgg cgg ctg ctg gcg gaa aag gag cgg gag atg gcc gag atg cgg gca      1299
Arg Arg Leu Leu Ala Glu Lys Glu Arg Glu Met Ala Glu Met Arg Ala
335                 340                 345                 350 agg atg cag cag cag ctg gac gag tac cag gag ctt ctg gac atc aag      1347
Arg Met Gln Gln Gln Leu Asp Glu Tyr Gln Glu Leu Leu Asp Ile Lys
                355                 360                 365 ctg gcc ctg gac atg gag atc cac gcc tac cgc aag ctc ttg gag ggc      1395
Leu Ala Leu Asp Met Glu Ile His Ala Tyr Arg Lys Leu Leu Glu Gly
            370                 375                 380 gag gag gag agg cta cgc ctg tcc ccc agc cct acc tcg cag cgc agc      1443
Glu Glu Glu Arg Leu Arg Leu Ser Pro Ser Pro Thr Ser Gln Arg Ser
385                 390                 395 cgt ggc cgt gct tcc tct cac tca tcc cag aca cag ggt ggg ggc agc      1491
Arg Gly Arg Ala Ser Ser His Ser Ser Gln Thr Gln Gly Gly Gly Ser
    400                 405                 410 gtc acc aaa aag cgc aaa ctg gag tcc act gag agc cgc agc agc ttc      1539
Val Thr Lys Lys Arg Lys Leu Glu Ser Thr Glu Ser Arg Ser Ser Phe
415                 420                 425                 430 tca cag cac gca cgc act agc ggg cgc gtg gcc gtg gag gag gtg gat      1587
Ser Gln His Ala Arg Thr Ser Gly Arg Val Ala Val Glu Glu Val Asp
                435                 440                 445 gag gag ggc aag ttt gtc cgg ctg cgc aac aag tcc aat gag gac cag      1635
Glu Glu Gly Lys Phe Val Arg Leu Arg Asn Lys Ser Asn Glu Asp Gln
            450                 455                 460 tcc atg ggc aat tgg cag atc aag cgc cag aat gga gat gat ccc ttg      1683
Ser Met Gly Asn Trp Gln Ile Lys Arg Gln Asn Gly Asp Asp Pro Leu
465                 470                 475 ctg act tac cgg ttc cca cca aag ttc acc ctg aag gct ggg cag gtg      1731
Leu Thr Tyr Arg Phe Pro Pro Lys Phe Thr Leu Lys Ala Gly Gln Val
    480                 485                 490 gtg acg atc tgg gct gca gga gct ggg gcc acc cac agc ccc cct acc      1779
Val Thr Ile Trp Ala Ala Gly Ala Gly Ala Thr His Ser Pro Pro Thr
495                 500                 505                 510 gac ctg gtg tgg aag gca cag aac acc tgg ggc tgc ggg aac agc ctg      1827
Asp Leu Val Trp Lys Ala Gln Asn Thr Trp Gly Cys Gly Asn Ser Leu
                515                 520                 525 cgt acg gct ctc atc aac tcc act ggg gaa ggc tcc cac tgc agc agc      1875
Arg Thr Ala Leu Ile Asn Ser Thr Gly Glu Gly Ser His Cys Ser Ser
            530                 535                 540 tcg ggg gac ccc gct gag tac aac ctg cgc tcg cgc acc gtg ctg tgc      1923
Ser Gly Asp Pro Ala Glu Tyr Asn Leu Arg Ser Arg Thr Val Leu Cys
545                 550                 555 ggg acc tgc ggg cag cct gcc gac aag gca tct gcc agc ggc tca gga      1971
Gly Thr Cys Gly Gln Pro Ala Asp Lys Ala Ser Ala Ser Gly Ser Gly
    560                 565                 570 gcc cag gtg ggc gga ccc atc tcc tct ggc tct tct gcc tcc agt gtc      2019
Ala Gln Val Gly Gly Pro Ile Ser Ser Gly Ser Ser Ala Ser Ser Val
575                 580                 585                 590 acg gtc act cgc agc tac cgc agt gtg ggg ggc agt ggg ggt ggc agc      2067
Thr Val Thr Arg Ser Tyr Arg Ser Val Gly Gly Ser Gly Gly Gly Ser
                595                 600                 605 ttc ggg gac aat ctg gtc acc cgc tcc tac ctc ctg ggc aac tcc agc      2115
Phe Gly Asp Asn Leu Val Thr Arg Ser Tyr Leu Leu Gly Asn Ser Ser
            610                 615                 620 ccc cga acc cag agc ccc cag aac tgc agc atc atg taa tctgggacct      2164
Pro Arg Thr Gln Ser Pro Gln Asn Cys Ser Ile Met
```

-continued

Pro Arg Thr Gln Ser Pro Gln Asn Cys Ser Ile Met
            625                 630

```
gccaggcagg ggtggggtg gaggcttcct gcgtcctcct cacctcatgc ccaccccctg     2224
ccctgcacgt catgggaggg ggcttgaagc caaagaaaaa taacccttg gttttttct     2284 tctgtatttt ttttctaag agaagttatt ttcacagtg gttttatact gaaggaaaaa     2344
cacaagcaaa aaaaaaaaa agcatctatc tcatctatct caatcctaat ttctcctccc     2404
ttccttttcc ctgcttccag gaaactccac atctgcctta aaaccaaaga gggcttcctc     2464
tagaagccaa gggaaagggg tgcttttata gaggctagct tctgcttttc tgccctggct     2524
gctgccccca ccccggggac cctgtgacat ggtgcctgag aggcaggcat agaggcttct     2584
ccgccagcct cctctggacg gcaggctcac tgccaggcca gcctccgaga gggagagaga     2644
gagagagagg acagcttgag ccgggcccct gggcttggcc tgctgtgatt ccactacacc     2704
tggctgaggt tcctctgcct gccccgcccc cagtccccac ccctgccccc agccccgggg     2764
tgagtccatt ctcccaggta ccagctgcgc ttgcttttct gtattttatt tagacaagag     2824
atgggaatga ggtgggaggt ggaagaaggg agaagaaagg tgagtttgag ctgccttccc     2884
tagctttaga ccctgggtgg gctctgtgca gtcactggag gttgaagcca agtggggtgc     2944
tgggaggagg gagagggagg tcactggaaa ggggagagcc tgctggcacc caccgtggag     3004
gaggaaggca agaggggtg gagggtgtg gcagtggttt tggcaaacgc taaagagccc     3064
ttgcctcccc atttcccatc tgcacccctt ctctcctccc caaatcaata cactagttgt     3124 ttctaccct ggcaaaaaaa aaaaa                                            3149
```

<210> SEQ ID NO 6
<211> LENGTH: 634
<212> TYPE: PRT
<213> ORGANISM: Homo sapiens

<400> SEQUENCE: 6

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp

```
            180             185             190
Ala Glu Asn Arg Leu Gln Thr Met Lys Glu Leu Asp Phe Gln Lys
            195             200             205
Asn Ile Tyr Ser Glu Glu Leu Arg Glu Thr Lys Arg Arg His Glu Thr
            210             215             220
Arg Leu Val Glu Ile Asp Asn Gly Lys Gln Arg Glu Phe Glu Ser Arg
225             230             235             240
Leu Ala Asp Ala Leu Gln Glu Leu Arg Ala Gln His Glu Asp Gln Val
            245             250             255
Glu Gln Tyr Lys Lys Glu Leu Glu Lys Thr Tyr Ser Ala Lys Leu Asp
            260             265             270
Asn Ala Arg Gln Ser Ala Glu Arg Asn Ser Asn Leu Val Gly Ala Ala
            275             280             285
His Glu Glu Leu Gln Gln Ser Arg Ile Arg Ile Asp Ser Leu Ser Ala
            290             295             300
Gln Leu Ser Gln Leu Gln Lys Gln Leu Ala Ala Lys Glu Ala Lys Leu
305             310             315             320
Arg Asp Leu Glu Asp Ser Leu Ala Arg Glu Arg Asp Thr Ser Arg Arg
            325             330             335
Leu Leu Ala Glu Lys Glu Arg Glu Met Ala Glu Met Arg Ala Arg Met
            340             345             350
Gln Gln Gln Leu Asp Glu Tyr Gln Glu Leu Leu Asp Ile Lys Leu Ala
            355             360             365
Leu Asp Met Glu Ile His Ala Tyr Arg Lys Leu Leu Glu Gly Glu Glu
            370             375             380
Glu Arg Leu Arg Leu Ser Pro Ser Pro Thr Ser Gln Arg Ser Arg Gly
385             390             395             400
Arg Ala Ser Ser His Ser Ser Gln Thr Gln Gly Gly Gly Ser Val Thr
            405             410             415
Lys Lys Arg Lys Leu Glu Ser Thr Glu Ser Arg Ser Ser Phe Ser Gln
            420             425             430
His Ala Arg Thr Ser Gly Arg Val Ala Val Glu Glu Val Asp Glu Glu
            435             440             445
Gly Lys Phe Val Arg Leu Arg Asn Lys Ser Asn Glu Asp Gln Ser Met
            450             455             460
Gly Asn Trp Gln Ile Lys Arg Gln Asn Gly Asp Asp Pro Leu Leu Thr
465             470             475             480
Tyr Arg Phe Pro Pro Lys Phe Thr Leu Lys Ala Gly Gln Val Val Thr
            485             490             495
Ile Trp Ala Ala Gly Ala Gly Ala Thr His Ser Pro Pro Thr Asp Leu
            500             505             510
Val Trp Lys Ala Gln Asn Thr Trp Gly Cys Gly Asn Ser Leu Arg Thr
            515             520             525
Ala Leu Ile Asn Ser Thr Gly Glu Gly Ser His Cys Ser Ser Ser Gly
            530             535             540
Asp Pro Ala Glu Tyr Asn Leu Arg Ser Arg Thr Val Leu Cys Gly Thr
545             550             555             560
Cys Gly Gln Pro Ala Asp Lys Ala Ser Ala Ser Gly Ser Gly Ala Gln
            565             570             575
Val Gly Gly Pro Ile Ser Ser Gly Ser Ser Ala Ser Ser Val Thr Val
            580             585             590
Thr Arg Ser Tyr Arg Ser Val Gly Gly Ser Gly Gly Gly Ser Phe Gly
            595             600             605
```

```
Asp Asn Leu Val Thr Arg Ser Tyr Leu Leu Gly Asn Ser Ser Pro Arg
    610                 615                 620

Thr Gln Ser Pro Gln Asn Cys Ser Ile Met
625                 630

<210> SEQ ID NO 7
<211> LENGTH: 3089
<212> TYPE: DNA
<213> ORGANISM: Homo sapiens
<220> FEATURE:
<221> NAME/KEY: CDS
<222> LOCATION: (250)..(2094)
<223> OTHER INFORMATION: Lamin isoform A-delta50 is encoded by
      transcript variant 7. NCBI Reference Sequence: NM_001282626.1.

<400> SEQUENCE: 7
aggaggacct attagagcct tgccccggc gtcggtgact cagtgttcgc gggagcgccg      60
cacctacacc agccaaccca gatcccgagg tccgacagcg cccggcccag atccccacgc    120
ctgccaggag caagccgaga gccagccggc cggcgcactc cgactccgag cagtctctgt    180
ccttcgaccc gagccccgcg ccctttccgg gaccctgcc ccgcgggcag cgctgccaac    240 ctgccggcc atg gag acc ccg tcc cag cgg cgc gcc acc cgc agc ggg gcg    291
         Met Glu Thr Pro Ser Gln Arg Arg Ala Thr Arg Ser Gly Ala
             1               5                   10 cag gcc agc tcc act ccg ctg tcg ccc acc cgc atc acc cgg ctg cag    339
Gln Ala Ser Ser Thr Pro Leu Ser Pro Thr Arg Ile Thr Arg Leu Gln
15                  20                  25                  30 gag aag gag gac ctg cag gag ctc aat gat cgc ttg gcg gtc tac atc    387
Glu Lys Glu Asp Leu Gln Glu Leu Asn Asp Arg Leu Ala Val Tyr Ile
                35                  40                  45 gac cgt gtg cgc tcg ctg gaa acg gag aac gca ggg ctg cgc ctt cgc    435
Asp Arg Val Arg Ser Leu Glu Thr Glu Asn Ala Gly Leu Arg Leu Arg
            50                  55                  60 atc acc gag tct gaa gag gtg gtc agc cgc gag gtg tcc ggc atc aag    483
Ile Thr Glu Ser Glu Glu Val Val Ser Arg Glu Val Ser Gly Ile Lys
65                  70                  75 gcc gcc tac gag gcc gag ctc ggg gat gcc cgc aag acc ctt gac tca    531
Ala Ala Tyr Glu Ala Glu Leu Gly Asp Ala Arg Lys Thr Leu Asp Ser
            80                  85                  90 gta gcc aag gag cgc gcc cgc ctg cag ctg gag ctg agc aaa gtg cgt    579
Val Ala Lys Glu Arg Ala Arg Leu Gln Leu Glu Leu Ser Lys Val Arg
95                  100                 105                 110 gag gag ttt aag gag ctg aaa gcg cgc aat acc aag aag gag ggt gac    627
Glu Glu Phe Lys Glu Leu Lys Ala Arg Asn Thr Lys Lys Glu Gly Asp
                115                 120                 125 ctg ata gct gct cag gct cgg ctg aag gac ctg gag gct ctg ctg aac    675
Leu Ile Ala Ala Gln Ala Arg Leu Lys Asp Leu Glu Ala Leu Leu Asn
            130                 135                 140 tcc aag gag gcc gca ctg agc act gct ctc agt gag aag cgc acg ctg    723
Ser Lys Glu Ala Ala Leu Ser Thr Ala Leu Ser Glu Lys Arg Thr Leu
        145                 150                 155 gag ggc gag ctg cat gat ctg cgg ggc cag gtg gcc aag ctt gag gca    771
Glu Gly Glu Leu His Asp Leu Arg Gly Gln Val Ala Lys Leu Glu Ala
160                 165                 170 gcc cta ggt gag gcc aag aag caa ctt cag gat gag atg ctg cgg cgg    819
Ala Leu Gly Glu Ala Lys Lys Gln Leu Gln Asp Glu Met Leu Arg Arg
175                 180                 185                 190 gtg gat gct gag aac agg ctg cag acc atg aag gag gaa ctg gac ttc    867
Val Asp Ala Glu Asn Arg Leu Gln Thr Met Lys Glu Glu Leu Asp Phe
                195                 200                 205
```

-continued

| | | |
|---|---|---|
| cag aag aac atc tac agt gag gag ctg cgt gag acc aag cgc cgt cat<br>Gln Lys Asn Ile Tyr Ser Glu Glu Leu Arg Glu Thr Lys Arg Arg His<br>            210                 215                 220 | | 915 |
| gag acc cga ctg gtg gag att gac aat ggg aag cag cgt gag ttt gag<br>Glu Thr Arg Leu Val Glu Ile Asp Asn Gly Lys Gln Arg Glu Phe Glu<br>    225                 230                 235 | | 963 |
| agc cgg ctg gcg gat gcg ctg cag gaa ctg cgg gcc cag cat gag gac<br>Ser Arg Leu Ala Asp Ala Leu Gln Glu Leu Arg Ala Gln His Glu Asp<br>240                 245                 250 | | 1011 |
| cag gtg gag cag tat aag aag gag ctg gag aag act tat tct gcc aag<br>Gln Val Glu Gln Tyr Lys Lys Glu Leu Glu Lys Thr Tyr Ser Ala Lys<br>255                 260                 265                 270 | | 1059 |
| ctg gac aat gcc agg cag tct gct gag agg aac agc aac ctg gtg ggg<br>Leu Asp Asn Ala Arg Gln Ser Ala Glu Arg Asn Ser Asn Leu Val Gly<br>                275                 280                 285 | | 1107 |
| gct gcc cac gag gag ctg cag cag tcg cgc atc cgc atc gac agc ctc<br>Ala Ala His Glu Glu Leu Gln Gln Ser Arg Ile Arg Ile Asp Ser Leu<br>            290                 295                 300 | | 1155 |
| tct gcc cag ctc agc cag ctc cag aag cag ctg gca gcc aag gag gcg<br>Ser Ala Gln Leu Ser Gln Leu Gln Lys Gln Leu Ala Ala Lys Glu Ala<br>    305                 310                 315 | | 1203 |
| aag ctt cga gac ctg gag gac tca ctg gcc cgt gag cgg gac acc agc<br>Lys Leu Arg Asp Leu Glu Asp Ser Leu Ala Arg Glu Arg Asp Thr Ser<br>320                 325                 330 | | 1251 |
| cgg cgg ctg ctg gcg gaa aag gag cgg gag atg gcc gag atg cgg gca<br>Arg Arg Leu Leu Ala Glu Lys Glu Arg Glu Met Ala Glu Met Arg Ala<br>335                 340                 345                 350 | | 1299 |
| agg atg cag cag cag ctg gac gag tac cag gag ctt ctg gac atc aag<br>Arg Met Gln Gln Gln Leu Asp Glu Tyr Gln Glu Leu Leu Asp Ile Lys<br>                355                 360                 365 | | 1347 |
| ctg gcc ctg gac atg gag atc cac gcc tac cgc aag ctc ttg gag ggc<br>Leu Ala Leu Asp Met Glu Ile His Ala Tyr Arg Lys Leu Leu Glu Gly<br>            370                 375                 380 | | 1395 |
| gag gag gag agg cta cgc ctg tcc ccc agc cct acc tcg cag cgc agc<br>Glu Glu Glu Arg Leu Arg Leu Ser Pro Ser Pro Thr Ser Gln Arg Ser<br>    385                 390                 395 | | 1443 |
| cgt ggc cgt gct tcc tct cac tca tcc cag aca cag ggt ggg ggc agc<br>Arg Gly Arg Ala Ser Ser His Ser Ser Gln Thr Gln Gly Gly Gly Ser<br>400                 405                 410 | | 1491 |
| gtc acc aaa aag cgc aaa ctg gag tcc act gag agc cgc agc agc ttc<br>Val Thr Lys Lys Arg Lys Leu Glu Ser Thr Glu Ser Arg Ser Ser Phe<br>415                 420                 425                 430 | | 1539 |
| tca cag cac gca cgc act agc ggg cgc gtg gcc gtg gag gag gtg gat<br>Ser Gln His Ala Arg Thr Ser Gly Arg Val Ala Val Glu Glu Val Asp<br>                435                 440                 445 | | 1587 |
| gag gag ggc aag ttt gtc cgg ctg cgc aac aag tcc aat gag gac cag<br>Glu Glu Gly Lys Phe Val Arg Leu Arg Asn Lys Ser Asn Glu Asp Gln<br>            450                 455                 460 | | 1635 |
| tcc atg ggc aat tgg cag atc aag cgc cag aat gga gat gat ccc ttg<br>Ser Met Gly Asn Trp Gln Ile Lys Arg Gln Asn Gly Asp Asp Pro Leu<br>    465                 470                 475 | | 1683 |
| ctg act tac cgg ttc cca cca aag ttc acc ctg aag gct ggg cag gtg<br>Leu Thr Tyr Arg Phe Pro Pro Lys Phe Thr Leu Lys Ala Gly Gln Val<br>480                 485                 490 | | 1731 |
| gtg acg atc tgg gct gca gga gct ggg gcc acc cac agc ccc cct acc<br>Val Thr Ile Trp Ala Ala Gly Ala Gly Ala Thr His Ser Pro Pro Thr<br>495                 500                 505                 510 | | 1779 |
| gac ctg gtg tgg aag gca cag aac acc tgg ggc tgc ggg aac agc ctg<br>Asp Leu Val Trp Lys Ala Gln Asn Thr Trp Gly Cys Gly Asn Ser Leu | | 1827 |

```
                     515                 520                 525
cgt acg gct ctc atc aac tcc act ggg gaa gaa gtg gcc atg cgc aag      1875
Arg Thr Ala Leu Ile Asn Ser Thr Gly Glu Glu Val Ala Met Arg Lys
            530                 535                 540 ctg gtg cgc tca gtg act gtg gtt gag gac gac gag gat gag gat gga      1923
Leu Val Arg Ser Val Thr Val Val Glu Asp Asp Glu Asp Glu Asp Gly
    545                 550                 555 gat gac ctg ctc cat cac cac cac ggc tcc cac tgc agc agc tcg ggg      1971
Asp Asp Leu Leu His His His His Gly Ser His Cys Ser Ser Ser Gly
560                 565                 570 gac ccc gct gag tac aac ctg cgc tcg cgc acc gtg ctg tgc ggg acc      2019
Asp Pro Ala Glu Tyr Asn Leu Arg Ser Arg Thr Val Leu Cys Gly Thr
575                 580                 585                 590 tgc ggg cag cct gcc gac aag gca tct gcc agc ggc tca gga gcc cag      2067
Cys Gly Gln Pro Ala Asp Lys Ala Ser Ala Ser Gly Ser Gly Ala Gln
                595                 600                 605 agc ccc cag aac tgc agc atc atg taa tctgggacct gccaggcagg            2114
Ser Pro Gln Asn Cys Ser Ile Met
            610 ggtgggggtg gaggcttcct gcgtcctcct cacctcatgc ccaccccctg ccctgcacgt    2174
catgggaggg ggcttgaagc caaagaaaaa taaccctttg gttttttttct tctgtatttt   2234
tttttctaag agaagttatt ttctacagtg gttttatact gaaggaaaaa cacaagcaaa    2294
aaaaaaaaaa agcatctatc tcatctatct caatcctaat ttctcctccc ttccttttcc    2354
ctgcttccag gaaactccac atctgcctta aaccaaaga gggcttcctc tagaagccaa     2414
gggaaagggg tgcttttata gaggctagct tctgcttttc tgccctggct gctgccccca    2474
ccccggggac cctgtgacat ggtgcctgag aggcaggcat agaggcttct ccgccagcct    2534
cctctggacg gcaggctcac tgccaggcca gcctccgaga gggagagaga gagagagagg    2594
acagcttgag ccgggcccct gggcttggcc tgctgtgatt ccactacacc tggctgaggt    2654
tcctctgcct gccccgcccc cagtccccac ccctgccccc agcccgggg tgagtccatt     2714
ctcccaggta ccagctgcgc ttgcttttct gtattttatt tagacaagag atgggaatga    2774
ggtgggaggt ggaagaaggg agaagaaagg tgagtttgag ctgccttccc tagctttaga    2834
ccctgggtgg gctctgtgca gtcactggag gttgaagcca agtggggtgc tgggaggagg    2894
gagagggagg tcactggaaa ggggagagcc tgctggcacc caccgtggag gaggaaggca    2954
agaggggtg gaggggtgtg gcagtggttt tggcaaacgc taaagagccc ttgcctcccc     3014
atttcccatc tgcacccctt ctctcctccc caaatcaata cactagttgt ttctacccct    3074
ggcaaaaaaa aaaaa                                                    3089

<210> SEQ ID NO 8
<211> LENGTH: 614
<212> TYPE: PRT
<213> ORGANISM: Homo sapiens

<400> SEQUENCE: 8

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60
```

```
Glu Ser Glu Glu Val Val Ser Arg Glu Val Ser Gly Ile Lys Ala Ala
 65                  70                  75                  80

Tyr Glu Ala Glu Leu Gly Asp Ala Arg Lys Thr Leu Asp Ser Val Ala
                 85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Leu Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480
```

```
Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510

Val Trp Lys Ala Gln Asn Thr Trp Gly Cys Gly Asn Ser Leu Arg Thr
        515                 520                 525

Ala Leu Ile Asn Ser Thr Gly Glu Glu Val Ala Met Arg Lys Leu Val
    530                 535                 540

Arg Ser Val Thr Val Val Glu Asp Asp Glu Glu Asp Gly Asp Glu Asp
545                 550                 555                 560

Leu Leu His His His His Gly Ser His Cys Ser Ser Ser Gly Asp Pro
                565                 570                 575

Ala Glu Tyr Asn Leu Arg Ser Arg Thr Val Leu Cys Gly Thr Cys Gly
            580                 585                 590

Gln Pro Ala Asp Lys Ala Ser Ala Ser Gly Ser Gly Ala Gln Ser Pro
        595                 600                 605

Gln Asn Cys Ser Ile Met
    610

<210> SEQ ID NO 9
<211> LENGTH: 15
<212> TYPE: DNA
<213> ORGANISM: Artificial Sequence
<220> FEATURE:
<223> OTHER INFORMATION: Lamin A probe

<400> SEQUENCE: 9
cgctgagtac aacct                                                    15

<210> SEQ ID NO 10
<211> LENGTH: 20
<212> TYPE: DNA
<213> ORGANISM: Artificial Sequence
<220> FEATURE:
<223> OTHER INFORMATION: Lamin A forward primer

<400> SEQUENCE: 10
gacgaggatg aggatggaga                                               20

<210> SEQ ID NO 11
<211> LENGTH: 20
<212> TYPE: DNA
<213> ORGANISM: Artificial Sequence
<220> FEATURE:
<223> OTHER INFORMATION: Lamin A reverse primer.

<400> SEQUENCE: 11
gagtgaccgt gacactggag                                               20

<210> SEQ ID NO 12
<211> LENGTH: 20
<212> TYPE: DNA
<213> ORGANISM: Artificial Sequence
<220> FEATURE:
<223> OTHER INFORMATION: Lamin C probe.

<400> SEQUENCE: 12
agatgacctg ctccatcacc                                               20

<210> SEQ ID NO 13
<211> LENGTH: 20
<212> TYPE: DNA
```

```
<213> ORGANISM: Artificial Sequence
<220> FEATURE:
<223> OTHER INFORMATION: Lamin C forward primer.

<400> SEQUENCE: 13
gtggaaggca cagaacacct                                               20

<210> SEQ ID NO 14
<211> LENGTH: 18
<212> TYPE: DNA
<213> ORGANISM: Artificial Sequence
<220> FEATURE:
<223> OTHER INFORMATION: Lamin C reverse primer.

<400> SEQUENCE: 14
gcggcggcta ccactcac                                                 18

<210> SEQ ID NO 15
<211> LENGTH: 20
<212> TYPE: DNA
<213> ORGANISM: Artificial Sequence
<220> FEATURE:
<223> OTHER INFORMATION: Lamin A-delta-10 probe.

<400> SEQUENCE: 15
agtacaacct gcgctcgcgc                                               20

<210> SEQ ID NO 16
<211> LENGTH: 21
<212> TYPE: DNA
<213> ORGANISM: Artificial Sequence
<220> FEATURE:
<223> OTHER INFORMATION: Lamin A-delta-10 forward primer.

<400> SEQUENCE: 16
aactccactg gggaaggctc c                                             21

<210> SEQ ID NO 17
<211> LENGTH: 20
<212> TYPE: DNA
<213> ORGANISM: Artificial Sequence
<220> FEATURE:
<223> OTHER INFORMATION: Lamin A-delta-10 reverse primer.

<400> SEQUENCE: 17
gctcctgagc cgctggcaga                                               20

<210> SEQ ID NO 18
<211> LENGTH: 22
<212> TYPE: DNA
<213> ORGANISM: Artificial Sequence
<220> FEATURE:
<223> OTHER INFORMATION: Lamin A-delta-50 probe

<400> SEQUENCE: 18
agcatcatgt aatctgggac ct                                            22

<210> SEQ ID NO 19
<211> LENGTH: 18
<212> TYPE: DNA
<213> ORGANISM: Artificial Sequence
<220> FEATURE:
<223> OTHER INFORMATION: Lamin A-delta-50 forward primer.

<400> SEQUENCE: 19
gcgtcaggag ccctgagc                                                 18
```

<210> SEQ ID NO 20
<211> LENGTH: 18
<212> TYPE: DNA
<213> ORGANISM: Artificial Sequence
<220> FEATURE:
<223> OTHER INFORMATION: Lamin A-delta-50 reverse primer

<400> SEQUENCE: 20
gacgcaggaa gcctccac                                                 18

<210> SEQ ID NO 21
<211> LENGTH: 24
<212> TYPE: DNA
<213> ORGANISM: Artificial Sequence
<220> FEATURE:
<223> OTHER INFORMATION: Ubiquitin probe.

<400> SEQUENCE: 21
cccacctctg agacggagca ccag                                          24

<210> SEQ ID NO 22
<211> LENGTH: 24
<212> TYPE: DNA
<213> ORGANISM: Artificial Sequence
<220> FEATURE:
<223> OTHER INFORMATION: Ubiquitin forward primer.

<400> SEQUENCE: 22
actacaacat ccagaaagag tcca                                          24

<210> SEQ ID NO 23
<211> LENGTH: 21
<212> TYPE: DNA
<213> ORGANISM: Artificial Sequence
<220> FEATURE:
<223> OTHER INFORMATION: Ubiquitin reverse primer

<400> SEQUENCE: 23
ccagtcaggg tcttcacgaa g                                             21

<210> SEQ ID NO 24
<211> LENGTH: 24
<212> TYPE: DNA
<213> ORGANISM: Artificial Sequence
<220> FEATURE:
<223> OTHER INFORMATION: RPL-13 probe.

<400> SEQUENCE: 24
cgcaagcgga tgaacaccaa ccct                                          24

<210> SEQ ID NO 25
<211> LENGTH: 24
<212> TYPE: DNA
<213> ORGANISM: Artificial Sequence
<220> FEATURE:
<223> OTHER INFORMATION: RPL-13 forward primer

<400> SEQUENCE: 25
aacaagttga agtacctggc tttc                                          24

<210> SEQ ID NO 26
<211> LENGTH: 20
<212> TYPE: DNA
<213> ORGANISM: Artificial Sequence
<220> FEATURE:

<223> OTHER INFORMATION: RPL-13 reverse primer.

<400> SEQUENCE: 26
tggttttgtg gggcagcata                                               20

<210> SEQ ID NO 27
<211> LENGTH: 24
<212> TYPE: DNA
<213> ORGANISM: Artificial Sequence
<220> FEATURE:
<223> OTHER INFORMATION: Beta-actin probe.

<400> SEQUENCE: 27
cggctacagc ttcaccacca cggc                                          24

<210> SEQ ID NO 28
<211> LENGTH: 24
<212> TYPE: DNA
<213> ORGANISM: Artificial Sequence
<220> FEATURE:
<223> OTHER INFORMATION: Beta-actin forward primer.

<400> SEQUENCE: 28
tgactgacta cctcatgaag atcc                                          24

<210> SEQ ID NO 29
<211> LENGTH: 22
<212> TYPE: DNA
<213> ORGANISM: Artificial Sequence
<220> FEATURE:
<223> OTHER INFORMATION: Beta-actin reverse primer

<400> SEQUENCE: 29
ccatctcttg ctcgaagtcc ag                                            22

<210> SEQ ID NO 30
<211> LENGTH: 17
<212> TYPE: DNA
<213> ORGANISM: Artificial Sequence
<220> FEATURE:
<223> OTHER INFORMATION: Progerin S primer of Rodriquez, et al.

<400> SEQUENCE: 30
actgcagcag ctcgggg                                                  17

<210> SEQ ID NO 31
<211> LENGTH: 16
<212> TYPE: DNA
<213> ORGANISM: Artificial Sequence
<220> FEATURE:
<223> OTHER INFORMATION: Progerin A-primer of Rodriguez, et al.

<400> SEQUENCE: 31
tctgggggct ctgggc                                                   16

<210> SEQ ID NO 32
<211> LENGTH: 15
<212> TYPE: DNA
<213> ORGANISM: Artificial Sequence
<220> FEATURE:
<223> OTHER INFORMATION: Progerin probe

<400> SEQUENCE: 32
cgctgagtac aacct                                                    15

QUANTIFICATION OF LAMIN C AND LAMIN A FOR TUMOR CLASSIFICATION

CROSS-REFERENCE TO RELATED APPLICATIONS

This application claims the benefit of U.S. Provisional Application No. 62/097,507, filed Dec. 29, 2014, the entire disclosure of which is hereby incorporated by reference.

BACKGROUND OF THE INVENTION

Field of the Invention

The invention pertains to the fields of cancer diagnosis and therapy. It relates to methods and kits for detecting and quantifying the expression of alternatively spliced Lamin C and Lamin A mRNAs, and especially to determination of the ratio of Lamin C mRNA to Lamin A mRNA in a biological sample. The inventor has found that this ratio is useful for identifying or classifying a neoplasm, such as breast cancer, and for selecting a treatment or treatment regimen for a patient having the neoplasm. Additional aspects of the invention relate to selecting a therapeutic method for treating a subject based on identification of the ratio of Lamin C mRNA to Lamin A mRNA.

Description of Related Art

The description of the related art provided herein is for the purpose of generally presenting the context of the disclosure. Work of the presently named inventor, to the extent it is described in this background section, as well as aspects of the description which may not otherwise qualify as prior art at the time of filing, is neither expressly nor impliedly admitted as prior art against the present invention.

The Lamin A/C gene encodes several lamin nuclear proteins through alternative splicing of mRNA transcribed from this gene. Nuclear lamins, also known as class V intermediate filaments, are fibrous proteins that make up the nuclear lamina matrix. The lamina is about 10 nm thick and underlies the inner nuclear membrane, which is reversibly broken-down during mitosis by way of phosphorylation. The major function of the nuclear lamina is to maintain structure and integrity of the nucleus. Lamins are highly dynamic in nature and are implicated in the nonrandom positioning of sub chromosome domains. They contribute to the size, shape, and overall mechanical stability of the nucleus and are involved in the overall organization of chromatin, regulating the cell cycle, DNA replication, transcription, cell differentiation, apoptosis and aging; Broers, et al., J. Cell. Sci. 112(Pt 20): 3463-75 (1999); Taddei, et al., Annu. Rev. Genet. 38:305-45 (2004); Shimi, et al., Adv. Exp. Med. Biol. 773:415-30 (2014).

Alternative splicing of mRNA transcribed from the Lamin A/C gene (also known as the LMNA gene) produces several different Lamin mRNA splice variants that encode the Lamin A, Lamin C, Lamin AΔ10, Lamin AΔ50 (Progerin), and Lamin C2 proteins. Lamin C mRNA is a transcript variant missing all of exons 11 and 12 present in Lamin A mRNA. Lamin AΔ10 mRNA is an alternative splicing product of the Lamin A/C gene lacking exon 10 and has a relatively low abundance compared to Lamin A and C mRNA; Machiels, et al., J. Biol. Chem. 271: 9249-53 (1996). Progerin mRNA is missing 150 nucleotides from the end of exon 11 (and the corresponding protein has a deletion of 50 amino acids near the C-terminal) and Lamin C2 mRNA is specific to the testis; Cao, et al., J. Hum. Genet. 48:271-4 (2003); De Sandre-Giovanni, et al., Science 300: 2055 (2003); Eriksson, et al., Nature 423:293-8 (2003).

Lamin A and Lamin C, which are encoded by two of the above splice-variants, are two fibrous nuclear proteins that are translated from alternative mRNA splice variants of the same Lamin A/C (LMNA) gene which contains 12 exons.

Lamin A was identified as a biomarker colonic cells by Willis et al. who also found that Lamin A was upregulated in colorectal cancer (CRC) cells. Upregulation of Lamin A was associated with increased invasiveness and motility of CRC cells, but not with cellular proliferation. This was suggested as creating a more aggressive stem cell-like phenotype correlating with a two fold increase in mortality; Willis, et al., PLOS One 3:e2988 (2008); Willis, et al., Biochem. Soc. Trans. 36:1350-3 (2008). On the other hand, the study by Willis et al. detected Lamin A in the stem cell niche but not in transit amplifying cells. Lamin C, encoded by a different splice variant, was not found in either the stem cell niche or in transit amplifying cells; Willis, et al., PLOS One 3:e2988 (2008). Controversially, low expression of Lamin A was associated with increased disease recurrence in stage II and III colon cancer patients Belt, et al., Eur. J. Canc. 47: 1837-45 (2011).

Past research has studied Lamin A and Lamin C collectively assuming that both proteins function as one. It was not known whether these proteins act in concert or have distinct roles and associations in cancer cells. Although Lamin A and Lamin C only differ by 98 residues, recent studies have illustrated the unique roles of Lamin A and Lamin C. Structurally, Lamin C is unique to the other Lamins in that it is the only Lamin lacking the carboxy-terminal sequence that is required for membrane attachment during its biogenesis and trafficking to the nucleus (Al-Saaidi, et al., Chromosoma 124(1):1-12 (2014) and is found exclusively in mammals; Peter, et al., Nucleus 3:44-59 (2002). It is hypothesized that this C-terminal end may play a role in senescence. Additionally, it was found that the tumor suppressor AIMP3/P18 to be involved in ubiquitination-dependent degradation of Lamin A, but not Lamin C, indicating that this C-terminal end may have various roles; Oh, et al., Aging Cell 9:810-22 (2010). Even though well studied, the difference still remains vague and poorly understood as apparent from the publications cited below.

Hung, et al., U.S. 2004/0018546 A1 proposes detecting various markers including those from nuclear matrix proteins such as Lamin A, Lamin B, and Lamin C in ductal fluid from breasts. Their focus is on use of ductal fluid and no correlations between expression of Lamin A, Lamin C or a ratio of Lamin C to Lamin A markers are shown.

Hutchison, et al., U.S. 2010/0297618 A1 describes a method for determining a prognosis of colorectal cancer by measuring Lamin A indicating that a loss or mislocalisation of A-type lamin proteins correlates with a positive prognosis while the presence of A-type lamin proteins is indicative of a poor prognosis.

Park, et al. U.S. 2011/0033873 A1 describes proteonomic markers for early detection of hepatocellular carcinoma. They propose that Lamin C (Lamin A/C transcript variant 2) can be used as a tumor marker.

Wazir, et al., Cell. Mol. Biol. Lett. 18(4): 595-611 (2013) studied associations among mRNA expression by Lamin A/C, Lamin B1 and Lamin B receptor. Wazir does not distinguish between different Lamin A/C transcript variants such as Lamin A (transcript variant 1) and Lamin C (transcript variant 2) which encode lamin proteins having different structures and functions.

The expression of Lamin A, Lamin C and other lamins was not believed to be a reliable biomarker due to differential expression of lamins in various tissues as shown in Table 1 and in view of conflicting or inconsistent experimental studies. Lamin C and Progerin have been shown to have distinct and opposite functions in relation to cellular energy expenditure and lifespan; Lopez-Mejia, et al., EMBO Reports 15:529-39 (2014). The variation in expression of Lamin A and Lamin C in different kinds of cells has been attributed to altered splicing, mRNA stability, translation efficiency, or protein stability; Al-Saaidi, et al., Chromosoma (2014)).

Lamins are expressed in well-differentiated cells and tissues among humans but not or poorly expressed in stem cells; Broers, et al., Histochem. Cell Biol. 107:505-17 (1997); Eckersley-Maslin, et al., Nucleus 4:53-60 (2013). Lamin A was found to be expressed highly in stem cells while Lamin C was found to be expressed in differentiated epithelial cells and smooth muscles of the colon; Willis, et al., Biochem. Soc. Trans. 36:1350-3 (2008). Previous reports indicated that the heart, kidney, and liver show similar levels of Lamin A and Lamin C, while skeletal muscles have higher expression of Lamin A and Lamin C than cardiac ones; Rober, et al., Development 105:365-78 (1989); Swift, et al., Science 341: 1240104 (2013). In contrast, a higher level of Lamin C compared to Lamin A has been reported in astrocytes, oligodendrocytes, and neurons and mouse retinal neurons, i.e., neuronal tissues; Jung, et al., Molec. Neurobiol. 47:290-301 (2013); Wakabayashi, et al., Histochem. Cell Biol. 136:427-36 (2011). The expression of Lamin A is reduced or absent in subsets of cells with a low degree of differentiation and/or cells that are highly proliferating including human malignancies; Broers, et al., Histochem. Cell Biol. 107:505-17 (1997); Rober, et al., Development 105:365-78 (1989); Hutchison, et al., Nat. Cell. Biol. 6:1062-7 (2004), especially leukemia and lymphomas; Stadelmann, et al., Leuk. Res. 14:815-21 (1990); Lin, et al., Exp. Cell Res. 236: 378-84 (1997).

It has also been illustrated that the loss of the Lamin A/C gene compromises the nuclear envelope and leads to breast cancer aberrations in nuclear morphology and aneuploidy; Capo-chichi, et al. Chinese J. Canc. 30:415-25 (2011). Epigenetic silencing of the Lamin A/C gene by CpG island promoter hypermethylation correlated with the loss of RNA and protein expression in leukemia and lymphoma malignancies; Agrelo, et al., J. Clin. Oncol. 23: 3940.7 (2005). Low expression of Lamin A was also found to be associated with increased disease recurrence in stage II and III in CRC patients; Belt, et al., Eur. J. Canc. 47:1837-45 (2011).

In view of these obstacles, and prompted by the need for early detection and accurate staging and monitoring of cancer, the inventor sought to develop a reliable biomarker based on the expression of lamins that was not limited to measuring the expression of a single type of lamin as a tumor or cancer biomarker and avoid the problems associated with variant expression of lamins in different tissues. Therefore, the coexpression of different lamin splice variants was studied to determine whether quantitative differences amongst lamin mRNA splice variants expression would provide reliable biomarkers for cancer or tumors. Surprisingly, the inventor found that the ratio of Lamin C mRNA to Lamin A mRNA to be a reliable biomarker of cancer for many different types of cancer. This provided a basis for new methods for early detection of cancer, for monitoring the effects of cancer chemotherapy and for significantly improving prognostic outcomes by increasing mean survival rates and times for patients.

BRIEF SUMMARY OF THE INVENTION

The inventor has developed a simple and economic method for diagnosing breast cancer and other kinds of cancers by quantitatively detecting mRNA encoding Lamin A and mRNA encoding Lamin C in a biological sample, comparing the amount of mRNA encoding Lamin C relative to the amount of mRNA encoding Lamin A, and selecting a subject having breast cancer or another kind of cancer or tumor, when a ratio of Lamin C mRNA to Lamin A mRNA is elevated compared to the ratio in a control biological sample from a subject who does not have cancer. The inventor shows that the ratio of Lamin C mRNA to Lamin A mRNA is significantly elevated in breast cancer cells as well as numerous other kinds of cancer.

The inventor also provides herein specific combinations of probes and primers that provide a sensitive and highly specific method for detecting alternative splice variants of the Lamin A/C gene, for example, through use of TaqMan quantitative real-time PCR (qRT-PCR).

Other applications of this technology, which are based on detection of the ratio of Lamin C to Lamin A expression products (e.g., mRNA and protein), include methods for characterizing or staging a cancer or tumor, such as its proliferative, apoptotic, metastatic capacity, its cell cycle checkpoints, or its drug or radiation susceptibility, methods for prognosing, characterizing, or subgrouping cancer or tumor patients, screening methods for drugs, nucleotides, immune response modifiers, small molecules, radiation, and other agents that normalize a Lamin C to Lamin A ratio, and methods for modifying tumor or cancer cells to express a more normal ratio of Lamin C to Lamin A with the objective of obtaining a more normal cellular phenotype, and methods for selecting a treatment or treating a cancer or tumor patient based on the detection of a Lamin C to Lamin A ratio in a patient's cancer or tumor cells.

BRIEF DESCRIPTION OF THE SEVERAL VIEWS OF THE DRAWING(S)

FIGS. 1A-1H depict representative gels of amplified amplicons for each corresponding cDNA. FIG. 1A shows Lamin A (214 bp); FIG. 1B shows Lamin C (178 bp); FIG. 1C shows lamin AMID (131 bp) and FIG. 1D shows Progerin (89 bp). FIGS. 1E-1H show representative gels of Lamin A/C transcript variants primer specificities. Lamin A/C transcript variants were amplified according to the optimized conditions for each primer. qRT-PCR was performed either with cDNA (1 pg/reaction) for (1) Lamin A cDNA or (2) Lamin C cDNA or (3) Lamin AΔ10 cDNA or (4) Progerin cDNA. Non-template control (NTC) was also run for each primer pair.

FIGS. 2A-2D describe Lamin A/C transcript variants assay serial dilution curves. FIG. 2A depicts a curve for Lamin A, FIG. 2B a curve for Lamin C, FIG. 2C a curve for Lamin AΔ10; and FIG. 2D a curve for Progerin. Probe sensitivity was tested by performing Lamin A or Lamin C or Lamin AΔ10 or Lamin AΔ50 TaqMan qRT-PCR assays with a serial dilution of approximately 300,000 to 30 copies of plasmid DNA of either Lamin A, Lamin C, Lamin AΔ10, Progerin cDNAs, or an empty vector control. The Y axis represents cycle-threshold (Ct) values and the X axis represents log DNA copy number. The slope and regression coefficient ($r^2$ value) of the standard dilution curves are indicated below each curve.

Figure 3A:
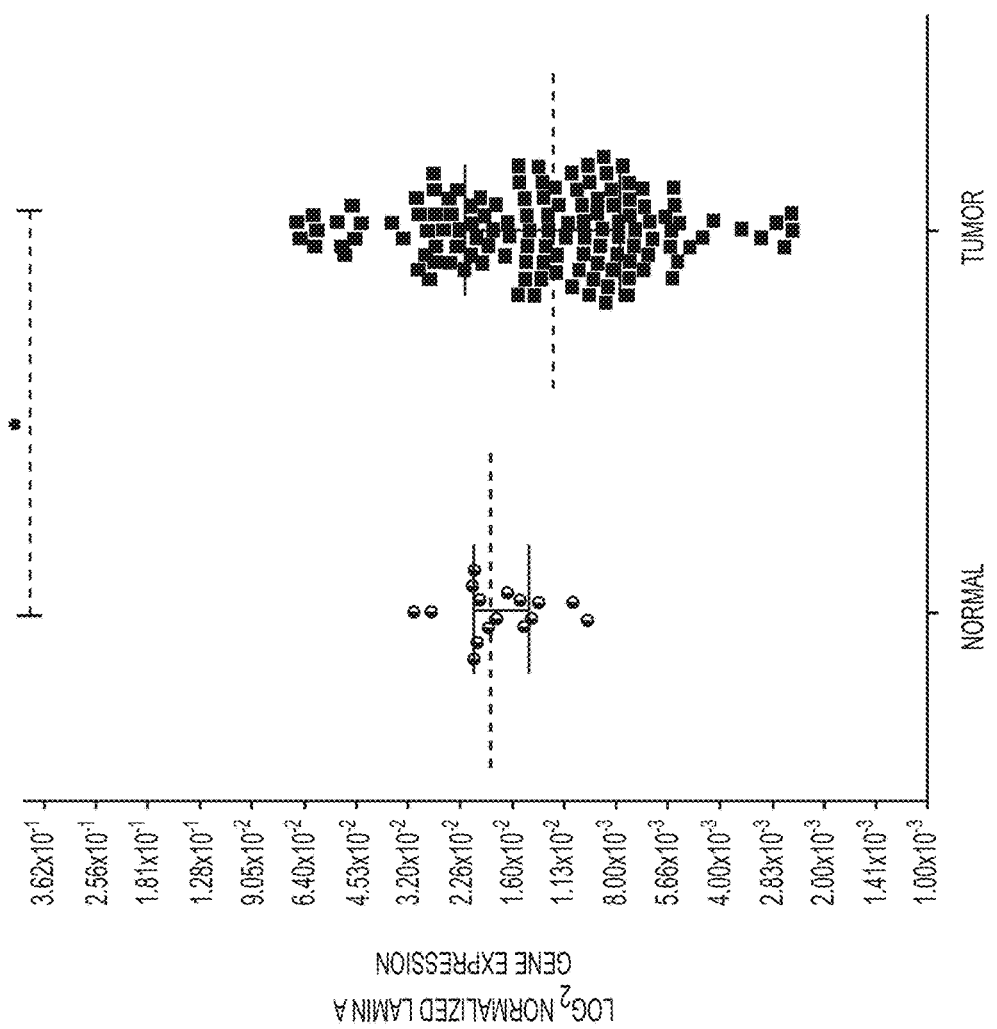
Figure 3B:
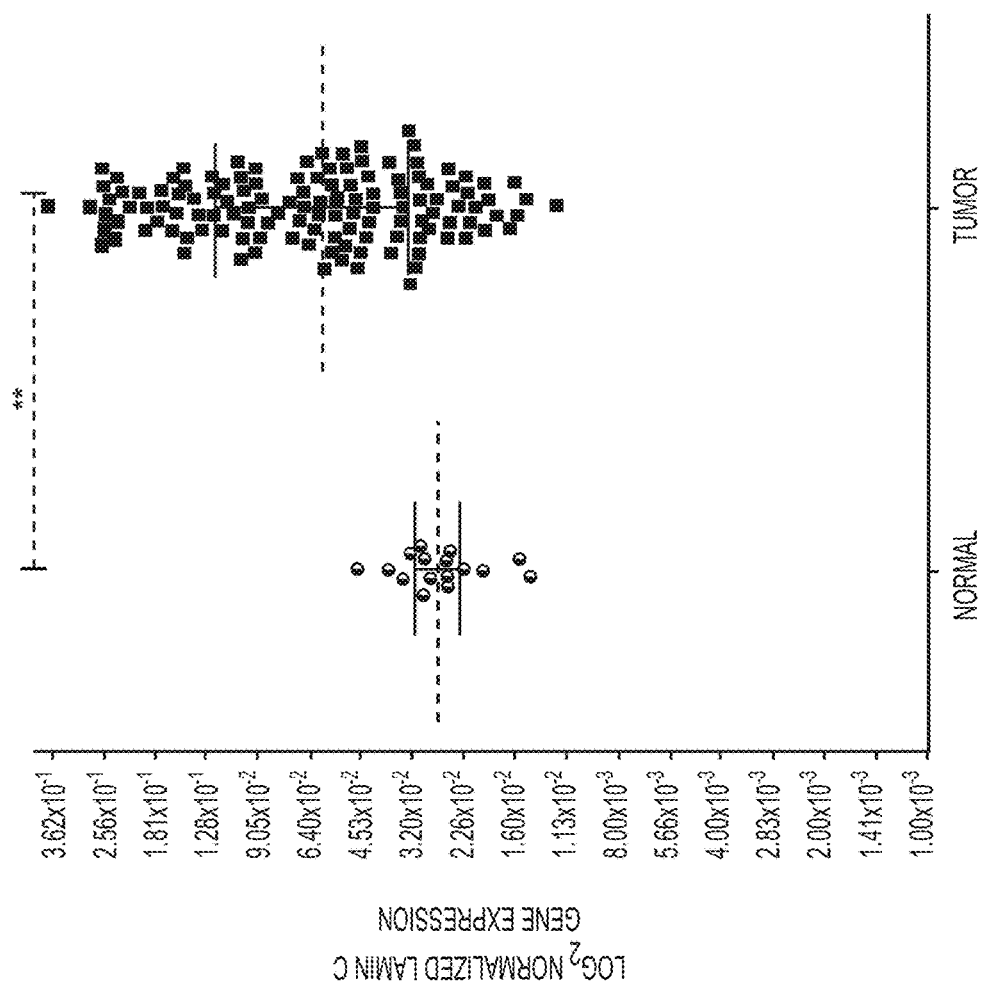
Figure 3C:
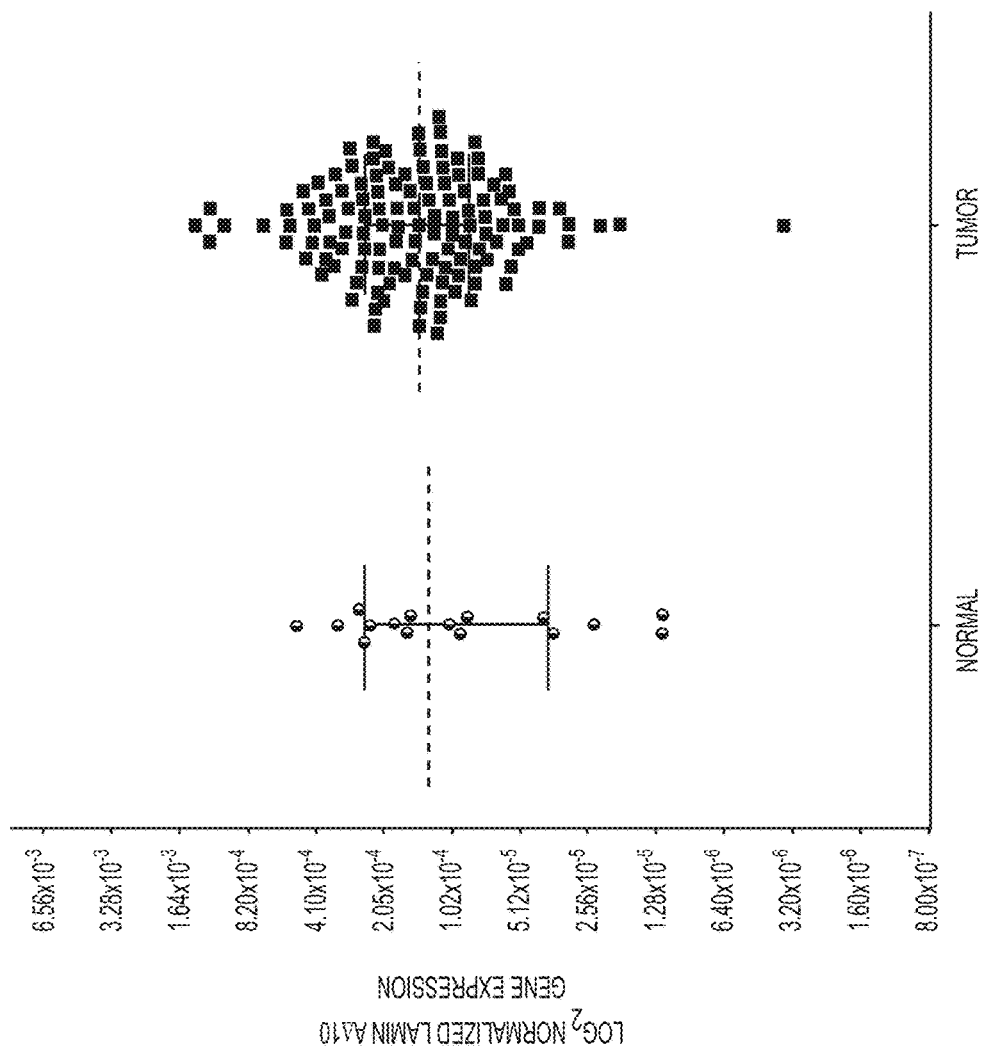

FIGS. 3A-3D describe normalized mRNA expression levels. FIG. 3A: Lamin A; FIG. 3B: Lamin C; FIG. 3C: Lamin AΔ10 and FIG. 3D: Progerin as found in primary breast cancer (n=128) compared to normal (n=16—normal) breast tissues (Breast Cancer cDNA arrays, BCRT101, BCRTIO2 and BCRT104). The expression levels of Lamin A/C transcript variants were normalized to the average expression levels of three housekeeping genes (Ubiquitin, RPL13 and β-actin). A Mann-Whitney Rank Sum Test between normal and tumor specimens analysis identified a significant difference between normal and tumor samples for Lamin A, Lamin C and Progerin (*=P<0.05; **=P<0.001), whereas no difference was observed in Lamin AΔ10. Dotted bars represent the median $\log_2$ mRNA expression value within a particular gene target. The error bars represent IQR (Q1-Q3).

Figure 4A:
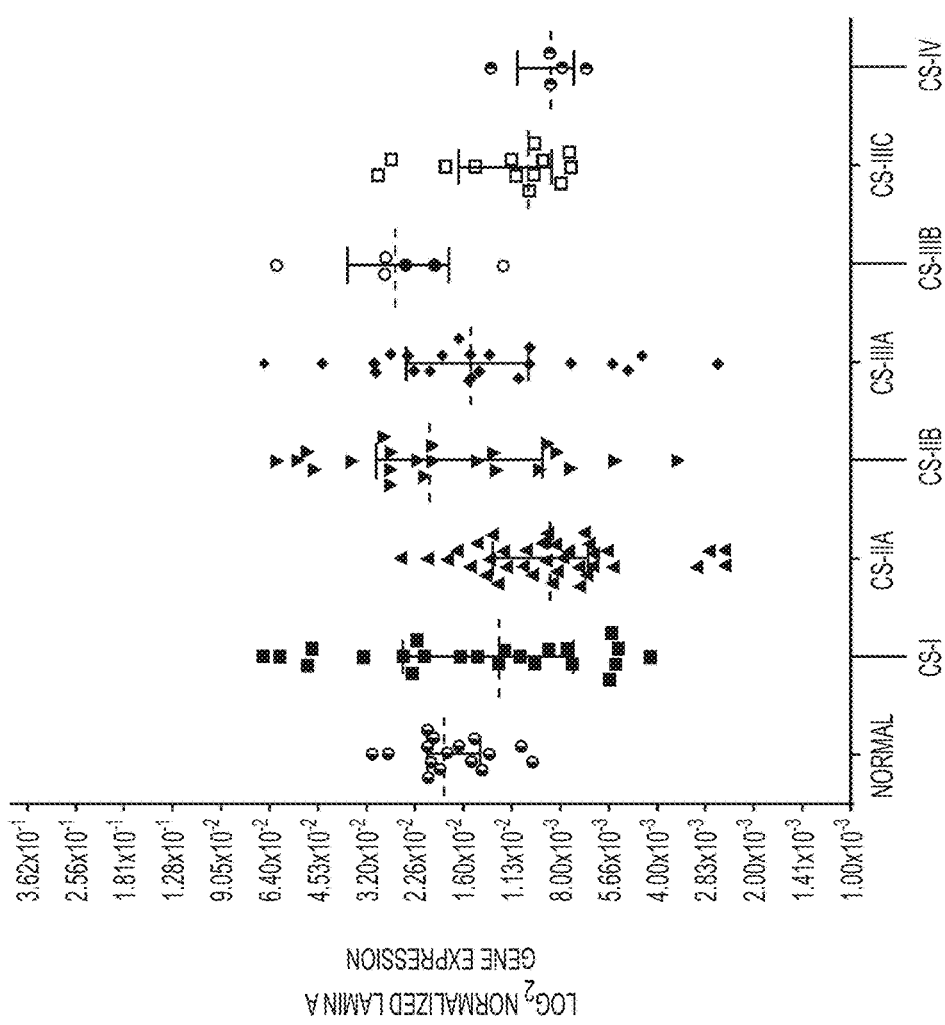
Figure 4C:
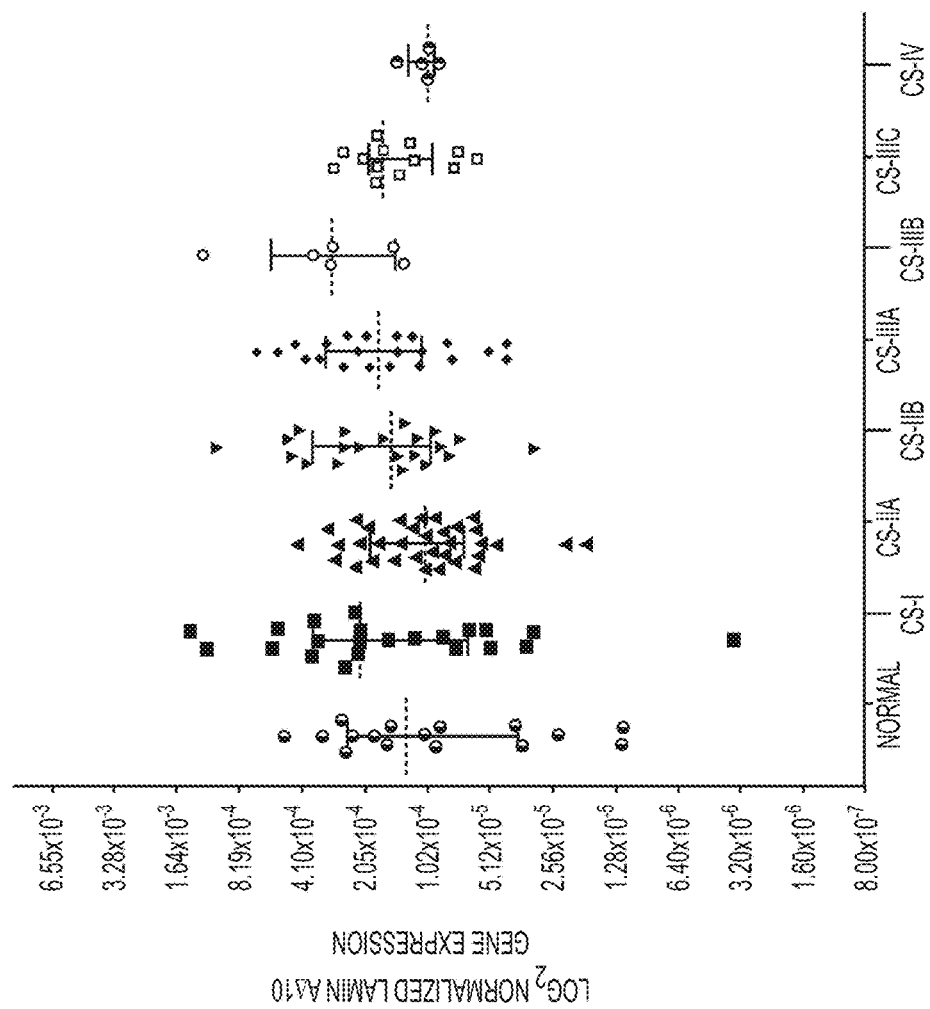
Figure 4D:
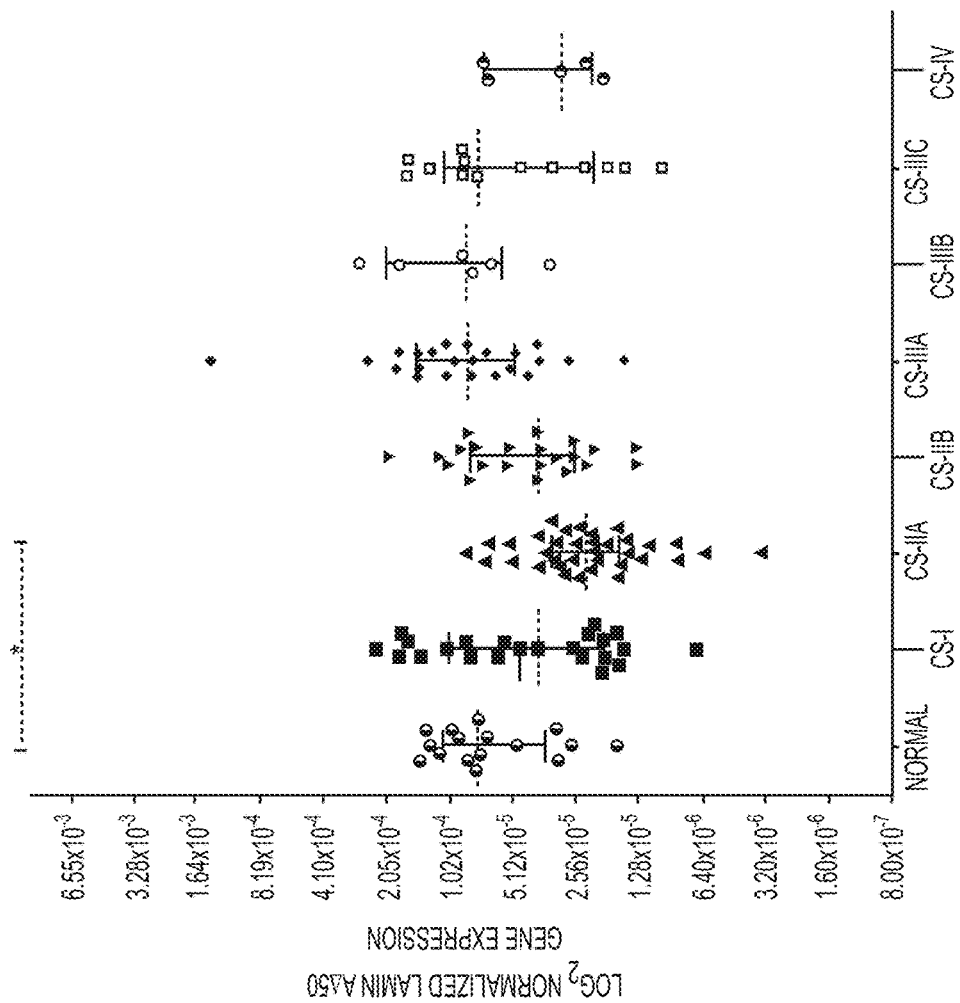

FIGS. 4A-4D describe TaqMan qRT-PCR measurement of relative mRNA expression levels for Lamin A (FIG. 4A); Lamin C (FIG. 4B); Lamin AΔ10 (FIG. 4C); and Progerin (FIG. 4D) in Breast Cancer cDNA arrays (BCRT101, BCRTI02 and BCRT104) following stratification of patients into groups according to clinical metastatic stage. Kruskal-Wallis ANOVA analysis followed by Dunn's test for comparisons against the control group. Asterisks indicate statistically significant differences (*: P<0.05) between tumor stage and normal samples. Dotted bars represent the median of Lamin A/C transcript variants. The error bars represent IQR (Q1-Q3); n=16—normal, 23—Stage I, 36—IIA, 22—IIB, 23—IIIA, 6—IIIB, 13—IIIC, 5—IV.

Figure 5A:
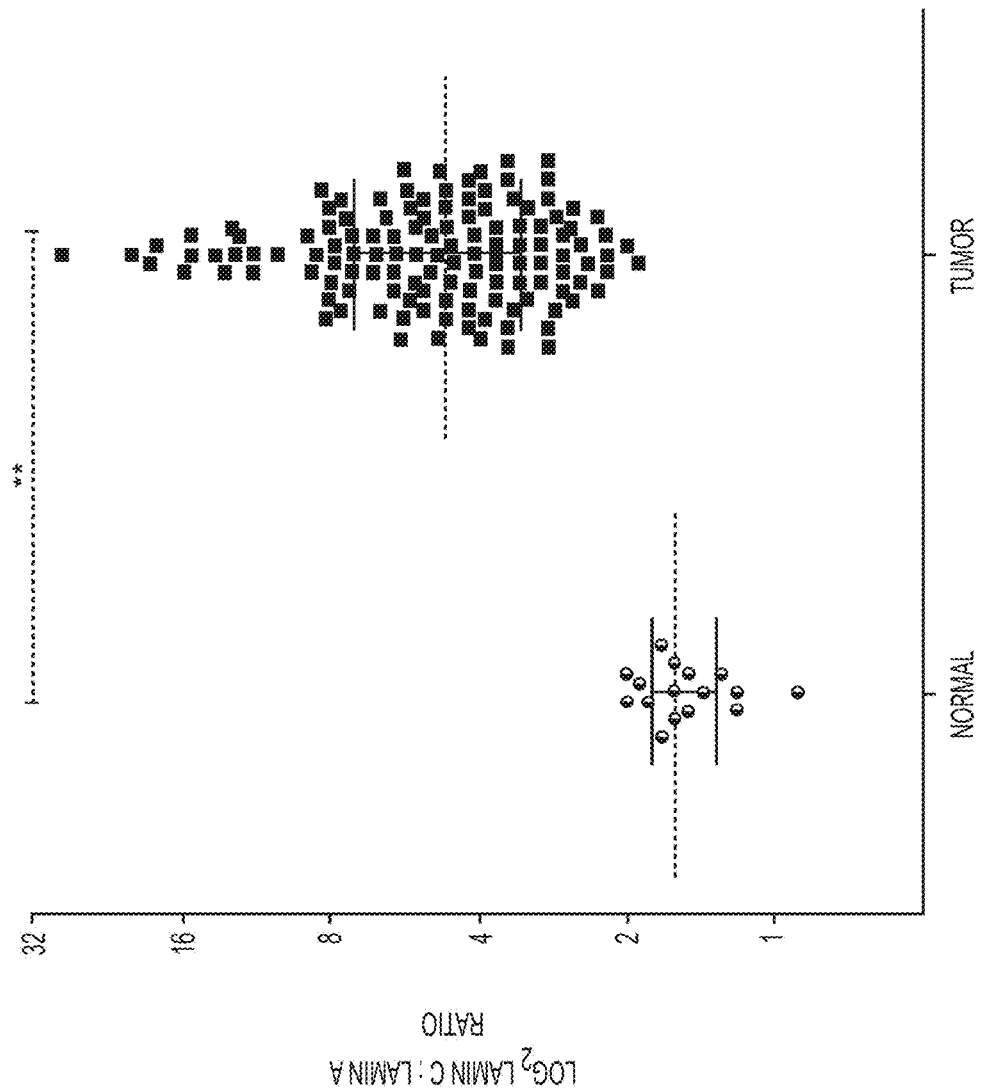
Figure 5B:
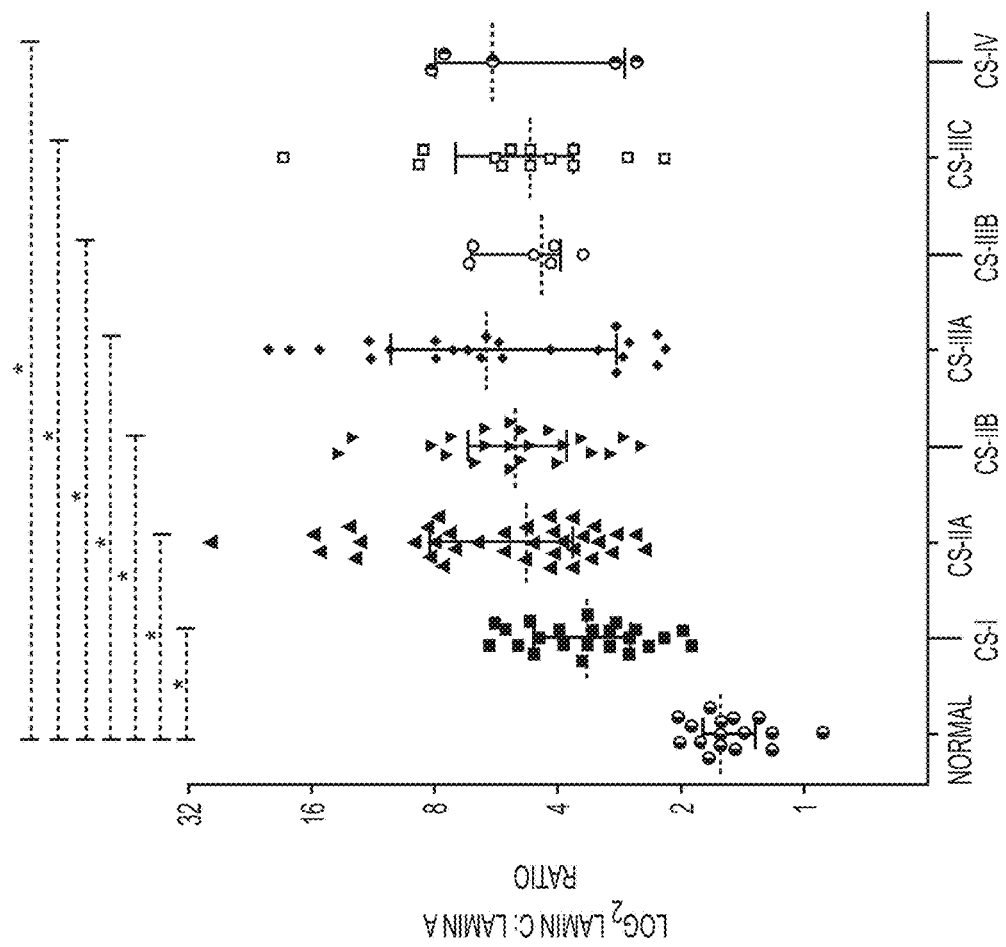

FIGS. 5A-5B compare Lamin C and Lamin A ratios. FIG. 5A shows a comparison of Lamin C: Lamin A mRNA ratio between normal and breast cancer tissues; and FIG. 5B compares Lamin C: Lamin A mRNA ratios in the same samples following stratification of samples according to the clinical stage in Breast Cancer cDNA arrays (BCRT101, BCRTIO2 and BCRT104). The mean normalized expression levels of Lamin A and Lamin C was calculated using Q-Gene software. A Mann-Whitney Rank Sum Test between normal (n=16) and tumor (n=136) specimens analysis identified a significant difference between normal and tumor samples for Lamin C: Lamin A ratio, whereas Kruskal-Wallis ANOVA analysis identified significant differences between normal breast tissues and all clinical stages of breast cancer. The error bars represent IQR (Q1-Q3); n=16—normal, 23—Stage I, 36—IIA, 22—IIB, 23—IIIA, 6—IIIB, 13—IIIC, 5—IV; *: P<0.05; **: P<0.05.

Figure 6A:
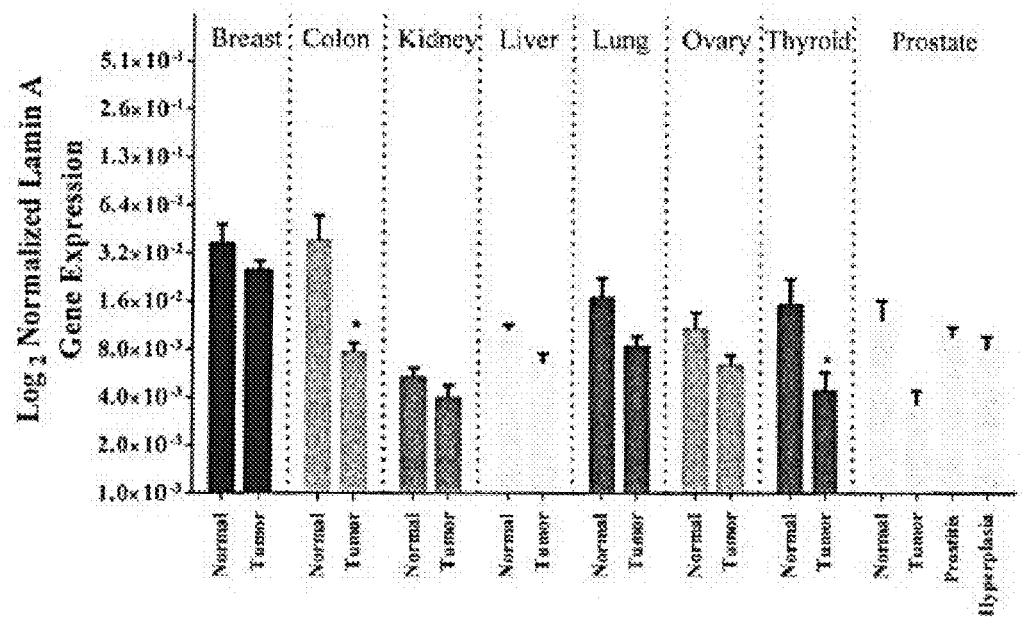
Figure 6B:
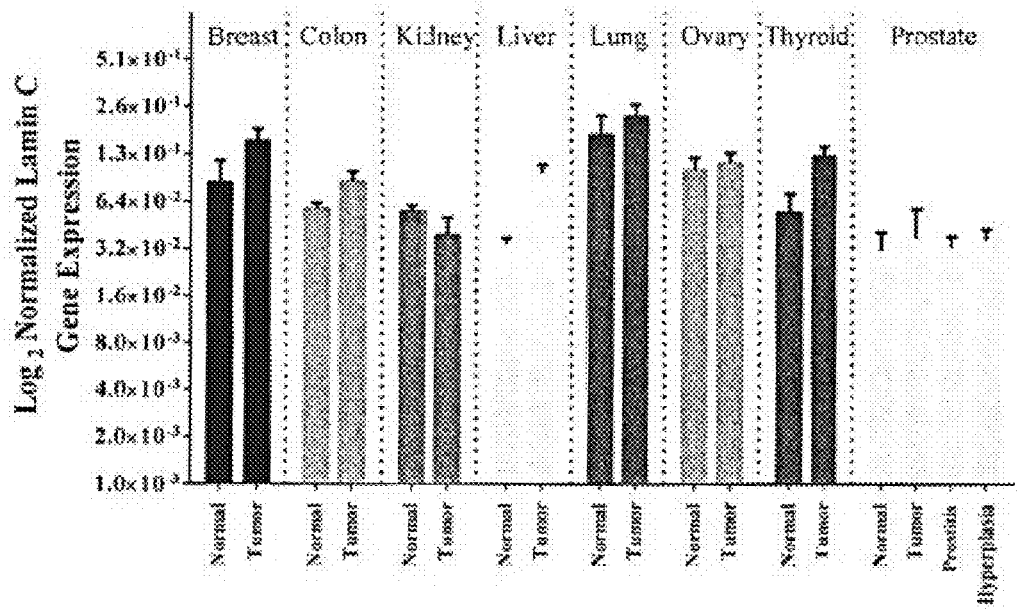
Figure 6C:
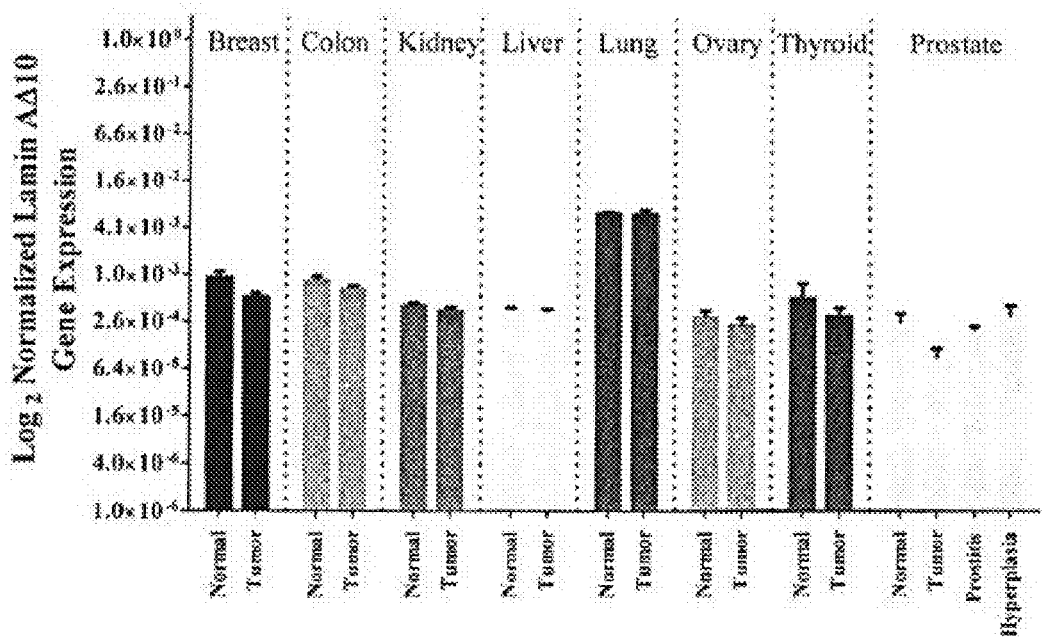
Figure 6D:
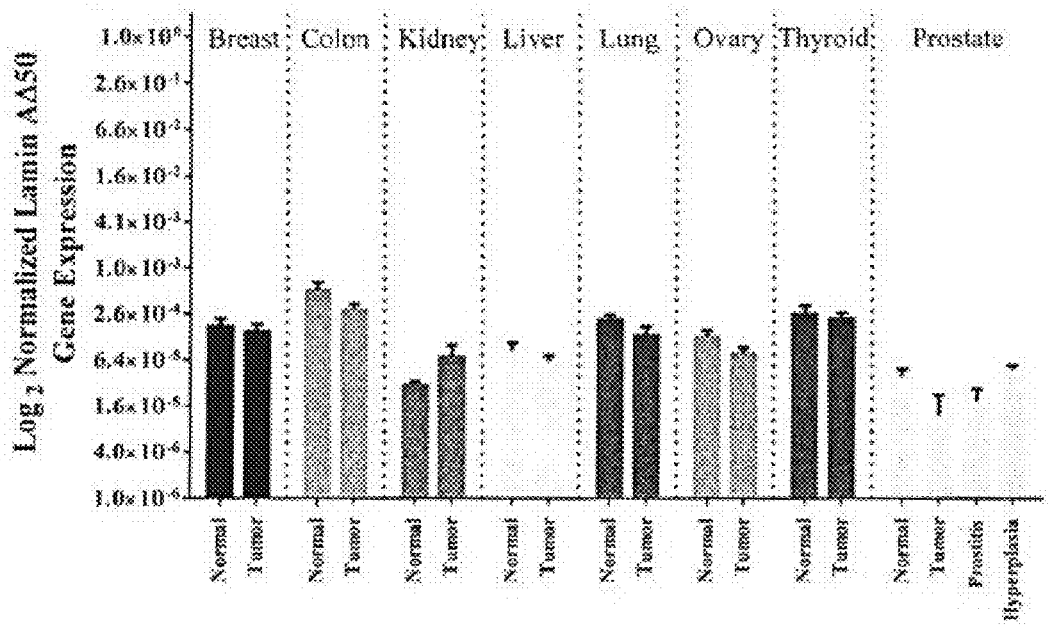

FIGS. 6A-6D show qRT-PCR measurement of relative mRNA expression levels for Lamin A (FIG. 6A); Lamin C (FIG. 6B); Lamin AΔ10 (FIG. 6C) and Progerin (FIG. 6D) in Cancer Survey cDNA arrays (CSRT101) containing eight types of cancers with their corresponding normal tissues. The expression levels of Lamin A/C transcript variants were normalized to the average expression levels of three housekeeping genes. The mean normalized expression levels of Lamin A/C gene transcript variants were calculated using Q-Gene software. A Mann-Whitey Rank Sum Test between normal (n=3) and tumor (n=9) specimens analysis identified a significant difference between normal and tumor samples for Lamin A in adenocarcinoma of colon and carcinoma of thyroid. There was a trend (P=0.064) in liver cancer. The error bars represent the Mean±SEM; *: P<0.05.

Figure 7A:
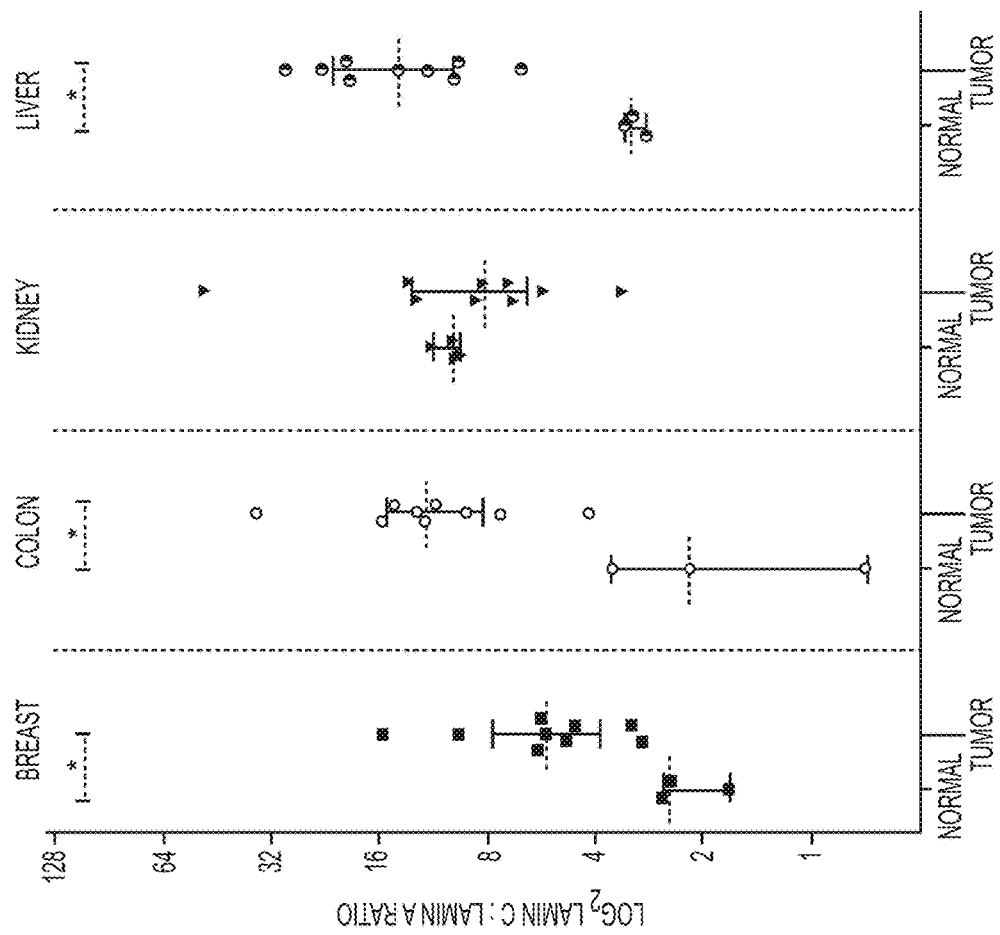
Figure 7B:
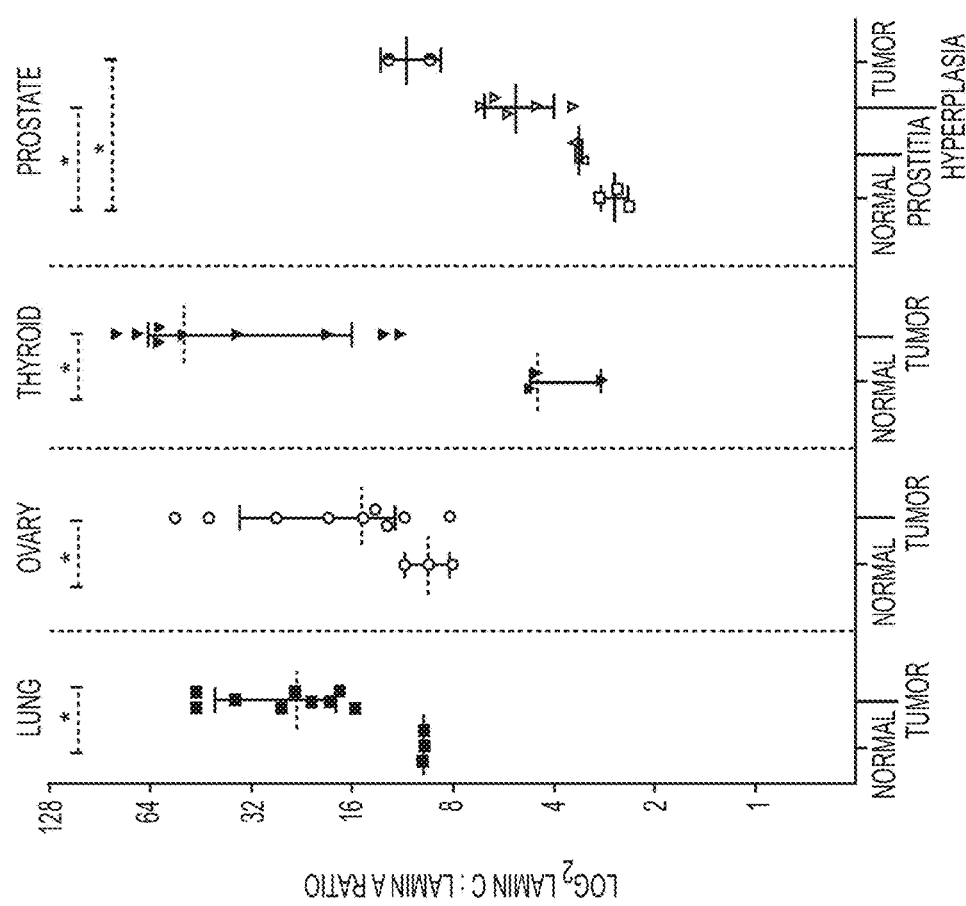

FIGS. 7A-7B show the ratios of Lamin C: Lamin A in various tissues. FIG. 7A shows the Lamin C: Lamin A mRNA ratios in breast, colon, kidney, liver; and FIG. 7B shows the ratios in lung, ovary, thyroid, and prostate cancers. The mean normalized expression levels of Lamin A and Lamin C mRNA was calculated using Q-Gene software. The error bars represent the median (central bar)±IQR. A Mann-Whitney Rank Sum Test analysis, between normal (n=3) and tumor (n=9) specimens for each cancer type, identified a significant difference in Lamin C: Lamin A ratio in breast, colon, liver; lung, ovary, thyroid, and prostate cancers. The error bars represent IQR (Q1-Q3); *: P<0.05.

Figure 8:
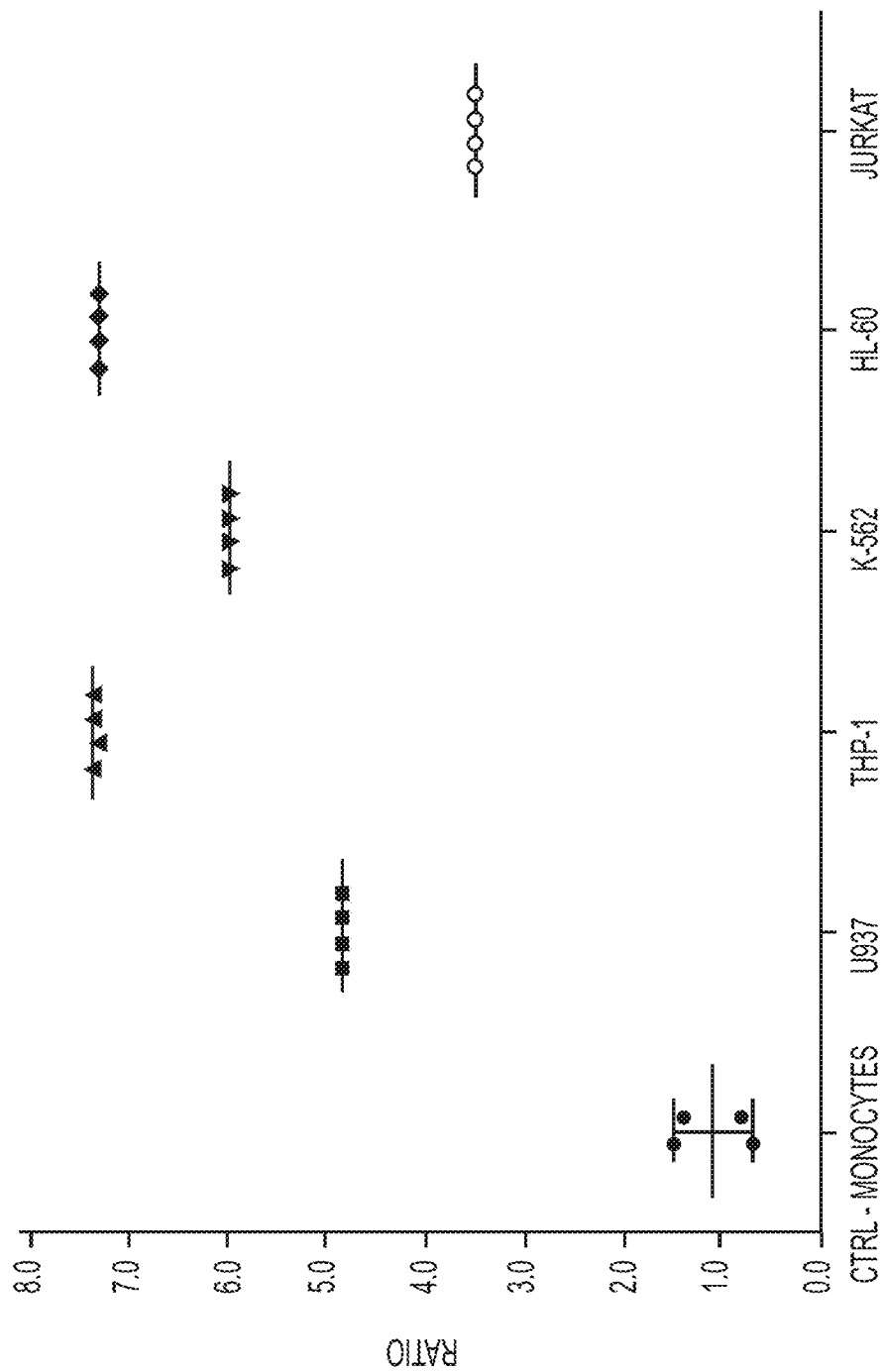

FIG. 8 describes the mRNA ratio of Lamin C:Lamin A in monocytes from normal subjects and several leukemic cell lines (U937 histiocytic lymphoma; THP-1 monocytic leukemia; K562 chronic myelogenous leukemia; HL-60 acute promyelocytic leukemia; and Jurkat acute T-cell leukemia). Normal monocytes isolated from normal subjects had a ratio of <2 whereas other leukemic cell lines had a ratio >2. All cells were grown in RPMI media supplemented with 10% FBS in a $CO_2$ incubator at 37° C. for 4 days.

DETAILED DESCRIPTION OF THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting. Although a number of methods and materials similar or equivalent to those described herein can be used in the practice of the present invention, the preferred materials and methods are described herein.

The methods disclosed herein employ, unless otherwise indicated, conventional techniques of chemistry, molecular biology, microbiology, recombinant DNA and immunology, which are within the capabilities of a person of ordinary skill in the art. Such techniques are explained in the literature, for example, by Green & Sambrook (2012, Molecular Cloning—A Laboratory Manual (4th Ed.), Vols. 1-3, Cold Spring Harbor Laboratory, Cold Spring Harbor, N.Y.); J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, Chapters 9, 13, and 16, John Wiley & Sons, New York, N.Y.); B. Roe, J. Crabtree, and A. Kahn, 1996, DNA Isolation and Sequencing: Essential Techniques, John Wiley & Sons; M. J. Gait (Editor), 1984, Oligonucleotide Synthesis: A Practical Approach, Irl Press; and, D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference in its entirety.

Definitions

The articles "a" and "an" are used herein to refer to one or to more than one (i.e. to at least one) of the grammatical object of the article. By way of example, "an agent" means one agent or more than one agent.

The "Lamin A/C" gene is also known as the LMNA gene. The Lamin A/C gene encodes mRNA that is spliced into several alternative mRNAs which encode different lamin proteins, such as Lamin A or Lamin C.

"Lamin A" and "Lamin C" are structural proteins called intermediate filament proteins. Intermediate filaments provide stability and strength to cells. Lamins A and C are scaffolding (supporting) components of the nuclear envelope, which is a structure that surrounds the nucleus in cells. Specifically, these proteins are located in the nuclear lamina, a mesh-like layer of intermediate filaments and other proteins that is attached to the inner membrane of the nuclear envelope. The nuclear envelope regulates the movement of molecules into and out of the nucleus, and researchers believe it may play a role in regulating the activity (expression) of certain genes. The Lamin A protein must be processed within the cell before becoming part of the lamina. Its initial form, called preLamin A, undergoes a complex series of steps that are necessary for the protein to be inserted into the lamina. Lamin C does not have to undergo this processing before becoming part of the lamina; see http://ghr.nlm.nih.gov/gene/LMNA (last accessed Oct. 13, 2015).

A "Lamin C:Lamin A" ratio describes the proportion of Lamin C mRNA to Lamin A mRNA, or Lamin C protein to Lamin A protein. Other ratios of mRNAs or proteins between the different alternative splice variants of the Lamin A/C gene or between Lamin A/C alternative splice variants and control mRNAs, such as those expressed by housekeeping genes may also be calculated. A "normal" Lamin C to Lamin A ratio refers to that in a control subject not afflicted with cancer or to that found in non-cancerous control cells (e.g., the normal cell type from which the cancer or tumor cell developed). Huang, et al., U.S. Pat. No. 9,150,927, quantified mRNAs encoding insulin receptor A (IR-A) and insulin receptor B (IR-B) and determined the ratio of IR-A to IR-B as a way to classify tumor cells. The molecular biological and statistical methods disclosed therein are incorporated by reference.

A ratio according to the invention may be a reciprocal ratio, such as a ratio of Lamin A to Lamin C nucleic acids or ratio of Lamin A to Lamin C proteins. In this case, samples from normal subjects would exhibit a ratio of >0.5 and the ones from cancerous samples would exhibit a ratio of <0.5.

A "biological sample" refers to a sample obtained from the body, fluids or gases of a subject. Examples include tissue or tumor biopsies, blood, plasma, serum, CSF, lymph, ascites, ductal fluids, mucous, saliva, urine, and other fluids that contain tumor or cancer cells. In cases in which the subject is being diagnosed for cancer, the biological sample obtained from the subject to be diagnosed is typically a biopsy of abnormal tissue suspected of containing cancerous or dysplastic cells, but can be any sample of tissue or cells that contains the expressed biomarkers. The biological sample can be obtained from the subject by conventional techniques. For example, samples of tissue or cells can be obtained by surgical techniques well known in the art. In certain embodiments, the biological sample may comprise a tissue sample including a portion, piece, part, segment, or fraction of a tissue which is obtained or removed from an intact tissue of a subject. Tissue samples can be obtained, for example, from the breast, pancreas, stomach, liver, secretory gland, bladder, lung, prostate gland, ovary, cervix, uterus, brain, eye, connective tissue, bone, muscles, vasculature, skin, oral cavity, tongue, head, neck, or throat. A tissue biopsy may be obtained by methods including, but not limited to, an aspiration biopsy, a brush biopsy, a surface biopsy, a needle biopsy, a punch biopsy, an excision biopsy, an open biopsy, an incision biopsy or an endoscopic biopsy. In certain embodiments, the biological sample is a tumor sample, including the entire tumor or a portion, piece, part, segment, or fraction of a tumor. A tumor sample can be obtained from a solid tumor or from a non-solid tumor, for example, from a squamous cell carcinoma, skin carcinoma, oral cavity carcinoma, head carcinoma, throat carcinoma, neck carcinoma, breast carcinoma, lung carcinoma, basal cell carcinoma, a colon carcinoma, a cervical carcinoma, Kaposi sarcoma, prostate carcinoma, an adenocarcinoma, a melanoma, hemangioma, meningioma, astrocytoma, neuroblastoma, carcinoma of the pancreas, gastric carcinoma, colorectal carcinoma, colon carcinoma, transitional cell carcinoma of the bladder, carcinoma of the larynx, chronic myeloid leukemia, acute lymphocytic leukemia, acute promyelocytic leukemia, multiple myeloma, T-cell lymphoma, B-cell lymphomas, retinoblastoma, sarcoma gallbladder, or bronchial cancer. The tumor sample may be obtained from a primary tumor or from a metastatic lesion.

Cancer or tumor cells may also be identified and isolated from a biological sample and then cultured or passaged prior to detection of the ratio of Lamin C to Lamin A mRNAs or proteins. This may be advantageous when a sample is obtained from a patient undergoing a treatment which could otherwise skew the ratio in tumor or cancer cells not exposed to the treatment or to eliminate background signals from otherwise normal cells in a sample containing tumor or cancer cells.

The terms "tumor," "cancer" and "neoplasia" are used interchangeably and refer to a cell or population of cells whose growth, proliferation or survival is greater than growth, proliferation or survival of a normal counterpart cell, e.g., a cell proliferative, hyperproliferative or differentiative disorder. Typically, the growth is uncontrolled. The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer. Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission. For example, these terms encompass the various types and stages of breast cancer described herein.

In particular, the terms "tumor," "cancer" and "neoplasia" include carcinomas, such as squamous cell carcinoma, adenocarcinoma, adenosquamous carcinoma, anaplastic carcinoma, large cell carcinoma, and small cell carcinoma. These terms include, but are not limited to, breast cancer, prostate cancer, lung cancer, ovarian cancer, testicular cancer, colon cancer, pancreatic cancer, gastric cancer, hepatic cancer, leukemia, lymphoma, adrenal cancer, thyroid cancer, pituitary cancer, renal cancer, brain cancer, skin cancer, head cancer, neck cancer, oral cavity cancer, tongue cancer, and throat cancer. Cancers exemplified herein include breast cancer, leukemia, ovary cancer, prostate cancer, colorectal cancer, thyroid cancer, and liver cancer.

A cancer is "inhibited" or its severity is reduced if at least one symptom of the cancer is alleviated, terminated, slowed, or prevented. As used herein, cancer is also "inhibited" if recurrence or metastasis of the cancer is reduced, slowed, delayed, or prevented.

By "anti-tumor activity" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Such activity can be assessed using animal models.

A kit is any manufacture (e.g., a package, box, envelop, bag or other container or holder) comprising at least one reagent, e.g., a probe or antibody, for specifically detecting the expression of Lamin A and/or Lamin C mRNA or nucleic acids, or Lamin A and/or Lamin C proteins. The kit may be promoted, distributed, or sold as a unit for performing the methods of the present invention. Kits may contain antibodies, for detecting Lamin A or Lamin C proteins; or nucleic acids, such as primers and probes, for detecting Lamin A and Lamin C mRNA or amplified nucleic acids derived therefrom. Control or housekeeping proteins, such as ubiquitin, RBL-13 or β-actin, or antibodies for detecting control proteins, or control nucleic acids, such as probes or primers for amplifying or detecting nucleic acids of ubiquitin, RBL-13 or β-actin may be included.

The terms "antibody" and "antibodies" encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody moiety or radioactive markers.

The term "primer" or "primer pair" as used herein refers to short oligonucleotides (typically 10-30 bp or any intermediate integer value) which are used in PCR to prime a polymerization reaction. Specific primers may be used to select a Lamin A or Lamin C DNA or RNA sequence to be amplified by priming a polymerization at a specific location in the target sequence.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The primers and probes herein may comprise a synthetic nucleic acid sequence or oligonucleotide useful for amplification or detection of polynucleotides encoding Lamin A or Lamin C. It may constitute DNA, RNA, chimeric mixtures or derivatives or modified versions thereof that can be modified at the base moiety, sugar moiety or backbone and may include other appending groups, labels or quenchers, so long as they are still capable of functioning in the desired reaction. The synthetic nucleic acid sequences may comprise at least one modified phosphate backbone—such as phosphorothioate, a phosphorodithioate, a phosphoramidothioate, a phosphoramidate, a phosphordiamidate, a methylphosphonate, an alkyl phosphotriester, and a formacetal or an analogue thereof.

The following primer and probe sequences are referred to herein.

```
Lamin A:
The sequence of the probe is
5'-CGCTGAGTACAACCT-3';             (SEQ ID NO: 9)

The sequence of the forward primer is
5'-GACGAGGATGAGGATGGAGA-3';        (SEQ ID NO: 10)

The sequence of the reverse primer is
5'. GAGTGACCGTGACACTGGAG-3'.       (SEQ ID NO: 11)

Lamin C:
The sequence of the probe is
5'-AGATGACCTGCTCCATCACC-3';        (SEQ ID NO: 12)

The sequence of the forward primer is
5'-GTGGAAGGCACAGAACACCT-3;         (SEQ ID NO: 13)

The sequence of the reverse primer is
5'-GCGGCGGCTACCACTCAC-3'.          (SEQ ID NO: 14)

Lamin AΔ10:
The sequence of the probe is
5'-AGTACAACCTGCGCTCGCGC-3';        (SEQ ID NO: 15)

The sequence of the forward primer is
5'-AACTCCACTGGGGAAGGCTCC-3';       (SEQ ID NO: 16)

The sequence of the reverse primer is
5'-GCTCCTGAGCCGCTGGCAGA-3'.        (SEQ ID NO: 17)

Lamin AΔ50:
The sequence of the probe is
5'-AGCATCATGTAATCTGGGACCT-3';      (SEQ ID NO: 18)

The sequence of the forward primer is
5'-GCGTCAGGAGCCCTGAGC-3;           (SEQ ID NO: 19)

The sequence of the reverse primer is
5'-GACGCAGGAAGCCTCCAC-3'.          (SEQ ID NO: 20)

Ubiquitin:
The sequence of the probe is
5'-CCCACCTCTGAGACGGAGCACCAG-3';    (SEQ ID NO: 21)

The sequence of the forward primer is
5'-ACTACAACATCCAGAAAGAGTCCA-3';    (SEQ ID NO: 22)

The sequence of the reverse primer is
5'-CCAGTCAGGGTCTTCACGAAG-3'.       (SEQ ID NO: 23)

RPL-13:
The sequence of the probe is
5'-CGCAAGCGGATGAACACCAACCCT-3';    (SEQ ID NO: 24)

The sequence of the forward primer is
5'-AACAAGTTGAAGTACCTGGCTTTC-3';    (SEQ ID NO: 25)

The sequence of the reverse primer is
5'-TGGTTTTGTGGGGCAGCATA-3'.        (SEQ ID NO: 26)

β-Actin:
The sequence of the probe is
5'-CGGCTACAGCTTCACCACCACGGC-3';    (SEQ ID NO: 27)

The sequence of the forward primer is
5'-TGACTGACTACCTCATGAAGATCC-3';    (SEQ ID NO: 28)

The sequence of the reverse primer is
5'-CCATCTCTTGCTCGAAGTCCAG-3.       (SEQ ID NO: 29)
```

While this disclosure identifies specific primers and probes that have been found to be particularly sensitive and specific, persons of skill in the art would understand that useful primers include any primers that can prime a polymerase reaction at about the same locations as the exemplary primers disclosed herein. Similarly, additional probes which distinguish between Lamin A and Lamin C or between these variants and other Lamin A/C alternative splice variants may be synthesized that specifically bind to amplified Lamin A or Lamin C target sequence. Generally, longer sequences comprising more complementary residues may contain greater variation.

The skilled artisan will be able to construct primer pairs based on the primer designs disclosed herein which amplify by PCR mRNAs encoding Lamin A or Lamin C or other lamin splice variants, such as primer pairs that respectively anneal to opposite strands of a nucleic acid encoding Lamin A or Lamin C and prime DNA synthesis in the proper direction. These nucleic acid sequences and related sequences described herein can be used in assays to detect and quantify expression of human Lamin A and Lamin C mRNA and nucleic acids in a sample despite the high sequence identity between Lamin A and Lamin C.

The inventor exemplifies herein a quick and sensitive method to determine differential expression of Lamin A and Lamin C mRNA in sample. The methods described using these sequences are quantitatively accurate, allowing them to be used in high throughput and clinical settings.

A. Lamin A Nucleic Acid Sequences

Suitable Lamin A synthetic nucleic acid sequences include the following. A sequence of a Lamin A probe is 5'-CGCTGAGTACAACCT-3' (SEQ ID NO: 9); the sequence of the forward primer is 5'-GACGAGGATGAG-GATGGAGA-3' (SEQ ID NO: 10); the sequence of the reverse primer is 5'. GAGTGACCGTGACACTGGAG-3' (SEQ ID NO: 11).

Synthetic nucleic acids comprising Lamin A nucleic acid sequences may include forward primers targeting exon 10 of the Lamin A/C gene, which is missing from Lamin mRNA splice variant encoding Lamin AΔ10, and a reverse primers targeting the deleted region of exon 11 which is missing in the mRNA splice variants encoding Lamin C and Progerin; or complements thereof. Primers according to the invention may target exon junctions, for example, primers targeting the exon 9-exon 11 junction may be employed to quantitate lamin AΔ10. Such sequences, which are capable of hybridizing to Lamin A/C mRNA splice variants under stringent conditions can be used in polymerase-based amplification and detection such as quantitative polymerase chain reaction (qPCR) (also known as real-time PCR or kinetic PCR) to determine the level of expression of Lamin A mRNA in a sample. A synthetic nucleic acid comprising a sequence that hybridizes under stringent conditions of Lamin A mRNA can include 10, 11, 12, 13, 14, 15, 16, 17, 18, 19, 20, 21, 22, 23, 24, 25, 26, 27, 28, 29 or 30 consecutive nucleotides, wherein the synthetic nucleic acid sequence comprises at least 10, 11, 12, 13, 14, 15, 16, 17, 18, 19, 20, consecutive nucleotides of the sequences of SEQ ID NOS: 9, 10 or 11 or their complements.

B. Lamin C Nucleic Acid Sequences

Suitable Lamin C synthetic nucleic acid sequences include a probe sequence that is 5'-AGATGACCTGCTC-CATCACC-3' (SEQ ID NO: 12); a sequence of the forward primer is 5'-GTGGAAGGCACAGAACACCT-3 (SEQ ID NO: 13); a sequence of the reverse primer is 5'. GCGGCG-GCTACCACTCAC-3' (SEQ ID NO: 14).

Synthetic nucleic acids comprising Lamin C nucleic acid sequences may include forward primer in exon 7 of the Lamin A/C gene, and a reverse primer in the 3'UTR in exon 10 of the Lamin A/C gene. A synthetic nucleic acid comprising a sequence that hybridizes under stringent conditions of Lamin C mRNA can include 10, 11, 12, 13, 14, 15, 16, 17, 18, 19, 20, 21, 22, 23, 24, 25, 26, 27, 28, 29 or 30 consecutive nucleotides, wherein the synthetic nucleic acid sequence comprises at least 10, 11, 12, 13, 14, 15, 16, 17, 18, 19, 20, consecutive nucleotides of the sequences of SEQ ID NOS: 12, 13 or 14 or their complements.

Useful synthetic nucleic acid sequences also include variants of the sequences disclosed above or sequences that are substantially similar to the nucleic acids disclosed herein. Variants include sequences that are altered by one or more bases, such as 2, 3, 4, 5, 6, 7, 8, 9 or 10 bases, but can still anneal to the specific locations on the Lamin A or Lamin C target sequence of interest. The term "substantially similar" when used in relation to annealing or hybridization, means that a synthetic nucleic acid sequence, such as a primer, should be sufficiently complementary to hybridize or anneal to its respective nucleic acid under stringent conditions. The synthetic nucleic acid sequence need not reflect the exact sequence of its respective nucleic acid, and can, in fact, be "degenerate." Non-complementary bases or other sequences may be interspersed into the synthetic nucleic acid sequence, provided that the synthetic nucleic acid sequence has sufficient complementarity with the sequence to permit hybridization. Thus, by way of example, the primers used for PCR amplification may be selected to be "substantially" complementary to the specific sequence to be amplified.

As used herein, the term "hybridization" refers to the process by which a strand of nucleic acid joins with a complementary strand through base pairing as well as the process of amplification as carried out in, for example, PCR technologies. Nucleotide sequences that are capable of hybridizing to the complement of a given nucleotide sequence are generally functionally equivalent and can be substituted for that nucleotide sequence for the purposes of the methods described herein.

"Stringent hybridization conditions" may be any of low stringency conditions, moderately stringent conditions and highly stringent conditions. Generally, "low stringency conditions" are, for example: hybridization in a solution comprising 5×SSC; 5× Denhart's solution; 0.5% (w/v) SDS; and 50% (w/v) formamid; at 32° C. "Moderately stringent conditions" are, for example: hybridization in a solution comprising 5×SSC; 5× Denhart solution; 0.5% (w/v) SDS; and 50% (w/v) formamide; at 42° C. "Highly stringent conditions" are, for example: hybridization in a solution comprising 5×SSC; 5× Denhart's solution; 0.5% (w/v) SDS; and 50% (w/v) formamide; at 50° C. Hybridization stringency is affected by a plurality of factors such as temperature, nucleic acid concentration, nucleic acid length, ion strength, time, and salt concentration. These are merely exemplary conditions that will produce the different levels of stringency. Those skilled in the art would be able to realize similar stringency by suitably adjusting hybridization conditions, including by adjusting such conditions for the desired stringency in a PCR reaction.

Synthetic nucleic acid sequences may be derived by cleavage of a larger nucleic acid fragment using non-specific nucleic acid cleaving chemicals or enzymes or site-specific restriction endonucleases; or by synthesis by standard methods known in the art, e.g. by use of a commercially available automated DNA synthesizer and standard phosphoramidite chemistry. One method for synthesizing oligonucleotides on a modified solid support is described in U.S. Pat. No. 4,458,066 which is incorporated by reference.

Once a desired synthetic nucleic acid is synthesized, it can be cleaved from a solid support on which it was synthesized and treated, by methods known in the art, to remove any protecting groups present. The synthetic nucleic acids may then be purified by any method known in the art, including extraction and gel purification. The concentration and purity of the oligonucleotide may be determined by, for example, examining the oligonucleotide on an acrylamide gel, by HPLC, or by measuring the optical density at 260 nm in a spectrophotometer.

The synthetic nucleic acid sequences of the invention can be used in any assay which is used to determine for the presence of the expression of Lamin A and Lamin C mRNAs. In one example, isolated nucleic acids such as disclosed herein can be used in an amplification process. Amplification refers to a process for multiplying nucleic acid strands in vitro. An exemplary technique is PCR, which exponentially amplifies nucleic acid molecules. PCR is described in U.S. Pat. No. 4,683,195 and U.S. Pat. No. 4,683,202 which are each incorporated by reference. PCR is extensively used for specific detection and quantification of target nucleic acid sequences polynucleotides and is a standard method in molecular biology. PCR can be used to determine expression of Lamin A and Lamin C mRNAs in a test sample. The method uses a pair of isolated nucleic acid sequences, "primers", which specifically anneal to specific locations on the Lamin A or Lamin C DNA molecule. Lamin A or Lamin C DNA is heat denatured and two oligonucleotides that bracket the target sequence on opposite strands of the DNA to be amplified, are hybridized. These oligonucleotides become primers for use with DNA polymerase. The DNA is copied by primer extension to make a second copy of both strands. By repeating the cycle of heat denaturation, primer hybridization and extension, the target Lamin A or Lamin C DNA can be amplified a million fold or more in about two to four hours. PCR is a molecular biology tool which must be used in conjunction with a detection technique to determine the results of amplification. An advantage of PCR is that it increases sensitivity by amplifying the amount of target DNA by 1 billion fold in approximately 0.5 to 4 hours.

As discussed below and illustrated in the examples a useful method of using Lamin A and Lamin C primers and probes is quantitative PCR. Quantitative PCR refers to methods where the PCR reaction is combined with fluorescence chemistry to enable real-time monitoring of the amplification reaction using detection of a fluorescent light signal. In one example the method uses a sequence nonspecific fluorescent reporter dye such as SYBR green; Wittwer C T et al., Biotechniques 22(1):176-81 (1997). In another example, the method uses a sequence specific fluorescent reporter such as a TAQMAN probe; Heid, et al., Genome Res. 6(10):986-94 (1996). During execution of the PCR cycling program, the samples are excited using a light source. A fluorescent signal, indicating the amount of PCR amplification product produced, is monitored in each reaction well using a photodetector or CCD/CMOS camera. By monitoring the fluorescence in the sample during the reaction precise quantitative measurements can be made. The probe based PCR method is considered to more accurate than the SYBR green method. PCR or qPCR is typically performed in plastic 96 or 384 well microtiter plates, each reaction having a volume in the order of 5-50 µl PCR can however be carried out in very small (nanoliter) volumes. Other quantification strategies may be employed such as Molecular Beacon Probes, see Tyagi et al., "Molecular Beacons: Probes that Fluoresce upon Hybridization," Nature Biotechnology 14: 303-308 (1996); or Situma et al., "Immobilized molecular beacons: A new strategy using UV-activated poly(methyl methacrylate) surfaces to provide large fluorescence sensitivities for reporting on molecular association events." Analytical Biochemistry 363: 35-45 (2007). Each reference described above is incorporated by reference.

Real-time PCR can be performed to detect a single gene or RNA molecule, however, multiple genes or RNA molecules may be detected in one reaction, i.e., by multiplexing. Detection of nucleic acids by multiplexing is described by Kosman, et al., "Multiplex Detection of RNA Expression in *Drosophila* Embryos," Science, 305: 846 (2004); Sakai et al., "Quick detection of herpes viruses from skin vesicles and exudates without nucleic acid extraction using multiplex PCR," BioScience Trends 2(4):164-168 (2008); or Gu et al. "Multiplexed, Real-Time PCR for Quantitative Detection of Human Adenovirus", Journal of Clinical Microbiology, vol. 41(10): 4636-4641 (2003) which are incorporated by reference. For example, one or more lamin genes or mRNAs may be detected simultaneously with one or more housekeeping genes or mRNAs in a single reaction.

The methods described herein provide a method for the reproducible and robust amplification of small amounts of DNA which contain Lamin A or Lamin C mRNA or nucleic acids. Performing qPCR using the nucleic acid primers described herein can specifically detect Lamin A or Lamin C mRNA from 1 copy of RNA/DNA to millions of copies. A biological sample may comprise RNA that in some implementations of the method is first transcribed into cDNA. Total cellular RNA, cytoplasmic RNA, or poly(A)+RNA may be used. Methods for preparing total and poly(A)+RNA are well known and are described generally in Green & Sambrook, Molecular Cloning—A Laboratory Manual (4th Ed.), Vols. 1-3, Cold Spring Harbor Laboratory, Cold Spring Harbor, N.Y. (2012) and Ausubel et al., eds., Current Protocols in Molecular Biology, vol. 2, Current Protocols Publishing, New York (1994). Total RNA may be prepared by the techniques described by Methods in Enzymology, vol. 530 (2013); Chirgwin et al., Methods in Enzymology. 152: 219-226. (1987); Laboratory Methods in Enzymology: RNA Chomczynski & Sacchi, Anal Biochem. April; 162(1):156-9. (1987), Green & Sambrook (2012), or Farrell Jr. (1993). The above references are each incorporated by reference. A number of high quality commercial kits for RNA isolation or purification are also available.

The integrity of total RNA may be checked using various methods that are known in the art. By way of example, the RNA may be analyzed using RNA gel electrophoresis (e.g. formaldehyde/agarose gel), or Agilent LabChip. For mammalian total RNA, two bands at approximately 4.5 and 1.9 kb should be visible; these bands represent 28S and 18S ribosomal RNA respectively, and the ratio of intensities of these bands should typically be 1.5-2.5:1.

RNA purification kits for microscale RNA preparation are available from a number of commercial suppliers (for example Absolutely RNA™ Nanoprep, Stratagene; PicoPure™, Arcturus; RNeasy™, Qiagen; RNAqueous™ Microkit, Ambion).

The cDNA synthesis oligonucleotide for first strand cDNA synthesis may be hybridized to RNA in a suitable buffer at a temperature between about 60° C. and 90° C., preferably about 70° C. for about 5 minutes, followed by cooling to about 4° C., before the reverse transcriptase is added. Following the hybridization of the cDNA synthesis oligonucleotide to RNA, a first cDNA strand is synthesized. This first strand of cDNA is preferably produced through the process of reverse transcription, wherein DNA is made from RNA, utilizing reverse transcriptase following methods that are familiar to a person skilled in the art.

Any reverse transcriptase may be used to transcribe RNA to DNA as long as the enzyme adds deoxyribonucleotides to the 3' terminus following extension (Varmus, Science 240: 1427-1435 (1988)) and the enzyme lacks RNaseH activity. Preferably, the reverse transcriptase lacks RNaseH activity but retains wild-type polymerase activity such that longer cDNAs can be synthesized. The reverse transcriptase may be Moloney Murine Leukemia virus (MMLV) reverse transcriptase or a mutant thereof. The reverse transcriptase may be Avian Myeloblastosis Virus (AMV) reverse transcriptase or a mutant thereof.

The amount of reverse transcriptase employed may vary as will be appreciated by a person skilled in the art. The reverse transcription is performed by incubation for, for example, approximately 1 hour with reverse transcriptase at an appropriate temperature, which must be in a temperature range in which the reverse transcriptase retains enzyme activity. The reaction may be performed between 37° C. and 55° C., preferably between 37° C. and 42° C. Most preferably, the reaction is performed at optimal enzyme activity—such as at about 42° C. The reverse transcription reaction may be terminated by heating the reaction mixture to 95° C. for about 5 minutes to inactivate the enzyme, optionally, followed by chilling on ice.

Methods of Detecting and/or Quantifying Lamin A and Lamin C mRNA Expression.

A preferred approach is to use a real-time polymerase chain reaction, also called quantitative real time polymerase chain reaction (variously abbreviated Q-PCR, qPCR, qrt-PCR, or RTQ-PCR) or kinetic polymerase chain reaction (KPCR). Frequently, real-time PCR is combined with reverse transcription to quantify messenger RNA and non-coding RNA in cells or tissues. Reverse transcription PCR permits starting from an RNA containing sample without prior preparation of cDNA. Real-time reverse-transcription PCR is often denoted as qRT-PCR, RRT-PCR, or RT-rt PCR. It enables both detection and quantification (as absolute number of copies or relative amount when normalized to DNA input or additional normalizing genes) of one or more specific sequences in a DNA sample.

The procedure follows the general course of a polymerase chain reaction. However, amplified DNA is detected as the reaction progresses in real time. Two common methods for detection of products in real-time PCR are: (i) non-specific fluorescent dyes that intercalate with any double-stranded DNA, and (ii) sequence-specific DNA probes consisting of oligonucleotides that are labeled with a fluorescent reporter which permits detection only after hybridization of the probe with its complementary DNA target.

Fluorescent reporter probes detect only the DNA containing the probe sequence; therefore, use of the reporter probe significantly increases specificity, and enables quantification even in the presence of non-specific DNA amplification. Fluorescent probes can be used in multiplex assays—for detection of several genes in the same reaction—based on specific probes with different-colored labels, provided that all targeted genes are amplified with similar efficiency.

The method generally uses a DNA-based probe with a fluorescent reporter at one end and a quencher of fluorescence at the opposite end of the probe. The close proximity of the reporter to the quencher prevents detection of its fluorescence; breakdown of the probe by the 5' to 3' exonuclease activity of a polymerase separates the reporter from the quencher and thus allows unquenched emission of fluorescence. An increase in the product targeted by the reporter probe at each PCR cycle therefore causes a proportional increase in fluorescence due to the breakdown of the probe and release of the reporter.

A PCR sample is prepared as usual, and the reporter probe is added. As the reaction commences, during the annealing stage of the PCR both probe and primers anneal to the DNA target.

Polymerization of a new DNA strand is initiated from the primers, and once the polymerase reaches the probe, its 5'-3'-exonuclease degrades the probe, physically separating the fluorescent reporter from the quencher, resulting in an increase in fluorescence. Fluorescence is detected and measured in the real-time PCR thermocycler, and its geometric increase corresponding to exponential increase of the product is used to determine the threshold cycle (CT) in each reaction.

Relative concentrations of DNA present during the exponential phase of the reaction can be determined by plotting fluorescence against cycle number on a logarithmic scale (so an exponentially increasing quantity will give a straight line). A threshold for detection of fluorescence above background is determined. The cycle at which the fluorescence from a sample crosses the threshold is called the cycle threshold, Ct. The quantity of DNA theoretically doubles every cycle during the exponential phase and relative amounts of DNA can be calculated, e.g. a sample whose Ct is 3 cycles earlier than another's has $2^3=8$ times more template. Since all sets of primers don't work equally well, one has to calculate the reaction efficiency first. Thus, by using this as the base and the cycle difference C(t) as the exponent, the difference in starting template can be calculated as $(2\times \text{eff})^{Ct}$.

Amounts of RNA or DNA can then be determined by comparing the results to a standard curve produced by real-time PCR of serial dilutions (e.g., undiluted, 1:4, 1:16, 1:64) of a known amount of RNA or DNA. To accurately quantify gene expression, the measured amount of RNA from the gene of interest is divided by the amount of RNA from a housekeeping gene measured in the same sample to normalize for possible variation in the amount and quality of RNA between different samples. This normalization permits accurate comparison of expression of the gene of interest between different samples, provided that the expression of the reference gene used in the normalization is very similar across all the samples. Mechanism based qPCR quantification methods have also been described, such as MAK2. They do not require a standard curve for quantification. These mechanism based methods use knowledge about the polymerase amplification process to generate estimates of the original sample concentration.

Real-time PCR can be used to determine relative quantities and absolute quantities. Relative quantification measures the fold-difference (2×, 3×, etc.) in the target amount. Absolute quantification gives the exact number of target molecules present by comparing with known standards Classifying a Cancer or Tumor Using the Ratio of Lamin C to Lamin A mRNAs.

A method of classifying a tumor can comprise providing a tumor sample; contacting the sample with a synthetic Lamin C and Lamin A specific oligonucleotides; and detecting or quantifying the amount s of Lamin C and Lamin A mRNAs in the tumor. The value obtained in the tumor may be compared to a control tissue sample or to a population average for normal tissue. For example, a breast cancer tumor sample may be compared to a sample from non-affected breast of the same patient or to a population average for non-affected breast tissue. An elevated ratio of Lamin C mRNA or protein to Lamin A mRNA or protein is indicative of cancer or higher risk of cancer.

A method of classifying a cancer or tumor can include determining the relative expression levels of Lamin A and Lamin C mRNAs. The relative expression can be described as a ratio of Lamin C:Lamin A mRNA, or as a percentage as a proportion of the total mRNA encoded by the Lamin A/C gene, e.g., % Lamin C and % Lamin A mRNA. The relative expression of Lamin C and Lamin A can also be described by the differential of the threshold cycles in a qPCR, e.g. (Lamin C$\Delta$Ct)−(Lamin A$\Delta$Ct)=A$\Delta$Ct, the ratio of Lamin C mRNA to Lamin A mRNA in the sample being approximately equal to $2^{-\Delta\Delta Ct}$. For $\Delta$Ct calculation, the experimental Ct values can be normalized against an internal standard. For example, a mean of in-sample (i.e., obtained from the same sample as Lamin C and/or Lamin A expression) Ct values of a gene expression panel, such as the average Ct of one or more housekeeping genes, can be used for normalization of Ct values for Lamin C and Lamin A to calculate ΔCt values.

As an example, Lamin C and Lamin C mRNA ΔCt values may be determined for normal tissue of any given type. Tissue samples determined to have (Lamin C ΔCt)−(Lamin A ΔCt) differentials that are more than 1, 2, 3 or more standard deviations below the mean value may be classified as having disproportionate levels of Lamin C expression relative to Lamin A expression. By contrast, a positive ΔCt differential indicates a disproportionate level of Lamin A expression. Lamin C:Lamin A ΔCt differentials can be determined in normal and primary tumor samples. A mean Lamin C:Lamin A ΔΔCt+0.95% CI is determined for a group of normal subjects and a mean Lamin C:Lamin A ΔΔCt differentials.±0.95% CI is determined for a group of subjects having a tumor. Based on these data thresholds are set for different confidence intervals. A skilled practitioner may adjust the threshold anywhere in the range between mean values to balance the needs of the classification to be more or less inclusive.

Relative Lamin C and Lamin A mRNA or protein expression levels in tissues may be used as a predictor of cancer proliferation, particularly in combination with other predictors of cancer proliferation, for example to determine a proliferation score. Predicted proliferation rates can provide useful information on prognosis and aggressiveness of individual cancers. The data above illustrate a positive correlation between the Lamin C:Lamin A ΔCt differential and the proliferation score. Thus, a method for scoring tumor tissue may comprise determining the relative proportion of Lamin C and Lamin A expression and assigning a proliferation score based at least in part upon the relative expression of Lamin C and Lamin A mRNAs or proteins.

Tumor samples for classification using these methods can be any appropriate tumor sample including a sample from a lung, breast, prostate, colon, ovary, pancreas, brain, esophagus, endometrium, cervix, gastrointestinal tract or skin. Tumor samples can be taken from any patient where the tumor activity is associated with altered expression of Lamin A or Lamin C. For example, the tumor can be a non-solid tumor such as leukemia, multiple myeloma or lymphoma, or can be a solid tumor, for example bile duct, bone, bladder, brain/CNS, breast, colorectal, cervical, endometrial, gastric, head and neck, hepatic, lung, muscle, neuronal, esophageal, ovarian, pancreatic, pleural/peritoneal membranes, prostate, renal, skin, testicular, thyroid, uterine and vulval tumors. In one example, the tumor is a tumor of the breast.

A non-limiting example of this method for classifying a cancer or tumor comprises:

(a) determining a ratio of Lamin C mRNA to Lamin A mRNA in a biological sample of a normal tissue, determining a ratio of Lamin C mRNA to Lamin A mRNA in a biological sample of at least one cancer or tumor tissue of the same type as said normal tissue, and identifying at least one qualitative or quantitative phenotypic difference between the normal cell and tumor cells that correlates with a difference between the Lamin C mRNA to Lamin A mRNA ratio in said cells, thus classifying a phenotype of the cancer or tumor cell based on said ratio;

(b) determining a ratio of Lamin C protein to Lamin A protein in a biological sample of a normal tissue, determining a ratio of Lamin C to Lamin A proteins in a biological sample of at least one cancer or tumor tissue of the same type as said normal tissue, and identifying at least one qualitative or quantitative phenotypic difference between the normal cell and tumor cells that correlates with a difference between the Lamin C to Lamin A ratio in said cells, thus classifying a phenotype of the cancer or tumor cell based on said ratio.

Methods for Prognosing, Characterizing, or Subgrouping Cancer or Tumor Patients

A subject having cancer may have the Lamin C:Lamin A ratio determined for the cancer. The particular type of cancer, such as breast cancer, can be classified or staged as described above, and the subject prognosed, characterized or grouped based on these data. This process permits practitioners to select appropriate treatments, kinds of drugs, drug doses and other treatment regimens targeted to the classified or staged tumor or cancer.

A treatment may involve administering an agent that modulates Lamin A or Lamin C expression, such as one that increases the transcription of Lamin A or one that decreases the expression of Lamin C relative to Lamin A. A subject exhibiting a greater degree of elevation of a Lamin C to Lamin A ratio compared to a normal, non-cancer subject may be more likely to benefit from drugs and other agents which decrease this ratio or normalize it closer to the ratio exhibited in normal, non-cancer subjects.

In a specific example, a practitioner may pre-select a particular Lamin A or Lamin C agonist or antagonist based on the determination of the ratio of Lamin C to Lamin A mRNA, or on the ratio of Lamin C to Lamin A proteins in a sample. The identification of a tumor that has been determined to overexpress Lamin C relative to Lamin A or under-express Lamin A relative to Lamin C provides the opportunity to select patients that will most likely have increased responsiveness to a Lamin C antagonist or a Lamin A agonist.

Such methods may also be used to convert a tumor or cancer cell into a cell that has a more normal ratio of Lamin C to Lamin A mRNA or protein for that particular cell type which may also be reflected in development of a less cancerous phenotype such as a more normal rate of proliferation, apoptotic capacity, restoration of cell cycle checkpoints found in normal cells, and development of drug sensitivity. In contrast, a reciprocal method may be used to identify agents that increase the ratio of Lamin C to Lamin A mRNA or protein compared to their effects on control cells. Such a method can be used to exclude drugs or agents that elevate this ratio from treatment regimens for particular tumor or cancer patients.

Methods for Screening Methods for Drugs, Nucleotides, Immune Response Modifiers, Small Molecules, Radiation, and Other Agents that Normalize a Lamin C to Lamin a Ratio.

A representative method for identifying a modulator of Lamin C or Lamin A expression involves contacting a cell in vitro or in vivo with a test agent and determining whether the agent causes an increase or decrease in the ratio of Lamin C to Lamin A mRNA or protein expression. An agent that decreases the ratio of Lamin C to Lamin A mRNA or protein toward that exhibited by normal cells of the same cell type is then selected as an anticancer agent. Potential modulators of expression or cellular levels of Lamin A and Lamin C mRNA and proteins include anticancer drugs, small molecules, antisense nucleic acids, antibodies or antibody fragments, chemokines or other immune response modifiers, as well as physical agents such as radiation and heat.

Another embodiment of the invention is a method of identifying and treating a patient having a tumor or cancer who is likely to have a heightened therapeutic response to an anticancer agent based on the characterization or classification of the tumor or cancer having the detected ratio of Lamin C to Lamin A mRNA or protein.

A patient having a heighted response is one that will respond, or respond more positively, following administration of a particular anticancer therapy, including administration of modulators of Lamin C or Lamin A mRNA or protein expression or modulators of intracellular levels Lamin C or Lamin A mRNA and proteins (e.g., agents that increase turnover of Lamin A or Lamin C proteins or which destabilize or inactive lamin mRNAs). Whether a patient is a responder can be determined by measuring objective tumor responses according to the Union International Contre le Cancer/World Health Organization (U ICC/WHO) criteria. The criteria are categorized as follows: complete response (CR): no residual tumor in all evaluable lesions; partial response (PR): residual tumor with evidence of chemotherapy-induced 50% or greater decrease under baseline in the sum of all measurable lesions and no new lesions; stable disease (SD): residual tumor not qualified for CR; and progressive disease (PD): residual tumor with evidence of 25% or greater increase under baseline in the sum of all measurable lesions or appearance of new lesions. As defined herein non-responders are PD. The methods are particularly effective for determining those patients that are CR or PR. The methods thus permit improved prognosis and quality of life of cancer patients by matching the treatments to individual patients and so making more effective use of the types of Lamin C or Lamin A modulators available.

In another embodiment the invention is directed to a kit for detecting the presence of Lamin A mRNA or Lamin C mRNA or corresponding amplified nucleic acids in a biological sample may comprise a Lamin A and/or Lamin C probe or primer. Materials for use in the methods described herein are ideally suited for preparation of kits. For example, the kit can comprise nucleic acid sequences as disclosed herein that are capable of detecting Lamin A mRNA or Lamin C mRNA in a tumor sample; a control sample; and instructions relating to how to detect the cell surface receptor. Such a kit may comprise containers, each with one or more of the various reagents (typically in concentrated form) utilized in the methods, including, for example, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more oligonucleotides. Oligonucleotides in containers can be in any form—lyophilized or in solution, such as in a distilled water, normal saline solution or buffered solution. Oligonucleotides ready for use in the same amplification reaction can be combined in a single container or can be in separate containers. The kit optionally further comprises in a separate container an RNA polymerase specific to the RNA polymerase promoter, and/or a buffer for PCR, and/or a DNA polymerase. The kit optionally further comprises a control nucleic acid. A set of instructions will also typically be included.

Other Aspects of the Invention

The present invention is based, in part, on the identification of an elevated ratio of Lamin C mRNA to Lamin A mRNA in cancer cells as compared to this ratio in normal, non-cancerous cells. The elevated expression of this ratio, as calculated by relative proportions of mRNA, nucleic acids or proteins, in cancer cells correlates with the cancerous state of the tissue. The invention provides compositions, kits, and methods for assessing the cancerous state of cells, such as cells obtained from a human biopsy, cultured human cells, archived or preserved human cells, as well as for treating patients afflicted with cancer characterized by an elevated Lamin C to Lamin A ratio.

The compositions, kits, and methods of the invention have the following uses, among others: assessing whether a patient is afflicted with cancer; assessing the stage of cancer in a human patient; assessing the grade of cancer in a patient; assessing the benign or malignant nature of cancer in a patient; assessing the metastatic potential of cancer in a patient; determining if cancer has metastasized; predicting the clinical outcome of a cancer patient; assessing the histological type of neoplasm associated with cancer in a patient; making antibodies, antibody fragments or antibody derivatives that are useful for treating cancer and/or assessing whether a patient is afflicted with cancer; assessing the presence of cancer cells; assessing the efficacy of one or more test compounds for inhibiting cancer in a patient; assessing the efficacy of a therapy for inhibiting cancer in a patient; monitoring the progression of cancer in a patient; selecting a composition or therapy for inhibiting cancer in a patient; treating a patient afflicted with cancer; inhibiting cancer in a patient; assessing the carcinogenic potential of a test compound; and preventing the onset of cancer in a patient at risk for developing cancer.

The invention thus includes a method of assessing whether a patient is afflicted with cancer which includes assessing whether the patient has pre-metastasized cancer. This method comprises comparing the Lamin C to Lamin A ratio (mRNA, nucleic acid or protein-based) in a patient sample and the normal level of expression of this ratio in a control, e.g., an otherwise similar noncancerous sample. A significantly higher level of expression of the ratio in the patient sample as compared to the normal level is an indication that the patient is afflicted with cancer.

One aspect of the invention is a method for diagnosing a cancer or tumor comprising quantitatively detecting mRNA encoding Lamin A and mRNA encoding Lamin C in a biological sample, selecting a subject having a cancer or tumor, when a ratio of Lamin C mRNA to Lamin A mRNA is elevated compared to the ratio in a control biological sample from a subject who does not have cancer or a tumor. Such a method can be applied to diagnosis or breast cancer, leukemia, ovary cancer, prostate cancer, colorectal cancer, thyroid cancer, or liver cancer.

An elevated ratio of Lamin C mRNA to Lamin A mRNA is indicative of the presence of cancer. Such an elevation is made in comparison to a control level, such as that obtained from a subject prior to development of cancer or from one or more control subjects who do not have cancer. Elevations of the ratio above normal or control values may range from 1, 5, 10, 20, 30, 40, 50, 60, 70, 80, 90, 100, 150, 200, 250, 300, 350, 400, 450, 500% or more.

Methods for quantitatively detecting mRNAs are known. These include real-time polymerase chain reaction and real-time reverse transcription polymerase chain reaction methodologies. These methods can detect Lamin A and Lamin C as well as other splice variants of Lamin A/C mRNA by contacting a biological sample or nucleic acids prepared from a biological sample with primer sets that specifically amplify and distinguish between different Lamin A/C splice variants. A ratio of Lamin C to Lamin A mRNA is determined based on quantifying the relative amplification of these splice variants in a particular biological sample.

Representative primer sets for Lamin A and Lamin C include a primer set for detecting Lamin A nucleic acid that comprises a forward primer targeting exon 10 which is missing in Lamin AΔ10 and a reverse primer targeting a deleted region of exon 11 which is missing in Progerin and Lamin C; and/or where a primer set for detecting Lamin C nucleic acid comprises a forward primer in exon 7 and a reverse primer located in a Lamin C specific 3'UTR in exon 10.

Lamin A and Lamin C specific primer sets are also used for quantifying these splice variants using the TaqMan or Molecular Beacons quantitative real-time polymerase chain reaction. Representative primers and probes useful for amplifying Lamin A and Lamin C mRNAs and quantitatively detecting the amplified nucleic acids include those using a Lamin A probe that comprises 5'-CGCTGAGTA-CAACCT-3' (SEQ ID NO: 9); a Lamin A forward primer that comprises 5'-GACGAGGATGAGGATGGAGA-3' (SEQ ID NO: 10); and a Lamin A sequence of the reverse primer that comprises 5'-GAGTGACCGTGACACTG-GAG-3' (SEQ ID NO: 11); and those using a Lamin C probe comprising 5'-AGATGACCTGCTCCATCACC-3' (SEQ ID NO: 12); a Lamin C forward primer comprising 5'-GTG-GAAGGCACAGAACACCT-3 (SEQ ID NO: 13); and a Lamin C the reverse primer comprising 5'-GCGGCGGC-TACCACTCAC-3' (SEQ ID NO: 14).

Subjects identified as having an abnormal ratio of Lamin C to Lamin A mRNAs are selected for further diagnosis and treatment. Such a subject may be treated by administering an anti-cancer or anti-tumor drug, radiation, tumor mass reduction, such as surgical removal of tumor tissue, immune response modifier, chemokine therapy, gene therapy, antibody or T-cell therapy, or other therapeutic agent for treatment of cancers or tumors exhibiting an abnormal Lamin C to Lamin A ratio compared to this ratio in non-cancerous control cells or control subjects who do not have cancer.

Determination of an abnormal ratio of Lamin C to Lamin A mRNA may also be used to monitor a subject at risk of developing a tumor or cancer, for example, based on prior diagnosis, history or genetic predisposition, a subject who is at risk of relapse of a prior diagnosed cancer, or a subject having cancer or undergoing treatment for cancer. Generally, a significantly higher level of the ratio of Lamin C to Lamin A (mRNA or protein-based) in a sample at a subsequent time point from that of the sample at the first time point is an indication that a cancer has progressed, whereas a significantly lower level of the ratio is an indication that the cancer has regressed.

Such a ratio is longitudinally measured at different time points to determine progression or regression of a cancer or increased or decreased risk at developing or experiencing a relapse of cancer. For example, the Lamin C to Lamin A mRNA ratio may be measured before, during and after treatment with a particular anticancer agent or regimen to assess efficacy of the treatment, for example by reduction of tumor burden or other indicators. An increasingly abnormal ratio is indicative of cancer progression or risk of developing or relapsing with cancer. A ratio trending towards normal is indicative of decreased risk or efficacy of the treatment. Longitudinal measurements of this ratio may also be routinely made, for example, during periodic physical examinations at monthly, quarterly, semiannual or annual intervals. Such a method of monitoring may be used to assess risk and efficacy of treatment for breast cancer, leukemia, ovary cancer, prostate cancer, colorectal cancer, thyroid cancer, liver cancer as well as other types of cancers exhibiting an abnormal ratio of Lamin C mRNA to Lamin A mRNA.

Treatment regimens may involve increasing, maintaining or decreasing a dose of an anti-cancer or antitumor drug, radiation, immune response modifier, or other therapeutic agent being administered to the subject based on whether the tumor has progressed, stayed the same, or regressed based on detection of a ratio of Lamin C:Lamin A mRNAs or proteins.

Another aspect of the invention involves the detection of the amounts of Lamin A and Lamin C proteins in a biological sample instead of, or in addition to, detection of relative abundance of Lamin A and Lamin C mRNAs. A protein-based method for diagnosing a cancer or tumor involves quantitatively detecting the amounts of Lamin C and Lamin A proteins in a biological sample, and selecting a subject having a cancer or tumor when a ratio of the amount of Lamin C protein to Lamin A protein is elevated compared to the ratio in a control subject who does not have cancer or a tumor. Such a method may be used to diagnose or monitor and assess risk and efficacy of treatment for breast cancer, leukemia, ovary cancer, prostate cancer, colorectal cancer, thyroid cancer, liver cancer as well as other types of cancers exhibiting an abnormal ratio of Lamin C protein to Lamin A protein. Antibodies or other agents that specifically recognize Lamin A, but not Lamin C, and vice versa, are used to detect relative amounts of these proteins. Complex formation between an antibody or other agent is determined and used to determine the relative amounts of Lamin A and Lamin C in a sample.

A subject selected on the basis of an abnormal ratio or Lamin C to Lamin A proteins, characteristic of the presence of a tumor or cancer, may be treated by the administration of an anti-cancer or anti-tumor drug, radiation, immune response modifier or other therapeutic agent to the selected subject.

In another embodiment the ratio of Lamin C to Lamin A mRNA, or ratio of Lamin C to Lamin A proteins, is used to identify compounds having anticancer or antitumor activity or the ability to normalize or disrupt a Lamin C to Lamin A ratio. Such a method can involve comparing expression of the Lamin C:Lamin A ratio (mRNA or protein-based) in a first sample obtained from the patient and maintained in the presence of the test compound or agent, such as a physical, chemical or biologic agent, and expression of Lamin C to Lamin A ratio in a second sample obtained from the patient and maintained in the absence of the agent. A significantly lower level of expression of the Lamin C to Lamin A ratio in the first sample relative to that in the second sample is an indication that the agent is efficacious for inhibiting cancer in the patient.

For a nucleic acid based method, such a method involves contacting a tumor or cancer cell with a test compound, and quantitatively detecting mRNA encoding Lamin A and mRNA encoding Lamin C in the cell, calculating the ratio of Lamin C mRNA to Lamin A mRNA (Lamin C mRNA: Lamin A mRNA) in said cell, and selecting a test compound that decreases the ratio of Lamin C mRNA to Lamin A mRNA in the tumor or cancer cell compared to a control that has not been contacted with the test compound.

For a protein-based method (b) contacting a tumor or cancer cell with a test compound, quantitatively detecting Lamin A protein and Lamin C protein in the cell, calculating the ratio of Lamin C protein to Lamin A protein (Lamin C:Lamin A) in said tumor or cancer cell compared to control that has not been contacted with the test compound, and selecting a test compound that decreases the ratio of Lamin C protein to Lamin A protein in the tumor or cancer cell.

Conversely, a compound may also be selected for its ability to increase the ratio of Lamin C to Lamin A away from a normal or control range.

Another aspect of the invention is directed to a method of classifying a tumor comprising determining a relative expression of Lamin C mRNA versus Lamin A mRNA in a tumor sample classifying the tumor by criteria comprising the relative expression Lamin C mRNA and Lamin A mRNA.

The invention also relates to diagnostic, test and treatment kits. A kit is any manufacture (e.g., a package, box, envelope, bag, or other container or holder) comprising at least one reagent, such as a primer, primer set, probe, or antibody, for specifically detecting an altered ratio of Lamin C mRNA to Lamin A mRNA or altered levels of Lamin C and Lamin A proteins. The kit may be promoted, distributed, or sold as a unit for performing the methods disclosed herein. A kit may also contain positive or negative controls, instructions, or reagents for assessing the suitability of a physical, chemical or biologic agent for reducing the severity of a cancer in a patient. A kit may further comprise other diagnostic or therapeutic agents or for detecting and treating cancer.

Kits containing reagents, supplies, equipment for measuring a ratio of Lamin C mRNA to Lamin A mRNA may include a primer set for amplifying a portion of Lamin A mRNA distinct from Lamin C mRNA, a primer set for amplifying a portion of Lamin C mRNA distinct from Lamin A mRNA; and reagents for polymerase or reverse transcriptase amplification of mRNA, optionally probes that recognize Lamin A mRNA or Lamin C mRNA; and optionally equipment or containers for amplifying or detecting Lamin A or Lamin C nucleic acids, packaging materials, and/or instructions for use.

Kits containing reagents, supplies, equipment for determining a ratio of Lamin C protein to Lamin A protein may contain at least one antibody or other agent that binds to a portion of Lamin A distinct from Lamin C, at least one antibody of other agent that binds to a portion of Lamin C distinct from Lamin A, reagents for detecting complex formation between said agents and Lamin A or Lamin C and optionally equipment or containers for contacting said agents with a biological sample or detecting Lamin A or Lamin C proteins, packaging materials, and/or instructions for use.

EXAMPLES

The following list of embodiments is exemplary and in no way limits the scope of the disclosure.

Experimental Design: Differential mRNA expression levels of Lamin A, Lamin C, Lamin AΔ10 and Lamin AΔ50 were measured in 48 normal tissues/organs with newly designed TaqMan qRT-PCR assays. The expression of Lamin A/C alternative splice variants mRNA and the Lamin C:Lamin A ratio in 128 primary breast cancers and 16 normal breast tissues was also determined. Lamin A/C alternative splice variants mRNA and Lamin C:Lamin A ratios were analyzed and determined in seven other kinds of cancers.

Results: The ratio of mRNA encoding Lamin C to mRNA encoding Lamin A was increased in all clinical stages of breast cancer (Stage I to Stage IV). The mRNA expression levels of Lamin C increased significantly in breast tumors while the mRNA levels of Lamin A and Lamin AΔ50 were significantly decreased in breast tumors. However, no significant change in Lamin AΔ10 mRNA expression with respect to Lamin A mRNA expression was seen. An increased ratio of Lamin C:Lamin A mRNAs was also observed in liver, lung and thyroid carcinomas and colon, ovary, and prostate adenocarcinomas. These results demonstrate the value of determining a Lamin C:Lamin A mRNA ratio as a biomarker utility in breast cancer and for liver, lung and thyroid carcinomas and colon, ovary, and prostate adenocarcinomas.

Materials and Methods:

Human Normal Tissue cDNA and Cancer Tissue cDNA Arrays

TaqMan qPCR was utilized to measure the differential expression of Lamin A, Lamin C, Lamin AΔ10, and Lamin AΔ50 (Progerin) mRNA in 48 different normal tissues/organs (HMRT103, TissueScan qPCR Normal Tissue cDNA array, Origene Technologies Inc., Rockville, Md.).

The assay was also utilized to measure the differential expression of Lamin A/C transcript variants in TissueScan qPCR Breast Cancer DiWage Panels I, II and IV (BCRT101, BCRT102, BCRT104; Origene Technologies Inc.). Breast cancer cDNA arrays include 16—normal breast tissues and 128—breast adenocarcinoma tissues with tumor stage ranged from stage I to IV (23—Stage I, 36—IIA, 22—IIB, 8—IIIA, 23—IIIA, 6—IIIB, 13—IIIC, and 5—IV).

Additionally, the TaqMan qPCR was used to measure mRNA transcript variants of Lamin A/C in TissueScan qPCR Cancer Survey cDNA Array I (CSRT101, Origene Technologies Inc.) containing 96 samples covering 8 different cancer specimens of different histotypes. Cancer specimens include breast (N:3, SI:2, SII:2, SIII:3, SIV:2), colon (N:3, SI:1, SII:3, SIII:4, SIV:1), kidney (N:3, SI:3, SII: 1, SIII:3, SIV:2), liver (N:3, SI:3, SII:3, SIII:1, SIV:2), lung (N:3, SI:4, SII:2, SIII:3, SIV:1), ovarian (N:3, SI:3, SII: 1, SIII:4, SIV:1), prostate (N:3, hyperplasia: 5, prostatitis: 2 SII:1, SIII:1) and thyroid (N:3, S1:3, SII:2, SIII:2, SIV:2). The tissues, whose clinical pathological features are freely available at the following address: http://www.origene.com/qPCR/Tissue-qPCR-Arrays.aspx, were comprised of 50-90% tumor.

Lamin A/C Transcript Variants TaqMan Quantitative Real Time PCR (qRT-PCR)

Representative full-length mRNA transcript sequences for Lamin A (NM_170707.3) (SEQ ID NO: 1), Lamin C (NM_005572.3)(SEQ ID NO: 3), Lamin AΔ10 (NM_170708.3)(SEQ ID NO: 5) and Lamin AΔ50 (NM_001282626.1)(SEQ ID NO: 7) alternative splice variants were retrieved from the NCBI Reference Sequences database. The amino acid sequences of the polypeptides (CDS) encoded by each of these polynucleotide sequences are respectively described by SEQ ID NOS: 2, 4, 6, and 8.

Primers were designed based on theoretical optimal conditions, which include primer melting temperature, primer annealing temperature, GC content, cross homology and primer secondary structures.

To amplify Lamin C, a variant missing exons 11 and 12, a forward primer in exon 7, and a reverse primer located in a Lamin C specific 3' UTR in exon 10 were used. Lamin AΔ10 is missing exon 10. A forward primer design for Lamin AΔ10 spanning the exon 9-exon 11 junction was used, while the reverse primer was located downstream in exon 12.

For Lamin AΔ50 (Progerin), which is missing 150 nucleotides of exon 11, a forward primer spanning the cryptic splice site was used. The primers for Progerin were described and used by Scaffidi and Misteli, Nat. Med. 11: 440-5(2005).

These primers amplified a non-specific band. Accordingly, the inventor designed and employed a new probe in order to make the assay more specific. For the measurement of Lamin A, a forward primer targeting exon 10, which is missing in Lamin AΔ10, and a reverse primer targeting the deleted region of exon 11, which is missing in Progerin and Lamin C, were employed.

All probes were labeled with a fluorescent dye (FAM) for detection and a non-fluorescent quencher (BHQ-1). Primers and probes were custom ordered from Bio Basic Canada Inc. (Ontario, Canada). Sequences for all primer/probe combinations are as follows:

```
Lamin A:
The sequence of the probe is
5'-CGCTGAGTACAACCT-3';            (SEQ ID NO: 9)

The sequence of the forward primer is
5'-GACGAGGATGAGGATGGAGA-3';       (SEQ ID NO: 10)

The sequence of the reverse primer is
5'-GAGTGACCGTGACACTGGAG-3'.       (SEQ ID NO: 11)

Lamin C:
The sequence of the probe is
5'-AGATGACCTGCTCCATCACC-3';       (SEQ ID NO: 12)

The sequence of the forward primer is
5'-GTGGAAGGCACAGAACACCT-3;        (SEQ ID NO: 13)

The sequence of the reverse primer is
5'-GCGGCGGCTACCACTCAC-3'.         (SEQ ID NO: 14)

Lamin AΔ10:
The sequence of the probe is
5'-AGTACAACCTGCGCTCGCGC-3';       (SEQ ID NO: 15)

The sequence of the forward primer is
5'-AACTCCACTGGGGAAGGCTCC-3';      (SEQ ID NO: 16)

The sequence of the reverse primer is
5'-GCTCCTGAGCCGCTGGCAGA-3'.       (SEQ ID NO: 17)

Lamin AΔ50:
The sequence of the probe is
5'-AGCATCATGTAATCTGGGACCT-3';     (SEQ ID NO: 18)

The sequence of the forward primer is
5'-GCGTCAGGAGCCCTGAGC-3;          (SEQ ID NO: 19)

The sequence of the reverse primer is
5'-GACGCAGGAAGCCTCCAC-3'.         (SEQ ID NO: 20)

Ubiquitin:
The sequence of the probe is
5'-CCCACCTCfGAGACGGAGCACCAG-3';   (SEQ ID NO: 21)

The sequence of the forward primer is
5'-ACTACAACATCCAGAAAGAGTCCA-3';   (SEQ ID NO: 22)

The sequence of the reverse primer is
5'-CCAGTCAGGGTCTTCACGAAG-3'.      (SEQ ID NO: 23)

RPL-13:
The sequence of the probe is
5'-CGCAAGCGGATGAACACCAACCCT-3';   (SEQ ID NO: 24)

The sequence of the forward primer is
5'-AACAAGTTGAAGTACCTGGCTTTC-3';   (SEQ ID NO: 25)

The sequence of the reverse primer is
5'-TGGTTTTGTGGGGCAGCATA-3'.       (SEQ ID NO: 26)

β-Actin:
The sequence of the probe is
5'-CGGCTACAGCTTCACCACCACGGC-3';   (SEQ ID NO: 27)

The sequence of the forward primer is
5'-TGACTGACTACCTCATGAAGATCC-3';   (SEQ ID NO: 28)

The sequence of the reverse primer is
5'-CCATCTCTTGCTCGAAGTCCAG-3.      (SEQ ID NO: 29)
```

A volume reaction of 20 µL was used for RT-qPCR. The probe reaction assay consisted of 100 mM KCl, 20 mM Tris, pH 9.2, 5 mM $MgSO_4$, 0.02% Triton X-100, 0.2 mM dNTP, 200 mM Betaine, 5% DMSO and 1.25 IU Taq Polymerase, 0.2 µM Sense/Anti-sense primers and 2 µL of cDNA. qPCR reactions were run on Cepheid Smartcycler (Sunnyvale, Calif.). The reaction protocol consisted of one activation cycle of 50° C. for 2 minutes followed by 95° C. for 15 seconds. After this step, 40 cycles of denaturation at 95° C. for 15 seconds, and annealing/extension (Lamin A: 58° C., Lamin Δ50: 60° C., Lamin Δ10: 66° C., Lamin C: 60° C.) for 2 minutes were performed. The inter- and intra-assay coefficients of variability for the probe based qRT-PCR assay established were less than 10%. All samples were normalized to the average expression levels of the 3 housekeeping genes: β-actin, RPL-13 and ubiquitin. Q-Gene software was used for calculations and efficiency corrections (BioTechniques, Carlsbad, Calif., USA). The number of replicates and the composition of the samples varied depending on the particular experiment but were never less than triplicate.

Positive and Negative Controls for TaqMan Assay of Lamin A/C Transcript Variants Lamin A/C cDNA transcript variants (Lamin A, Lamin C, Progerin, and Lamin Δ10) were used to confirm qPCR specificity reactions. Lamin A, Lamin C and Lamin Δ10 cDNA were purchased from OriGene Inc. and Progerin plasmid, developed by Dr. Mistcli, Nat. Med. 11:440-5 (2005), was purchased from Addgene (Cambridge, Mass.). Plasmids were digested using EcoR1 restriction enzymes (Sigma, St. Louis, Mo.). The amplified products were sequenced. The probe sensitivity was tested by performing Lamin A/C transcript variants TaqMan qRT-PCR at different number of DNA template copies. The assay was able to detect the corresponding transcript variant to approximately 30 copies of DNA template. Average Cycle Threshold (Ct) values were used to determine sensitivity and specificity of the designed probes. Cross reactions of Lamin A/C transcript variants Essays were not observed.

Statistical Analysis of Microarray Data

Statistical analysis was performed using SigmaStat software version 3.5 (Systat Software, San Jose, Calif.). Analysis was carried out with Maim-Whitney Rank Sum Test between normal and tumor specimens. Kruskal-Wallis One Way Analysis of Variance (ANOVA) on Ranks was used to compare between normal specimen and different stages of breast cancer followed by Dunn's test for all pairwise comparisons and comparisons against the control group.

Lamin A/C Transcript Variants TaqMan qPCR Primer/Probe Optimization

The primers for Lamin A/C transcript variants (Lamin A, Lamin C, Lamin AΔ10, and Progerin) amplified the expected amplicon sizes (FIG. 1A-D). The specificity of each primer pair was evaluated with Lamin A/C transcript variants cDNAs (FIG. 1E-H). For Progerin, we evaluated two primer combinations, which have been used previously.

The first primer set was designed by Scaffidi and Misteli, S: 5' GCGTCAGGAGCCCTGAGC 3' (SEQ ID NO: 19) and A: 5' GACGCAGGAAGCCTCCAC 3' (SEQ ID NO: 20), Scaffidi, et al. Nat. Med. 11:440-5 (2005). A non-specific band was amplified with all LMNA/C transcript variants at high cycle number (FIG. 1H). Addition of a Taqman probe with this primer set eliminated this non-specificity in our real time PCR assay.

The second set for Progerin was designed by Rodriguez et al., Eur. J. Hum. Genet. (2009), S: 5' ACTGCAGCAGCTCGGGG 3' (SEQ ID NO: 30), and A: 5' TCTGGGGGCTCTGGGC 3' (SEQ ID NO: 31) and the probe used was 5' (FAM) CGCTGAGTACAACCT (BHQ) 3' (SEQ ID NO: 32). This primer/probe set also amplified non-specifically Lamin A cDNA, and Lamin AA 10 cDNA.

Probe sensitivity was tested by performing Lamin A or Lamin C or Lamin AΔ10 or Progerin.

TaqMan qRT-PCR assays were performed with a serial dilution of approximately 300,000 to 30 copies of plasmid DNA of either Lamin A, Lamin C, Lamin AΔ10, Progerin cDNAs, or an empty vector control.

The slope and regression coefficient ($r^2$ value) of the standard dilution curves are indicated below each curve in FIG. 2. The inter- and intra-assay coefficients of variability for all the probe based qPCR assays established for Lamin A/C transcript variants were less than 10% and cross reactions of Lamin A/C transcript variants assays were not observed.

Differential Expression of Lamin A/C Alternative Splice Variants in Normal Tissue cDNA Array Expression of Lamin A, Lamin C, Lamin AΔ10, and Progerin mRNA in the 48 different normal tissues/organs included in the cDNA array demonstrated that, even within the same tissue, the mRNA expressions of Lamins are not coinciding for most of tissues (Table 1). The stomach tends to show high expression of all Lamins, while lymphocytes located in peripheral blood tends to show the least mRNA expression for Lamin C and Progerin. The highest mRNA expression of Lamin A was observed in the uterus while the least expression was found in the skeletal muscle.

On other hand, Lamin C was expressed maximally in stomach and least in peripheral lymphocytes and brain. The placenta showed very high expression of Lamin AΔ10 followed by seminal vesicles while the kidney showed the least mRNA expression. On other hand the small intestine expressed the highest Progerin mRNA and peripheral lymphocytes showed minimal expression of Progerin mRNA (Table 1).

TABLE 1

Differential expression levels of Lamin A, Lamin C, Lamin AΔ10, and Progerin mRNA in 40 different normal tissues/organs (HMRT103, TissueScan qPCR Normal Tissue cDNA array). Results are presented as Mean ± SEM.

| | Lamin A ± SEM ($\times 10^{-3}$) | Lamin C ± SEM ($\times 10^{-3}$) | Lamin AΔ10 ± SEM ($\times 10^{-6}$) | Progerin ± SEM ($\times 10^{-6}$) |
|---|---|---|---|---|
| Adrenal Gland | 6.97 + 0.70 | 23.5 + 2.51 | 32.00 + 4.18 | 17.50 + 2.88 |
| Bone Marrow | 4.44 ± 0.92 | 4.02 ± 0.19 | 9.14 ± 4.75 | 7.95 ± 4.48 |
| Brain | 3.01 ± 0.42 | 0.75 ± 0.04 | 19.50 ± 6.43 | 7.42 ± 5.44 |
| Cervix | 6.12 ± 0.09 | 19.00 ± 0.13 | 23.00 ± 0.96 | 2.71 ± 0.60 |
| Colon | 4.94 ± 0.37 | 5.82 ± 0.54 | 20.90 ± 2.16 | 12.60 ± 8.27 |
| Descending part of duodenum | 4.27 ± 0.61 | 6.16 ± 0.70 | 10.90 ± 6.51 | 9.97 ± 1.00 |
| Epididymis | 4.32 ± 0.53 | 2.03 ± 1.41 | 14.10 ± 0.245 | 8.00 ± 2.81 |
| Esophagus | 5.06 ± 1.17 | 4.78 ± 0.50 | 41.80 ± 21.90 | 17.20 ± 8.17 |
| Fat | 5.70 ± 0.53 | 9.01 ± 0.90 | 20.60 ± 2.42 | 16.30 ± 10.90 |
| Heart | 3.86 ± 0.23 | 5.88 ± 2.40 | 19.60 ± 1.43 | 7.79 ± 2.03 |
| Heart, Ventricle (left) | 7.70 ± 0.03 | 5.43 ± 0.47 | 20.10 ± 6.14 | 7.18 ± 3.87 |
| Heart, Ventricle (right) | 6.45 ± 0.51 | 4.29 ± 1.61 | 13.10 ± 0.23 | 5.03 ± 1.91 |
| Kidney | 5.19 ± 1.78 | 6.06 ± 1.20 | 3.31 ± 0.43 | 4.45 ± 0.70 |
| Liver | 3.64 ± 0.77 | 4.63 ± 0.90 | 7.28 ± 2.20 | 2.57 ± 0.08 |
| Lung | 6.10 ± 1.21 | 9.33 ± 1.82 | 18.60 ± 3.32 | 14.20 ± 2.57 |
| Lymph Node | 3.53 ± 0.44 | 4.87 ± 0.15 | 12.70 ± 1.14 | 10.10 ± 0.31 |
| Lymphocytes (peripheral blood) | 4.24 ± 1.74 | 0.45 ± 0.11 | 7.12 ± 1.37 | 1.62 ± 0.19 |
| Mammary gland | 5.10 ± 0.96 | 7.94 ± 0.58 | 20.90 ± 0.72 | 10.50 ± 2.23 |
| Muscle | 2.73 ± 0.13 | 2.02 ± 0.06 | 22.50 ± 12.20 | 8.21 ± 2.46 |
| Nasal mucosa | 4.08 ± 0.55 | 3.96 ± 0.86 | 9.66 ± 3.66 | 8.47 ± 1.28 |
| Optic nerve | 3.58 ± 0.92 | 1.46 ± 0.16 | 20.10 ± 2.97 | 3.09 ± 0.17 |
| Ovary | 4.32 ± 0.15 | 4.61 ± 0.21 | 25.20 ± 0.35 | 3.88 ± 1.53 |
| Oviduct | 5.93 ± 0.35 | 16.30 ± 1.41 | 12.50 ± 1.42 | 13.70 ± 1.89 |
| Pancreas | 5.17 ± 1.15 | 6.04 ± 1.42 | 9.43 ± 2.91 | 3.89 ± 0.72 |
| Penis | 3.67 ± 0.04 | 1.82 ± 0.41 | 9.21 ± 3.84 | 2.12 ± 0.68 |
| Pericardium | 3.17 ± 0.51 | 1.27 ± 0.26 | 10.70 ± 5.21 | 2.36 ± 1.31 |
| Pituitary | 5.61 ± 0.75 | 6.06 ± 0.48 | 34.00 ± 0.47 | 10.30 ± 3.33 |
| Placenta | 7.10 ± 0.47 | 6.86 ± 0.76 | 99.60 ± 13.00 | 16.30 ± 2.96 |
| Prostate | 4.75 ± 10.31 | 5.04 ± 0.38 | 18.50 ± 2.99 | 6.95 ± 4.01 |
| Retina | 3.41 ± 1.55 | 2.73 ± 0.30 | 9.97 ± 5.76 | 9.01 ± 3.25 |
| Seminal vesicles | 3.58 ± 0.59 | 8.30 ± 4.52 | 44.30 ± 23.60 | 20.40 ± 3.63 |
| Skin | 10.7 ± 2.05 | 22.20 ± 0.65 | 18.00 ± 0.19 | 13.60 ± 4.89 |
| Spinal Cord | 3.83 ± 0.86 | 3.09 ± 0.25 | 23.90 ± 12.40 | 3.79 ± 0.60 |
| Spleen | 6.85 ± 0.21 | 12.60 ± 0.44 | 13.50 ± 3.48 | 11.70 ± 0.77 |
| Stomach | 10.2 ± 0.85 | 44.30 ± 8.40 | 42.10 ± 0.88 | 28.60 ± 6.05 |
| Testis | 8.44 ± 0.87 | 27.90 ± 0.39 | 30.60 ± 11.20 | 17.80 ± 7.21 |
| Thymus | 5.28 ± 0.26 | 3.67 ± 0.30 | 38.40 ± 12.70 | 6.98 ± 3.26 |
| Thyroid | 5.03 ± 0.21 | 10.90 ± 2.14 | 18.10 ± 7.28 | 9.56 ± 2.95 |
| Tongue | 3.90 ± 0.72 | 2.33 ± 0.13 | 18.10 ± 4.90 | 1.31 ± 0.90 |
| Tonsil | 4.42 ± 0.64 | 1.86 ± 0.29 | 13.90 ± 8.63 | 8.17 ± 2.00 |
| Trachea | 6.61 ± 0.25 | 15.60 ± 1.02 | 42.30 ± 11.30 | 20.50 ± 0.07 |
| Ureter | 4.66 ± 0.10 | 13.20 ± 0.83 | 10.20 ± 5.60 | 8.34 ± 2.04 |
| Urinary Bladder | 7.08 ± 1.91 | 10.60 ± 6.33 | 16.80 ± 9.13 | 23.90 ± 0.99 |
| Uterus | 12.3 ± 2.44 | 8.54 ± 0.79 | 34.10 ± 6.30 | 6.00 ± 0.48 |
| Uvula | 5.80 ± 1.46 | 7.21 ± 1.02 | 43.30 ± 3.74 | 8.55 ± 2.00 |
| Vagina | 5.88 ± 0.14 | 7.42 ± 2.29 | 14.90 ± 11.00 | 8.91 ± 4.04 |
| Intestine (small) | 5.84 ± 0.75 | 10.7 ± 0.49 | 19.00 ± 4.96 | 49.20 ± 0.85 |

Altered Expression of Lamin A/C Alternative Splice Variants in Breast Cancer

To evaluate the relative expression of Lamin A, Lamin C, Lamin AΔ10 and Progerin mRNA in breast cancer, Breast Cancer cDNA arrays (BCRT101, BCRTIO2 and BCRT104) from Origene Inc. were utilized.

As shown in FIG. 3, the median normalized expression of Lamin A was statistically significantly lower (Mann-Whitney Rank Sum Test; FIG. 3A; $P<0.05$) in breast cancer (Q1-Q3: $7.77\times10^{-3}$-$21.80\times10^{-3}$) when compared to normal breast tissue (Q1-Q3: $14.30\times10^{-3}$-$20.70\times10^{-3}$).

Lamin C mRNA expression was upregulated significantly (Mann-Whitney Rank Sum Test; FIG. 3B; $P<0.001$) in breast cancer (Q1-Q3: $32.9\times10^{-3}$-$122.0\times10^{-3}$) when compared to normal breast tissue (Q1-Q3: $23.4\times$-$31.8\times10^{-3}$).

There was no significant change in Lamin AΔ10 mRNA expression (FIG. 3C).

Figure 3D:
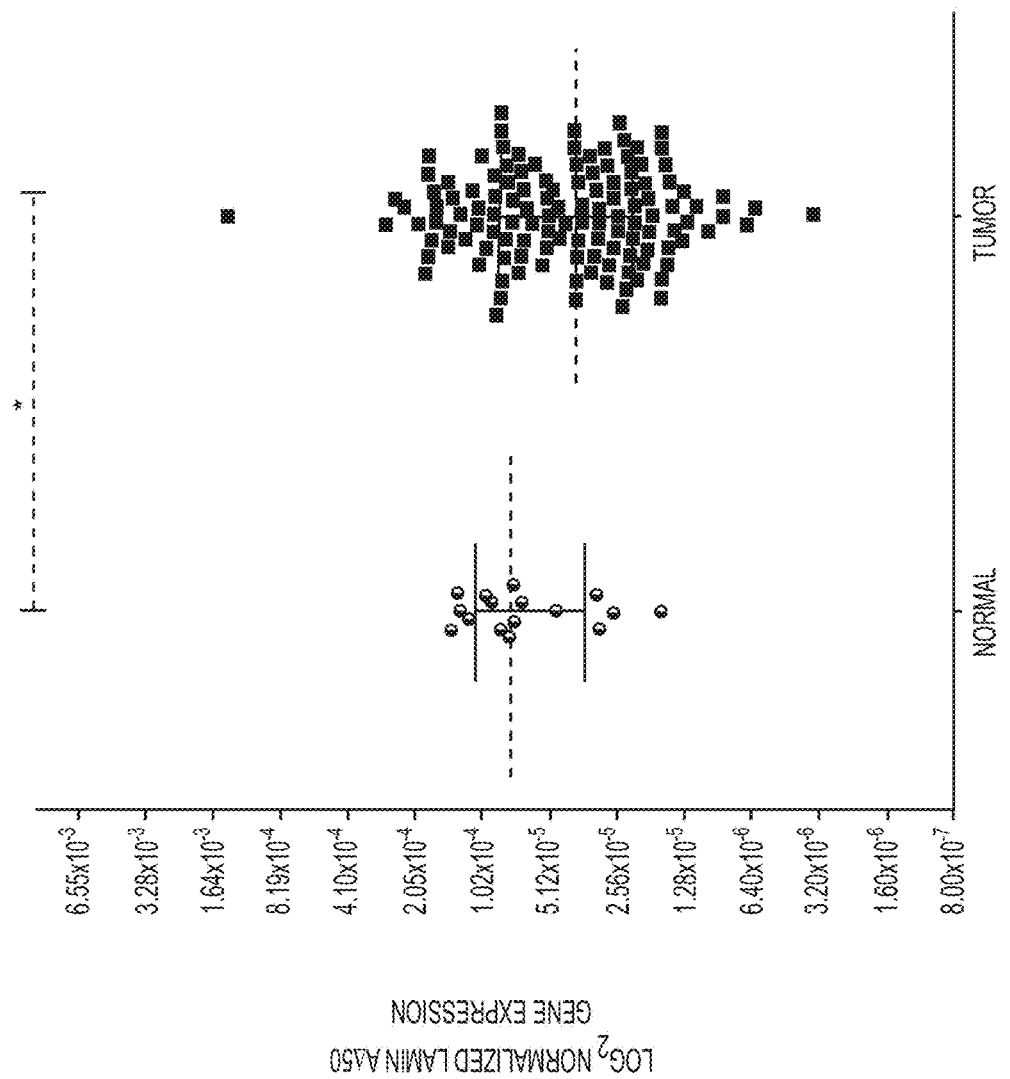

Progerin was statistically significantly lower (Mann-Whitney Rank Sum Test; FIG. 3D; $P<0.05$) in breast cancer (Q1-Q3: $2.20\times10^{-5}$-$8.49\times10^{-5}$) when compared to normal breast tissue (Q1-Q3: $3.62\times10^{-5}$-$11.20\times10^{-5}$).

Clinical stage (CS) is an established indicator of breast cancer outcome. To determine Lamin A alternative splice variants expression profiles of the premalignant, preinvasive and invasive stages of breast cancer progression, patients were stratified into groups according to metastatic stages as follows 16—normal, 23—CS-I, 36—IIA, 22—IIB, 23—IIIA, 6—IIIB, 13—IIIC, 5—IV.

This revealed statistically significantly higher levels of Lamin C mRNA (FIG. 4B; One Way ANOVA on Ranks; $P<0.001$) in CS-IIA to CS-IIIC compared to normal breast tissues.

There were no statistically significant changes of other Lamin A/C transcript variants except Progerin (CS-IIA) possibly due to small number of patients per each group (FIG. 4).

Increased Ratio of Lamin C to Lamin A in Breast Cancer

The inventor calculated the mRNA transcript ratios of Lamin C to Lamin A in normal and primary breast tumor samples. The mean Lamin C:Lamin A ratios ±95% CI were 1.56±0.16 and 5.92±0.73 in the normal (n=16) and primary tumors (n=128), respectively. A Mann-Whitney Rank Sum Test between normal and primary breast tumor samples analysis identified a significant difference between normal and tumor samples for Lamin C:Lamin A ratio, ($P<0.0001$; FIG. 5A).

The results indicate that there was a significant increase in the ratio of Lamin C:Lamin A in breast tumors. Further stratifications of metastatic stages showed statistical significance in Lamin C:Lamin A ratio in all clinical stages of breast cancer (CS-I to CS-IV) and normal breast tissues (FIG. 5B: One Way ANOVA on Ranks; $P<0.001$).

Increased Lamin C to Lamin A Ratio in Multiple Tumor Types

To examine whether the increase in Lamin C or Lamin C:Lamin A mRNA ratio is a common event occurring in different cancer types, the inventor used a commercially available Cancer Survey cDNA array (CSRT101) containing 8 different types of cancers with their corresponding normal tissues to assess Lamin A, Lamin C, Lamin AΔ10 and Progerin mRNA expression status in tumor and normal tissues. Although the number of specimens included in the TissueScan qPCR Cancer Survey cDNA array was low, a Mann-Whitney Rank Sum Test between normal (n=3) and tumor (n=9) specimens analysis identified a significant difference between normal and tumor samples for Lamin A ($P<0.05$; FIG. 6A) in colon and thyroid cancers. There was a statistical trend ($P=0.064$) in liver carcinoma. There were no significant changes in other Lamin A/C transcript variants (FIG. 6). However, there were significant differences in Lamin C:Lamin A ratios in breast, colon, liver; lung, ovary, thyroid, and prostate cancers when compared to their normal corresponding tissues (FIG. 7).

The invention claimed is:

1. A method for identifying a human subject with an increased risk of breast, colon, liver, lung, ovary, thyroid, or prostate cancer, comprising:
   (a) obtaining from a human subject a tissue sample suspected of containing breast, colon, liver, lung, ovary, thyroid, or prostate cancer cells;
   (b) quantitatively detecting levels of Lamin A and Lamin C mRNA in the tissue sample by a TaqMan quantitative real-time polymerase chain reaction;
   (c) calculating the ratio of Lamin C mRNA to Lamin A mRNA in the tissue sample;
   (d) identifying the human subject as having an increased risk of breast, colon, liver, lung, ovary, thyroid, or prostate cancer when the tissue sample has an elevated ratio of Lamin C mRNA to Lamin A mRNA as calculated in (c) in comparison to a ratio of Lamin C mRNA to Lamin A mRNA in a control non-cancerous human tissue sample; and
   (e) treating the identified human subject for breast, colon, liver, lung, ovary, thyroid, or prostate cancer,
      wherein a Lamin A probe that comprises 5'-CGCTGAGTACAACCT-3' (SEQ ID NO: 9); a Lamin A forward primer that comprises 5'-GACGAGGATGAGGATGGAGA-3' (SEQ ID NO: 10); and a Lamin A reverse primer that comprises 5'-GAGTGACCGTGACACTGGAG-3' (SEQ ID NO: 11) is used for said TaqMan quantitative real-time polymerase chain reaction; and/or
      wherein a Lamin C probe that comprises 5'-AGATGACCTGCTCCATCACC-3' (SEQ ID NO: 12); a Lamin C forward primer that comprises 5'-GTGGAAGGCACAGAACACCT-3' (SEQ ID NO: 13); and a Lamin C reverse primer that comprises 5'-GCGGCGGCTACCACTCAC-3' (SEQ ID NO: 14) is used for said TaqMan quantitative real-time polymerase chain reaction.

2. A method for identifying a human subject with an increased risk of breast, colon, liver, lung, ovary, thyroid, or prostate cancer, comprising:
   (a) obtaining from a human subject a tissue sample suspected of containing breast, colon, liver, lung, ovary, thyroid, or prostate cancer cells;
   (b) quantitatively detecting levels of Lamin A and Lamin C mRNA in the tissue sample by a TaqMan quantitative real-time polymerase chain reaction;
   (c) calculating the ratio of Lamin C mRNA to Lamin A mRNA in the tissue sample;
   (d) identifying the human subject as having an increased risk of breast, colon, liver, lung, ovary, thyroid, or prostate cancer when the tissue sample has an elevated ratio of Lamin C mRNA to Lamin A mRNA as calculated in (c) in comparison to a ratio of Lamin C mRNA to Lamin A mRNA in a control non-cancerous human tissue sample; and
   (e) treating the identified human subject for breast, colon, liver, lung, ovary, thyroid, or prostate cancer,
      wherein said treating comprises administering at least one of an anti-cancer or anti-tumor drug, radiation, immune response modifier, Lamin A modulator, or Lamin C modulator.

* * * * *